United States Patent
Chaudhari et al.

(10) Patent No.: US 10,821,422 B2
(45) Date of Patent: Nov. 3, 2020

(54) METHODS OF FORMING AND USING METAL ALLOY OXIDATIVE CATALYSTS

(71) Applicant: UNIVERSITY OF KANSAS, Lawrence, KS (US)

(72) Inventors: Raghunath V. Chaudhari, Lawrence, KS (US); Xin Jin, Lawrence, KS (US); Bala Subramaniam, Lawrence, KS (US)

(73) Assignee: UNIVERSITY OF KANSAS, Lawrence, KS (US)

( * ) Notice: Subject to any disclaimer, the term of this patent is extended or adjusted under 35 U.S.C. 154(b) by 59 days.

(21) Appl. No.: 15/776,835

(22) PCT Filed: Nov. 17, 2016

(86) PCT No.: PCT/US2016/062506
§ 371 (c)(1),
(2) Date: May 17, 2018

(87) PCT Pub. No.: WO2017/087657
PCT Pub. Date: May 26, 2017

(65) Prior Publication Data
US 2019/0308175 A1    Oct. 10, 2019

Related U.S. Application Data

(60) Provisional application No. 62/256,353, filed on Nov. 17, 2015.

(51) Int. Cl.
*B01J 23/89* (2006.01)
*B01J 21/06* (2006.01)
(Continued)

(52) U.S. Cl.
CPC ......... *B01J 23/8926* (2013.01); *B01J 21/063* (2013.01); *B01J 23/002* (2013.01);
(Continued)

(58) Field of Classification Search
CPC .... B01J 23/8926; B01J 21/063; B01J 23/002; C07C 51/00; C07C 51/16; C07C 51/235
(Continued)

(56) References Cited

U.S. PATENT DOCUMENTS 8,669,397 B2   3/2014   Boussie et al.
8,975,453 B2   3/2015   He et al.
(Continued)

OTHER PUBLICATIONS

Jin, Xin et al., Journal of Catalysis, Aug. 27, 2015 (e-pub), vol. 330, pp. 323-329.*
(Continued)

*Primary Examiner* — Deborah D Carr
(74) *Attorney, Agent, or Firm* — Stinson LLP

(57) ABSTRACT

In a first aspect, the present invention is directed to a process for forming a metal alloy catalyst. Another aspect of the present invention is directed to a process for oxidizing a substrate that includes contacting a substrate with an oxidant in the presence of a metal alloy catalyst to form one or more carboxylic acids. Suitable substrates include sugars, polyols, furfural alcohols, and polyhydroxycarboxylic acids. The oxidation process may use the alloy catalyst formed from the process of the first aspect of the invention.

25 Claims, 36 Drawing Sheets

(51) Int. Cl.

| | |
|---|---|
| B01J 23/44 | (2006.01) |
| B01J 23/78 | (2006.01) |
| B01J 35/10 | (2006.01) |
| B01J 37/00 | (2006.01) |
| B01J 37/02 | (2006.01) |
| B01J 37/03 | (2006.01) |
| B01J 37/06 | (2006.01) |
| B01J 37/16 | (2006.01) |
| C07C 51/16 | (2006.01) |
| B01J 35/00 | (2006.01) |
| B01J 37/08 | (2006.01) |
| B01J 23/00 | (2006.01) |
| C07C 51/235 | (2006.01) |
| C07C 51/00 | (2006.01) |

(52) U.S. Cl.
CPC .............. *B01J 23/44* (2013.01); *B01J 23/78* (2013.01); *B01J 23/894* (2013.01); *B01J 23/8906* (2013.01); *B01J 35/006* (2013.01); *B01J 35/1009* (2013.01); *B01J 37/009* (2013.01); *B01J 37/0236* (2013.01); *B01J 37/033* (2013.01); *B01J 37/035* (2013.01); *B01J 37/06* (2013.01); *B01J 37/082* (2013.01); *B01J 37/16* (2013.01); *C07C 51/00* (2013.01); *C07C 51/16* (2013.01); *C07C 51/235* (2013.01); *B01J 35/002* (2013.01); *B01J 2523/00* (2013.01)

(58) Field of Classification Search
USPC ....................................................... 562/515
See application file for complete search history.

(56) References Cited

U.S. PATENT DOCUMENTS

| | | | |
|---|---|---|---|
| 9,085,521 | B2 | 7/2015 | Chaudhari et al. |
| 9,163,041 | B2 | 10/2015 | Wan |
| 9,770,705 | B2 | 9/2017 | Murphy et al. |
| 2010/0317823 | A1 | 12/2010 | Boussie et al. |
| 2011/0124500 | A1 | 5/2011 | Fang et al. |
| 2014/0256982 | A1 | 9/2014 | Boussie et al. |

OTHER PUBLICATIONS

Jin, et al., Abstract, "Selective Oxidation of Sugars and Polyols to Disaccharic Acids on Pt-Based Catalysts in One Pot Process", Center for Environmentally Beneficial Catalysis, Chemical & Petroleum Engineering, University of Kansas, Lawrence, Kansas, 2014 (1 pg).

Jin, et al., Powerpoint Presentation, "Activity and Selectivity of mono and Bimetallic Pt-Based Nano-Catalysts for Oxidation of Sugars and Polyols to Aldaric Acids", 3rd International Symposium on Green Chemistry, La Rochelle, France, May 5, 2015 (14 pgs).

Jin, et al., Powerpoint Presentation, "Synthesis of Disaccharic Acids from Biomass on Mono and Bimetallic PT Solid Catalysts", Nov. 17, 2014 (40 pgs).

Jin, et al., Abstract, "Biomass conversion—Atom-Economy Synthesis", 3rd International Symposium on Green Chemistry, La Rochelle, France, May 3-7, 2015 (2 pgs).

Villa, et al., Article, "Pd-modified Au on Carbon as an Effective and Durable Catalyst for the Direct Oxidation of HMF to 2,5-Furandicarboxylic Acid", ChemSusChem 2013, vol. 6, pp. 609-612 (4 pgs).

Liang, et al., Article, "Bimetallic Pt—Cu Catalysts for Glycerol Oxidation with Oxygen in a Base-Free Aqueous Solution", Catalysis Communications 12 (2011), pp. 1059-1062 (4 pgs).

Shiraishi, et al., Article, "Pt—Cu Bimetallic Alloy Nanoparticles Supported on Anatase $TiO_2$: Highly Active catalysts for Aerobic Oxidation Driven by Visible Light", ACSNANO.Org, vol. 7, No. 10, 2013, pp. 9287-9297 (11 pgs).

Zhang, et al., Article, "Recent Advances in the Catalytic Synthesis of 2,5-Furandicarboxylic Acid and its Derivatives", American Chemical Society Catal. 2015, vol. 5, pp. 6529-6544 (16 pgs).

Van De Vyver, et al., Article, "Emerging Catalytic processes for the Production of Adipic Acid", The Royal Society of Chemistry, Catal. Sci. Technol., 2013, vol. 3, pp. 1465-1479 (15 pgs).

Ibert, et al., Article, "Determination of the Side-Products Formed During the Nitroxide-Mediated Bleach Oxidation of Glucose to Glucaric Acid", Carbohydrate Research 337, 2002, pp. 1059-1063 (5 pgs).

Smith, et al., Article, "Modifications in the Nitric Acid Oxidation of D-Glucose", Carbohydrate Research 350, 2012, pp. 6-13 (8 pgs).

Draths, et al., Article, "Environmentally Compatible Synthesis of Adipic Acid from D-Glucose", J. Am. Chem. Soc. 1994, vol. 116, pp. 399-400 (2 pgs).

Dijkgraff, Thesis, "Oxidation of Glucose to Glucaric Acid by Pt/C Catalysts", published 1988 (105 pgs).

Jin, et al., Article, "Synergistic Effects of Bimetallic $PtPd/TiO_2$ Nanocatalysts in Oxidation of Glucose to Glucaric Acid: Structure Dependent Activity and Selectivity", Ind. Eng. Chem. Res., 2016, vol. 55, pp. 2932-2945 (14 pgs).

Jin, et al., Article, "Anisotropic Growth of PtFe Nanoclusters Induced by Lattice-Mismatch: Efficient Catalysts for Oxidation of Biopolyols to Carboxylic Acid Derivatives", Journal of Catalysis 337, 2016, pp. 272-283 (12 pgs).

Jin, et al., Article, "Exceptional Performance of Bimetallic $Pt_1CU_3/TiO_2$ Nanocatalysts for Oxidation of Gluconic Acid and Glucose with $O_2$ to Glucaric Acid", Journal of Catalysis 330, 2015, pp. 323-329 (16 pgs).

\* cited by examiner

METHODS OF FORMING AND USING METAL ALLOY OXIDATIVE CATALYSTS

CROSS-REFERENCE TO RELATED APPLICATIONS

This application is based on and claims priority to U.S. Provisional Application Ser. No. 62/256,353 filed on Nov. 17, 2015, which is hereby incorporated herein by reference.

BACKGROUND OF THE INVENTION

1. Field of the Invention

The present invention relates to the field of oxidation catalysts.

2. Description of Related Art

Dicarboxylic acids such as glucaric acid, malonic acid, tartronic acid, oxalic acid, furan dicarboxylic acid, and adipic acid are precursors for many products such as food containers, medicines, food additives, industrial solvents, nylon, hydrophilic drugs, and flavorants. In particular, glucaric acid has been classified by the United States Department of Energy as a versatile platform chemical from biomass for making a number of these products, and is an important precursor for adipic acid, one of the most widely used chemicals in industry.

Conventional processes for the manufacture of dicarboxylic acids typically involve the use of toxic and highly corrosive oxidants and catalysts such as nitric acid, cyanides, and/or halogen-containing solid catalysts. The conventional processes are typically energy intensive and use expensive catalysts. Furthermore, the conventional processes often require the use of bleach chemicals such as 2,2,6,6-tetramethyl-1-piperidinyloxy, sodium bromide (NaBr), sodium hypochlorite (NaOCl) and mineral acids. Uncontrollable temperature spikes caused by oxidation reactions frequently accompany the conventional processes. The conventional processes also frequently result in the generation of significant quantities of toxic by-products such as waste acids, inorganic salts, and/or chlorides. Additionally, the separation of the catalysts of the conventional processes from the reaction medium often requires chemical and energy intensive procedures.

Although noble metal catalysts have been used to form dicarboxylic acids, the reported oxidation activity of such catalysts is low.

Based upon the foregoing, there is a need for more environmentally friendly processes that improve the yield of carboxylic acids such as glucaric acid and that improve upon the oxidation rates of the substrates used to form such carboxylic acids.

BRIEF SUMMARY OF THE INVENTION

In a first aspect, the present invention is directed to a process for forming an alloy catalyst wherein a metal precursor of a first metal, a metal precursor of a second metal and a solid support are combined in a solvent to form an alloy catalyst. Preferably the metal precursors are co-precipitated to form the alloy. In one such embodiment, the process of the first aspect of the invention includes the steps of: forming a metal precursor solution that includes a metal precursor of a first metal and a metal precursor of a second metal; forming a solid support solution that includes a solid support and a solvent; combining the metal precursor solution and the solid support solution to form a combined solution; and adding a reducing agent to the combined solution to form the alloy catalyst.

In one embodiment of the first aspect of the invention, the molar concentration of the metal precursor of the first metal in the metal precursor solution is preferably $10^{-5}$ to $10^{-1}$ kmol/m$^3$, and the molar concentration of the metal precursor of the second metal in the metal precursor solution is $10^{-5}$ to $10^{-1}$ kmol/m$^3$. More preferably, the molar concentration of the metal precursor of the first metal precursor solution is $10^{-4}$ to $10^{-3}$ kmol/m$^3$, and a molar concentration of said metal precursor of said second metal precursor solution is $10^{-4}$ to $10^{-3}$ kmol/m$^3$.

In an embodiment of the first aspect of the present invention, the solvent is selected from the group consisting of acetonitrile, C1-C4 alcohols and nitriles.

In another embodiment of the first aspect of the present invention, the ratio of the metal precursor solution to the solid support solution in the combined solution is preferably 1/100 to 200/100 (v/v), more preferably 30/100 to 200/100 (v/v), and most preferably 100/100 to 200/100 (v/v).

In yet another embodiment of the first aspect of the present invention, the concentration of the solid support in the combined solution is preferably 0.2 to 10.0 (g/L), and more preferably 1.0 to 5.0 (g/L).

In still another embodiment of the first aspect of the present invention, the combined solution is mixed for a period of time preferably ranging from 1 hour to 20 hours before adding the reducing agent, and more preferably from 6 hours to 12 hours.

In one more embodiment of the first aspect of the present invention, the reducing agent is added as a reducing agent solution having a concentration of reduction agent preferably from 0.001 to 0.1 (mol/L), and more preferably from 0.001 to 0.01 (mol/L).

In an embodiment of the first aspect of the present invention, the reducing agent is sodium borohydride (NaBH$_4$).

In yet another embodiment of the first aspect of the present invention, the ratio of the reducing agent solution to the combined solution is 1/5 to 1/1 (v/v).

In one embodiment of the first aspect of the present invention, after adding the reducting agent, the combined solution is mixed for a period of time ranging from 4 to 24 hours. Preferably, the combined solution is then filtered to isolate the alloy catalyst.

In another embodiment of the first aspect of the present invention, the ratio of the alloy catalyst to the combination of the alloy catalyst and the solid support preferably ranges from 0.25 to 10 (w/w) %, and more preferably ranges from 0.5 to 2 (w/w) %.

In yet another embodiment of the first aspect of the present invention, the solid support solution is an aqueous slurry.

Another aspect of the present invention is directed to an alloy catalyst comprising a first metal and a second metal that are not the same, for use in oxidizing a substrate to form one or more carboxylic acids. In one embodiment the alloy catalyst is formed from the process of the first aspect of the present invention. In certain embodiments, the first metal is platinum, silver, gold, cobalt or palladium, and the second metal is molybdenum, titanium, vanadium, manganese, magnesium, iron, cobalt, nickel, copper, gold, platinum, palladium, ruthenium, iridium, or rhodium.

In certain embodiments, where the first metal is platinum, the second metal may be palladium, cobalt, iron, manganese, or copper. In an exemplary embodiment, the second metal is copper. Where the second metal is copper, the atomic ratio of platinum to copper is preferably about 1:5 to 1:1, or 1:2 to 1:4. In another embodiment the first metal is gold and the second metal is palladium. In yet another embodiment, the first metal is cobalt and the second metal is magnesium.

In certain embodiments, the alloy catalyst is a bimetallic alloy catalyst selected from the group consisting of platinum/copper, platinum/palladium, platinum/cobalt, platinum/iron, cobalt/magnesium, and gold/palladium.

In certain embodiments, the alloy catalyst is supported on a solid support. The solid support may be formed from carbon or a metal oxide. The metal oxide may contain a metal that is a lanthanide (rare earth) metal, a group 4 metal, a group 5 metal, or a group 6 metal, as set forth in *A Guide to IUPAC Nomenclature of Organic Compounds* (Recommendations 1993). Suitable metal oxides include cerium dioxide ($CeO_2$), titanium dioxide ($TiO_2$) and aluminum oxide ($Al_2O_3$).

Another aspect of the invention is directed to a process for oxidizing a substrate that includes contacting a substrate with an oxidant in the presence of an alloy catalyst to form one or more carboxylic acids. In certain embodiments, the catalyst is used to prepare one or more monocarboxylic, dicarboxylic and/or polyhydroxycarboxylic acids. In certain embodiments, the alloy catalyst formed from the process of the first aspect of the present invention is the alloy catalyst used in the oxidation process of the present invention. In certain embodiments, the alloy catalyst used in the oxidation process of the present invention is a bimetallic platinum/copper alloy catalyst.

In certain embodiments, the substrate is selected from the group consisting of sugars, polyols, furfural alcohols, and polyhydroxycarboxylic acids. In certain exemplary embodiments the substrate is a $C_3$-$C_{12}$ sugar, polyol, furfural alcohol, polyhydroxycarboxylic acid or the substrate is a $C_6$-$C_{12}$ sugar, polyol, or polyhydroxycarboxylic acid. Non-limiting examples of suitable substrates include glucose, gluconic acid, fructose, 5-hydroxymethylfurfural, furfuryl alcohol, galactose, xylose, sucrose, lactose, maltose, trehalose, glycerol, sorbitol, mannitol, lactitol, xylitol, erythritol, isomalt, maltitol, ethylene glycol, 1,3-propanediol, and 1,6-hexanediol.

Exemplary monocarboxylic acids formed by the oxidation process of the present invention may include one or more of the following: glycolic acid, glyceric acid, 3-hydroxy propionic acid, lactic acid, formic acid and furfural carboxylic acids. Exemplary dicarboxylic acids formed by the oxidation process of the present invention may include one or more of the following: glucaric acid, tartronic acid, malonic acid, oxalic acid, adipic acid, and furan dicarboxylic acid. Exemplary polyhydroxycarboxylic acids formed by the oxidation process of the present invention may include gluconic acid and xylonic acid.

In one embodiment, the temperature of the oxidation process of the present invention is maintained from about 20 to 150° C.

In one embodiment, the pressure of the oxidation process of the present invention is maintained at about 1 to 50 bar.

In certain embodiments, the concentration of the substrate in the oxidation process of the present invention is about 0.1% to 70% of the reaction mixture.

In certain embodiments, the reaction mixture of the oxidation process includes a base oxide promoter or a base metal hydroxide. Suitable base metal hydroxides include sodium hydroxide (NaOH), potassium hydroxide (KOH), cesium hydroxide (CsOH), magnesium hydroxide (Mg(OH)$_2$), calcium hydroxide (Ca(OH)$_2$), and barium hydroxide (Ba(OH)$_2$). Suitable base metal oxide promoters include calcium oxide (CaO), barium oxide (BaO), magnesium oxide (MgO), and cerium oxide ($CeO_2$).

The oxidation process may be carried out in water or a solvent. Suitable solvents include aliphatic alcohols and ketones such as methanol, ethanol, and methyl ethyl ketone.

Suitable oxidants used in the oxidation process include air, molecular oxygen ($O_2$), dilute hydrogen peroxide ($H_2O_2$), alkyl hydroperoxide, tert-butyl hydroperoxide (TBHP), and tert-amyl hydroperoxide (TAHP).

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF EXEMPLARY EMBODIMENT

Figure 1:
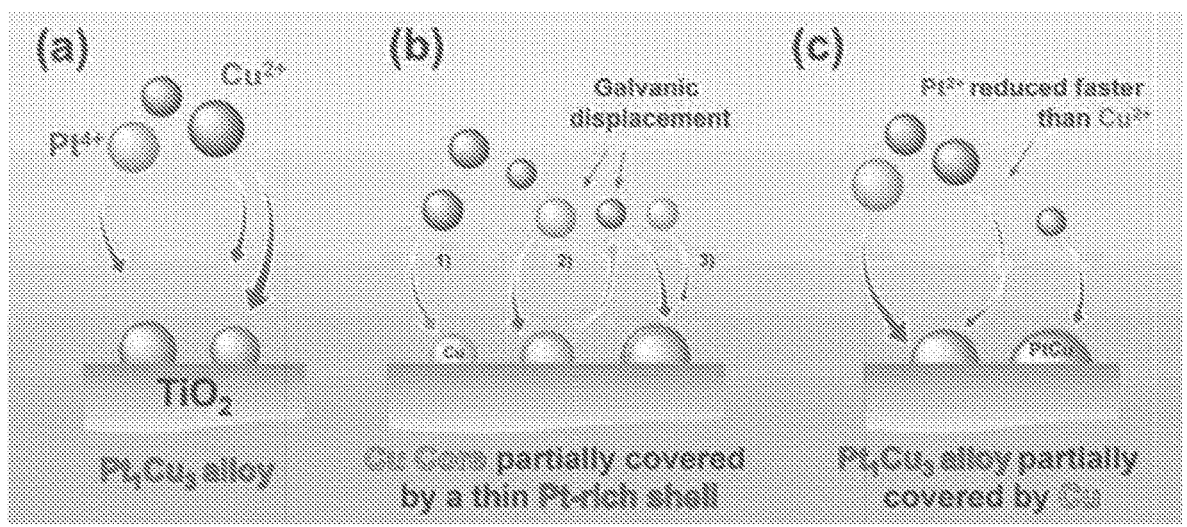
FIG. 1 is a schematic showing the syntheses of bimetallic platinum/copper catalysts with various structures.

The present invention is directed in a first aspect to a process for forming an alloy catalyst. Another aspect of the invention is directed to a process for oxidizing a substrate to form one or more monocarboxylic, dicarboxylic, and/or polyhydroxycarboxylic acids with the use of an alloy catalyst. In certain embodiments, the oxidation process uses the alloy catalyst formed from the process of the first aspect of the present invention.

I. Alloy Catalysts and Methods of Making

The alloy catalysts described herein can be formed from the process of the first aspect of the present invention and/or can be used in the oxidation process of the present invention.

The alloy catalysts include a first metal and a second metal that are not the same. Additional metals and other materials may be incorporated into the alloy catalyst consistent with the present invention. The alloy catalysts include at least two metals that are intermixed, including homogeneous mixtures, heterogeneous mixtures, and metal clusters dispersed in another metal. The alloy catalysts may include domains of a single unmixed metal and/or domains of the constituent metals mixed with other metals or additives. As is discussed in more detail below, it is thought that the intermixed structure of the alloy catalysts is responsible for their enhanced catalytic activity during the oxidation of a substrate to form one or more carboxylic acids. The oxidation process of the present invention requires lower activation energy for the formation of the one or more carboxylic acids due to the use of an alloy catalyst as opposed to a monometallic catalyst.

In certain embodiments, the alloy catalysts are nanoparticle catalysts. The nanoparticle catalysts may be less than 1 micron, preferably from 1 to 20 nm.

In one embodiment, the first metal of the alloy catalysts is selected from the group consisting of platinum, silver, gold, cobalt, and palladium. The second metal is preferably selected from the group consisting of molybdenum, titanium, vanadium, manganese, magnesium, iron, cobalt, nickel, copper, gold, platinum, palladium, ruthenium, iridium, and rhodium. In certain embodiments, the ratio of the first metal to second metal is about 1:5 to 1:1, including 1:5, 1:4, 1:3, 1:2, 1:1, and all ranges and ratios there between.

In another embodiment, the first metal is platinum and the second metal is selected from the group consisting of copper, palladium, iron, manganese, and cobalt. Where the second metal is copper, the molar ratio of platinum to copper is preferably about 1:1 to 1:5, or 1:2 to 1:4.

In another embodiment, the first metal is gold and the second metal is palladium. In another embodiment, the first metal is cobalt and the second metal is magnesium.

In certain embodiments, the alloy catalysts are supported on a solid support. The solid support preferably comprises carbon or a metal oxide. Preferred metal oxides contain a metal that is a lanthanide (rare earth) metal, a group 4, a group 5, or a group 6 metal. Of these metal oxides, titanium dioxide ($TiO_2$) cerium dioxide ($CeO_2$) and aluminum oxide are particularly suitable for use with the process of the present invention.

A process of the first aspect of the present invention comprises forming an alloy catalyst wherein a metal precursor of a first metal, a metal precursor of a second metal and a solid support are combined in a solvent to form an alloy catalyst. Preferably the metal precursors are co-precipitated to form the alloy. In one such embodiment, the process includes the following steps: forming a metal precursor solution that includes a metal precursor of a first metal and a metal precursor of a second metal; forming a solid support solution comprising a solid support and a solvent; combining the metal precursor solution and the solid support solution to form a combined solution; and adding a reducing agent to the combined solution to form the alloy catalyst.

In one exemplary embodiment of the process of the first aspect of the present invention, a metal precursor of the first metal and a metal precursor of the second metal are first dissolved in deionized water to form a first solution (a metal precursor solution). The molar concentration of the metal precursor of the first metal in the deionized water is $10^{-5}$ to $10^{-1}$ kmol/m$^3$ and more preferably $10^{4}$ to $10^{-3}$ kmol/m$^3$. The molar concentration of the metal precursor of the second metal in the deionized water is preferably $10^{-5}$ to $10^{-1}$ kmol/m$^3$, and more preferably $10^{-4}$ to $10^{-3}$ kmol/m$^3$.

A second solution (a solid support solution) is prepared that is an aqueous slurry that comprises a solid support and a solvent. Suitable solvents include but are not limited to acetonitrile, C1-C4 alcohols and other nitriles (containing the —C≡N functional group).

The first solution is added to the second solution, preferably dropwise to form a third solution (a combined solution). The ratio of the first solution to the second solution is preferably 1/100 to 200/100 (v/v), more preferably 30/100 to 200/100 (v/v), and most preferably 100/100 to 200/100 (v/v). At this stage, the concentration of each of the metal precursors in the third solution is preferably in the range of $10^{-5}$ to $10^{-1}$ kmol/m$^3$, and more preferably in the range of $10^{-4}$ to $10^{-3}$ kmol/m$^3$. The solid support is present in the third solution at a preferred concentration of 0.2 to 10.0 (g/L), and a more preferred concentration of 1.0 to 5.0 (g/L).

The third solution is then stirred for a period of time preferably ranging from 1 hour to 20 hours, and more preferably ranging from 6 hours to 12 hours. A fourth solution comprising a reducing agent dissolved in water is then added to the third solution dropwise to form a fifth solution. Preferred reducing agents include but are not limited to sodium borohydride ($NaBH_4$). The concentration of the reducing agent in the fourth solution is preferably 0.001 to 0.1 (mol/L), and more preferably 0.001 to 0.01 (mol/L). The ratio of the fourth solution to the third solution is preferably 1/5 to 1/1 (v/v). The fifth solution is then preferably stirred for a period of time preferably ranging from 4 to 24 hours. The fifth solution is filtered, washed with water, and then dried, preferably using a device such as a vacuum oven.

The ratio of the alloy catalyst to the combination of the alloy catalyst and solid support preferably ranges from 0.25 to 10 (w/w) %, and more preferably ranges from 0.5 to 2 (w/w) %.

Notably, the process of the first aspect of the present invention is a one-pot in situ method. Moreover, by tuning the preparation of an alloy catalyst as described in connection with the process of the first aspect of the present invention, one can prepare an alloy catalyst with a unique surface configuration that shows improved catalytic oxidation activity and selectivity in one-step oxidation. For example, the alloy formation can be tuned by the composition of the metal precursors used in the synthesis mixture and the temperature at which they are co-precipitated.

Although the process of the first aspect of the present invention is directed to the foregoing method of making the alloy catalyst of the present invention, the oxidation process of the present invention is directed to the use of an alloy catalyst in an oxidation reaction, wherein the alloy catalyst can be made from the process described above, other processes disclosed in the examples, or any method of making an alloy catalyst that is suitable for use in an oxidation reaction. Suitable alloy catalysts that may be made from such processes and used in the oxidation reaction include, but are not limited to platinum/copper, platinum/palladium, platinum/iron, platinum/manganese, platinum/cobalt, and cobalt/magnesium, which may be on supported on titanium dioxide, cerium dioxide, aluminum oxide or other suitable supports.

II. Oxidation Reaction

The oxidation process of the present invention comprises contacting the substrate with an oxidant in the presence of an alloy catalyst to form one or more carboxylic acids. The combination of the substrate, oxidant, alloy catalyst and in certain embodiments, optional components form one or more solutions and reaction mixtures.

The oxidation process of the present invention is carried out in a reaction vessel in which the temperature of the reaction is preferably controlled with a temperature regulating device such as a constant temperature oil bath, and the temperature of the reaction mixture may optionally be monitored during the reaction. The reaction can be carried out at very mild reaction temperatures, preferably less than 150° C., more preferably less than 100° C.

The substrate may be selected from the group consisting of sugars, polyols, furfural alcohols and polyhydroxycarboxylic acids, more preferably selected from the group consisting of $C_3$-$C_{12}$ sugars, polyols, furfural alcohols, and polyhydroxycarboxylics acids, and most preferably selected from the group consisting of $C_6$-$C_{12}$ sugars, polyols, and polyhydroxycarboxylic acids. Suitable non-limiting examples of sugars include glucose, fructose, galactose, xylose, sucrose, lactose, maltose, and trehalose. Suitable non-limiting examples of polyols include ethylene glycol, 1,3-propanediol, and 1,6-hexanediol, glycerol, sorbitol, mannitol, lactitol, xylitol, erythritol, isomalt, and maltitol. Suitable non-limiting polyhydroxycarboxylic acids include gluconic acid, and xylonic acid. Suitable furfural alcohols include 5-hydroxymethylfurfural (HMF) and furfuryl alcohol. The substrate may be harvested from readily available renewable biomass feedstocks.

A variety of carboxylic acids can be formed using the oxidation process of the present invention. Exemplary monocarboxylic acids formed by the oxidation process of the present invention may include one or more of the following: glycolic acid, glyceric acid, 3-hydroxy propionic acid, lactic acid, formic acid and furfural carboxylic acid (such as 5-hydroxymethyl-furan-2-carboxylic acid and 5-formyl-furan-2-carboxylic acid). Exemplary dicarboxylic acids formed by the oxidation process of the present invention may include one or more of the following: glucaric acid, tartronic acid, malonic acid, oxalic acid, adipic acid, and furfural dicarboxylic acid (such as 2,5-furandicarboxylic acid). Exemplary polyhydroxycarboxylic acids formed by the oxidation process of the present invention may include gluconic acid and xylonic acid.

In one aspect, the oxidation process of the present invention allows for the direct oxidation of gluconic acid, glucose, or fructose to glucaric acid and other dicarboxylic acids under mild reaction conditions. In another aspect, the oxidation process of the present invention allows for the direct oxidation of 5-hydroxymethylfurfural to 5-hydroxymethyl-furan-2-carboxylic acid, 5-formyl-furan-2-carboxylic acid and 2,5-furandicarboxylic acid.

The following paragraphs describe an exemplary process for oxidizing a substrate using an alloy catalyst of the present invention. However, other methods of using alloy catalysts in an oxidation reaction may be used consistent with the present invention.

The substrate is mixed with deionized water to form a first reaction solution, wherein the concentration of the substrate in the deionized water preferably ranges from 0.1 to 5 (mol/L).

A second reaction solution containing a base metal oxide promoter or a base metal hydroxide is then prepared. The concentration of the base metal oxide promoter or base metal hydroxide preferably ranges from 0.1 to 10 (mol/L). The base metal oxide promoter or base metal hydroxide serves to enhance the oxidation activity of the alloy catalyst. Suitable non-limiting examples of base metal oxide promoters include calcium oxide (CaO), barium oxide (BaO), magnesium oxide (MgO), and cerium oxide ($CeO_2$). Suitable non-limiting examples of base metal hydroxides include sodium hydroxide (NaOH), potassium hydroxide (KOH), cesium hydroxide (CsOH), magnesium hydroxide ($Mg(OH)_2$), calcium hydroxide ($Ca(OH)_2$), and barium hydroxide ($Ba(OH)_2$).

The volumetric ratio of the first reaction solution to the second reaction solution is preferably from 1/1 to 5/1 (v/v), and more preferably from 2/1 to 4/1.

The first and second reaction solutions may be mixed before the oxidation reaction begins, or the second reaction solution may be introduced to the reaction vessel after the oxidation reaction has already begun.

In certain embodiments where the first and second reaction solutions are mixed before the reaction begins, the combined first and second reaction solutions form a third reaction solution. The temperature of the third reaction solution may be controlled with a cooling device such as an ice bath. The alloy catalyst is then mixed with the third reaction solution to form the reaction mixture. Once the mixing of the third reaction solution is complete, it may then be added to the reaction vessel. The alloy catalyst may be added to the reaction vessel before or after the third reaction solution.

In certain embodiments where the second reaction solution is introduced to the reaction vessel after the first reaction solution and the alloy catalyst have already been added to the reaction vessel, the alloy catalyst and the first reaction solution are mixed in the reaction vessel. The second reaction solution is subsequently introduced to the reaction vessel, preferably at a controlled rate to form the reaction mixture.

The concentration of the substrate preferably ranges from about 0.1% to 70%, and more preferably ranges from about 1% to 20%. The ratio of the alloy catalyst to the substrate is preferably $10^{-8}$ to $10^{-2}$ (mol/mol) %. The reaction mixture is then heated to a preferred maintained reaction temperature that ranges from about 20 to 150° C., and more preferably about 30 to 100° C., more preferably 45 to 100° C. The pressure of the process of the present invention is preferably maintained at about 1 to 50 bar.

After the desired reaction temperature is reached, an oxidant is added or bubbled into the reaction mixture at a constant flow rate such that the oxidizer pressure is constant. Suitable oxidants include air, molecular oxygen ($O_2$), dilute hydrogen peroxide ($H_2O_2$), alkyl hydroperoxide, tert-butyl hydroperoxide (TBHP), and tert-amyl hydroperoxide (TAHP). The ratio of the flow rate of the oxidant to the volume of the reaction mixture is preferably 0.04 to 2 (mL/min·mL).

The reaction may also be carried out in a solvent. Suitable solvents include aliphatic alcohols and ketones.

The reaction results in the production of one or more dicarboxylic acids including but not limited to glucaric acid, tartronic acid, malonic acid, oxalic acid, adipic acid and furan dicarboxylic acid.

The oxidation process of the present invention results in improved yields of carboxylic acids and improved reaction rates over conventional processes. In certain embodiments, glucaric acid yields can range from 25-45%, and the total yield of dicarboxylic acids can range from 34 to 85% or higher.

The oxidation process of the present invention utilizes inexpensive oxidants, avoids byproducts, can be carried out at very mild reaction temperatures, and can be carried out as a one-pot process. The alloy catalyst of used in the oxidation process of the present invention can be easily separated from the reaction mixture at the end of the process without generating additional waste and can be reused in the process. Certain aspects of the present invention are illustrated by the following non-limiting examples.

EXAMPLES

Various bimetallic (platinum/copper, platinum/cobalt, and platinum/palladium) and monometallic (platinum, copper, and palladium) catalysts immobilized on either $CeO_2$ or $TiO_2$ solid supports were prepared.

Multiple sets of experiments were performed. In the first set of experiments, each catalyst was evaluated for its activity and selectivity in the oxidation of sodium gluconate (a product available from glucose oxidation). In the second set of experiments, three bimetallic platinum/copper catalysts were evaluated for their activity and selectivity in the oxidation of glucose. In the third set of experiments, one of the catalysts of the invention was evaluated for its activity and selectivity in the oxidation of fructose. In the fourth set of experiments, a catalyst of the invention was evaluated for its activity and selectivity in the oxidation of HMF.

All experiments were carried out in a glass semi-batch stirred reactor in which the temperature was controlled with a constant temperature oil bath. The temperature of each reaction was also monitored during the experiments. In each experiment, the oxidant used was molecular oxygen ($O_2$).

Chemicals.

The major chemicals used in preparing the catalysts used in these experiments were: $H_2PtCl_6·6H_2O$, $Pt(acac)_2$, $Cu(acac)_2$, $Pd(NO_3)_2·2H_2O$, $Cu(NO_3)_2·2.5H_2O$, Co $(NO_3)_2 \cdot 6H_2O$, $NaBH_4$, dimethyl-formamide (DMF), $CeO_2$ and $TiO_2$. All chemicals were purchased from Sigma-Aldrich.

Catalysts.

As is discussed more fully below, the alloy catalysts of the present invention generally outperformed the other monometallic and bimetallic catalysts used in the experiments. The preparation of three types of platinum/copper (PtCu) bimetallic catalysts, including the alloy catalyst of the present invention is described herein.

Although the molar ratio of copper to platinum was 3 to 1 for each of the bimetallic platinum/copper catalysts, each catalyst had a different surface morphology as shown in the synthesis schematic depicted in FIG. 1. The first catalyst (a) an alloy catalyst (platinum/copper) of the present invention, is referred to hereinafter as "PtCu-c" or "$PtCu_{alloy}$". The second catalyst (b) a bimetallic catalyst with a copper core partially covered by a thin platinum-rich shell is referred to hereinafter as "PtCu-g" or "$PtCu_{shell}$-$CU_{core}$". The third catalyst (c) a bimetallic catalyst with a bimetallic alloy core partially covered by a copper shell, is referred to hereinafter as "PtCu-s" or "$Cu_{shell}$-$PtCu_{core}$".

Alloy Catalyst Preparation (PtCu-c).

0.025 g of each metal precursor, $H_2PtCl_6 \cdot 6H_2O$, $Cu(NO_3)_2 \cdot 2.5H_2O$, were dissolved in 150 mL of deionized water, which was then added dropwise to a 300 mL aqueous slurry with 1.2 of $TiO_2$ and 30 mL of acetonitrile. The concentration of precursors in the combined slurry was in the range of about $1.36 \times 10^{-4}$-$1.44 \times 10^{-3}$ $kmol/m^3$. After stirring for two hours, 0.2 g of sodium borohydride ($NaBH_4$) in 50 mL water was introduced to the slurry dropwise, after which the whole mixture was stirred overnight for about 16-20 hours. The whole mixture was subsequently filtered, washed with water, and dried in a vacuum oven. The Pt and Cu metal content on solid supports was in the range of about 1.3 to 2.2 w % as determined by inductively coupled plasma mass spectrometry (ICP-MS) analysis.

Bimetallic Catalyst with Copper Core Partially Covered by Thin Platinum-Rich Shell (PtCu-g).

Following the procedures set forth with respect to PtCu-c, $Cu(NO_3)_2 \cdot 2.5H_2O$ was first dissolved in 75 mL of deionized water. $TiO_2$ was added to 300 mL of water and stirred to form a $TiO_2$ slurry. The $Cu(NO_3)_2 \cdot 2.5H_2O$ solution was then added dropwise to the $TiO_2$ slurry. Next, 0.1 g of sodium borohydride ($NaBH_4$) in 25 mL of deionized water was slowly added. After 4 hours, 75 mL of $H_2PtCl_6 \cdot 6H_2O$ solution was added dropwise. Next, 0.1 g of sodium borohydride ($NaBH_4$) in 25 mL of deionized water was again added to the solution. The mixture was then stirred for an additional 3 hours before the solid catalysts were filtered.

Bimetallic Catalyst with Bimetallic Alloy Core Partially Covered by a Copper Shell (PtCu-s).

20 g of dimethylformamide (DMF) and 0.05 g of Pt(acac)$_2$ and 0.05 g of Cu(acac)$_2$ were mixed with 1.2 g of $TiO_2$ solid support and introduced into an autoclave. The mixture was heated to 200° C. and stirred for 24 hours before the sample was taken out, filtered, and washed with water/ethanol (1/1 vol/vol).

All catalyst samples were dried in a vacuum oven before performing the activity tests.

Two turn over frequencies ("TOF") values were defined to evaluate the catalyst performances, one based on the bulk composition of Pt metal content and the other based on surface Pt metal content, both calculated at low conversion levels (4-22%). For kinetic analysis, TOF based on surface metal composition was considered. Mass balance (C %) is defined as the ratio of total carbon detected in the product mixture to total carbon initially charged in the reaction medium.

Example 1: Oxidation of Sodium Gluconate with Pt/Cu Catalysts

Catalyst Activity Tests Using Sodium Gluconate as the Substrate.

Figure 14:
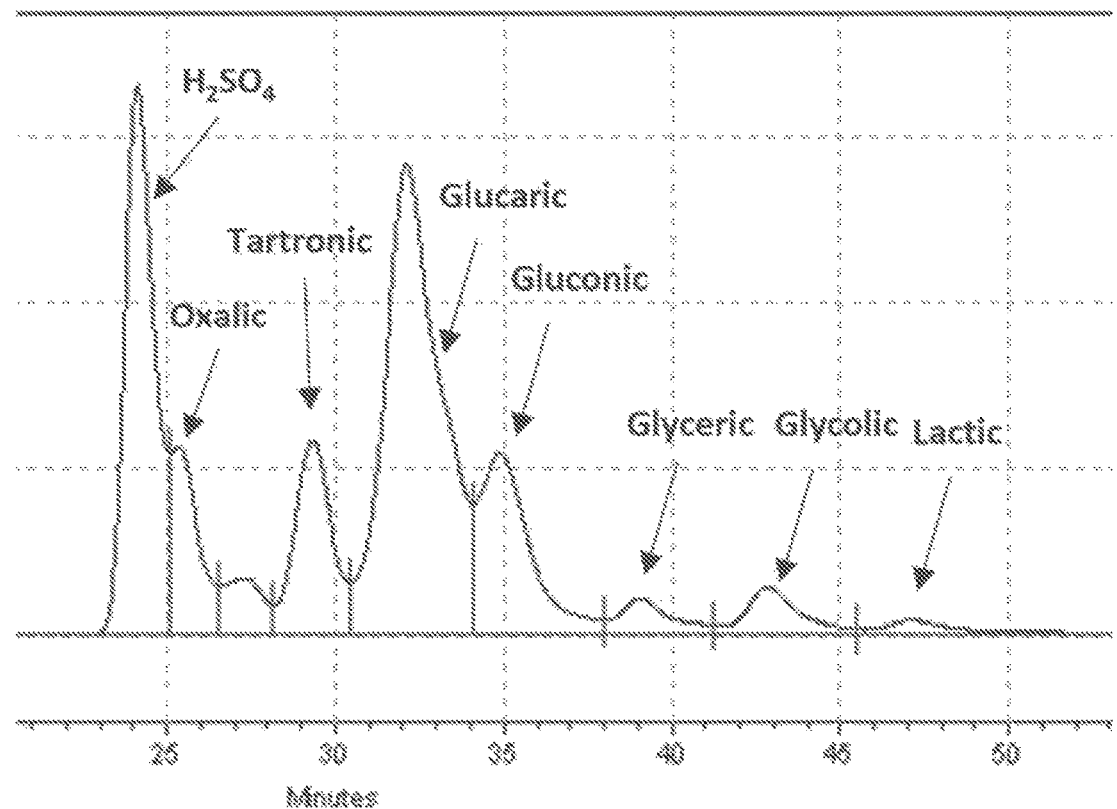
FIG. 14 shows a liquid chromatograph result from sodium gluconate oxidation.

For each experiment using sodium gluconate as the substrate, 3 grams of sodium gluconate was first mixed with 25 mL of deionized water, which was then mixed with a sodium hydroxide (NaOH) solution of 0.04 g/mL in an ice bath. Next, 0.1 grams of the solid catalyst samples (loading: 2 w % or 2 w-w %) were added to the glass semi-batch stirred reactor. Finally, the combined sodium gluconate and sodium hydroxide solutions were added to the reactor. The catalyst and substrate mixture was heated to the targeted reaction temperature (60.0° C.) and after thermal equilibrium was attained, oxygen ($O_2$) was bubbled into the solution continuously at a constant flow rate such that the oxygen ($O_2$) pressure was constant. The results of these experiments are summarized in Table 1 below. Referring to Table 1 below, the total reaction time was six hours for Experiment Nos. 1-10 and four hours for Experiment 11. During the reaction, small amounts of samples (0.5 mL) were taken from the reaction mixture and analyzed by high-performance liquid chromatography (HPLC) using the following analytic conditions: Liquid products were analyzed by Shimadzu HPLC with a Shodex SH1011 column and (1) 0.005 N $H_2SO_4$ in aqueous solution as the mobile phase, (2) 70° C. of column temperature and (3) 60 minutes of analysis time. Results are shown in FIG. 14.

TABLE 1

Comparison of mono and bimetallic catalysts for sodium gluconate oxidation

| # | Catalyst | X (%) | S (%) Glucaric | Tartronic | Oxalic | Others | C (%) |
|---|----------|-------|----------------|-----------|--------|--------|-------|
| 1 | Pt/CeO$_2$ | 28.0 | 47.0 | 31.1 | 6.4 | 15.6 | 100.1 |
| 2 | Pt/TiO$_2$ | 70.8 | 38.1 | 27.7 | 5.8 | 11.5 | 83.1 |
| 3 | Pd/CeO$_2$ | 50.7 | 36.9 | 27.3 | 10.9 | 15.7 | 90.8 |
| 4 | Pd/TiO$_2$ | 41.1 | 44.2 | 28.3 | 8.3 | 11.5 | 92.3 |
| 5 | Cu/CeO$_2$ | 1.6 | 28.9 | 31.2 | 11.2 | 19.3 | 90.6 |
| 6 | Cu/TiO$_2$ | 2.8 | 31.2 | 30.0 | 9.9 | 21.1 | 90.4 |
| 7 | Co/CeO$_2$ | 5.5 | 21.8 | 38.9 | 15.6 | 15.3 | 91.6 |
| 8 | PtCu/CeO$_2$ | 72.4 | 32.2 | 23.6 | 6.6 | 15.8 | 78.2 |
| 9 | PtCo/CeO$_2$ | 50.7 | 36.6 | 27.3 | 10.9 | 18.0 | 92.8 |
| 10 | PtPd/CeO$_2$ | 41.1 | 36.7 | 28.2 | 10.0 | 14.7 | 89.6 |
| 11* | PtCu/TiO$_2$ | 100 | 32.3 | 27.2 | 19.5 | 11.1 | 91.8 |

X: conversion, S: selectivity, C %: carbon balance, others: glyceric, glycolic, and formic acids.

It was found that the Pt catalysts (Experiment Nos. 1 and 2) outperformed other monometallic Pd, Cu, and Co catalysts (Experiment Nos. 3-7) in terms of either conversion and/or glucaric acid selectivity. The major oxidation products formed from sodium gluconate oxidation were glucaric acid, tartronic acid, and oxalic acid. Other products formed during each reaction included monocarboxylic acids such as glyceric acid, lactic acid, glycolic acid, and formic acid.

It was further found that of the bimetallic catalysts, the platinum/copper alloy catalysts (Experiment Nos. 8 and 11) exhibited better performances as compared to the platinum/palladium and platinum/cobalt bimetallic catalysts (Experiment Nos. 9 and 10). It was further found that titanium dioxide (TiO$_2$) (Experiment Nos. 2, 4, 6, and 11) showed better overall promotional effect for oxidation as compared to cerium dioxide (CeO$_2$) (Experiment Nos. 1, 3, 5, 7, and 8-10). For these reasons, the bimetallic platinum/copper catalysts supported on titanium dioxide (TiO$_2$) were chosen for further experimentation on the oxidation of glucose, described in Example 2, below.

Figure 2:
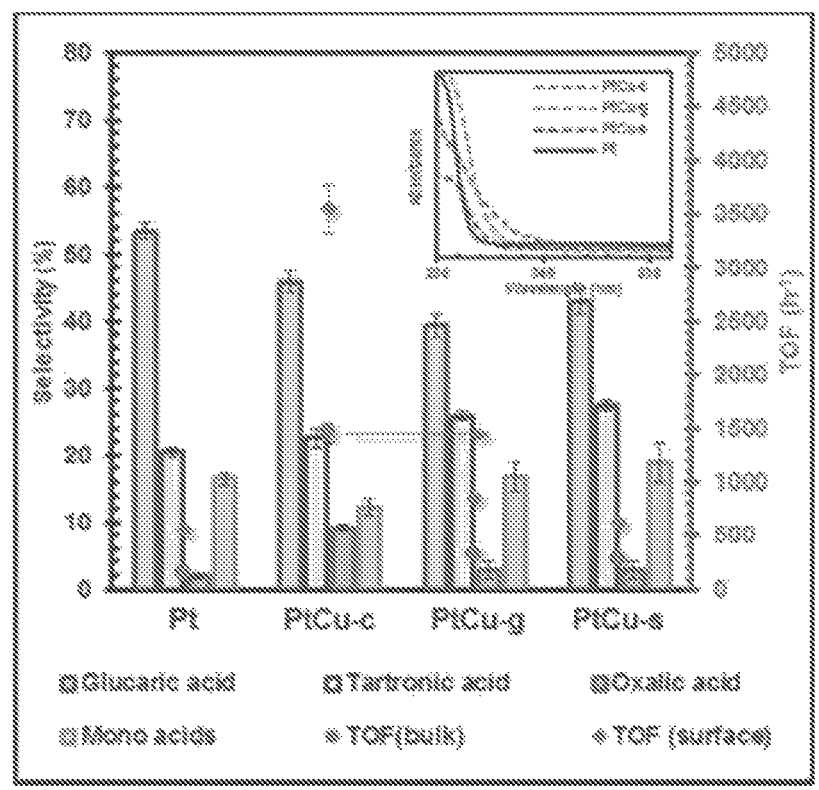
FIG. 2 shows the activity and product distribution of $TiO_2$-supported platinum and platinum/copper catalysts.
Figure 13:
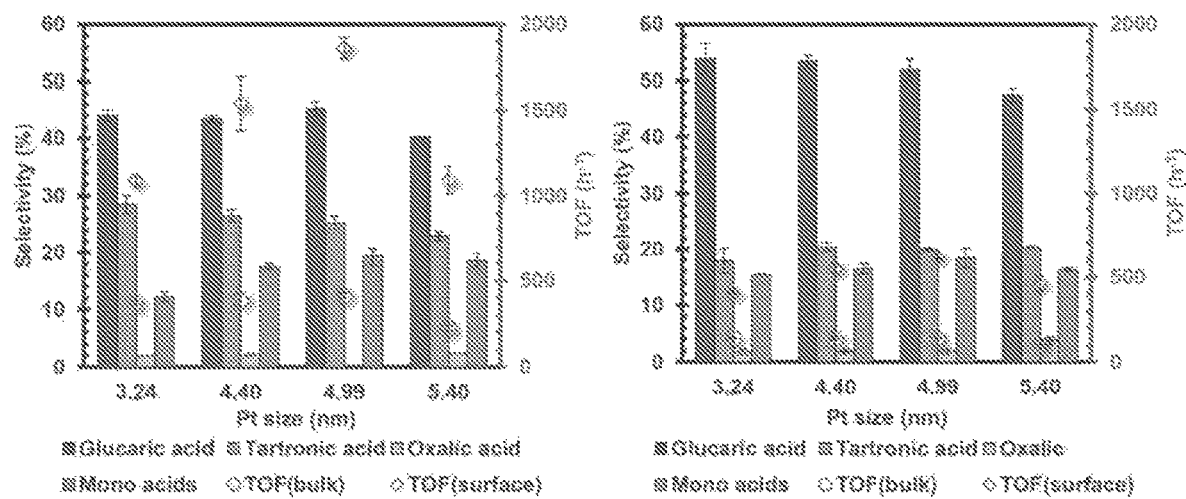
FIG. 13 shows activity and selectivity of Pt/$TiO_2$ catalysts at 60° C. and 45° C.

Catalytic oxidation experiments with the platinum/copper bimetallic catalysts (PtCu-c, PtCu-g, and PtCu-s) as well as the Pt/TiO$_2$ and Cu/TiO$_2$ catalysts were performed using the following reaction conditions: 3 g sodium gluconate, 0.1 g solid catalyst, 0.5 w %, 0.5 w-0.5 w % metal loading, 1.0 g NaOH, 45° C. and 0.1 MPa O$_2$, sodium gluconate conversion=4-22%, reaction time: 0.5-1.5 hours. Data regarding such catalysts are presented in FIGS. 2, 3, and 4. While the monometallic catalysts, Pt/TiO$_2$ and Cu/TiO$_2$ showed TOF of 550±31.7 and 13.2±4.3 h$^{-1}$ respectively, the alloy PtCu-c catalyst exhibited remarkably higher TOF (3,542.9±221.1 h$^{-1}$) and higher combined selectivity (82%) towards glucaric acid (46%), tartronic acid (24%), and oxalic acid (12%) at 45° C. and 0.1 MPa O$_2$ pressure. Results for the bimetallic catalysts are shown in FIG. 2. Results for monometallic catalysts are shown in FIG. 13 at 60° C. (left) and 45° C. (right) (conversion 3-17%).

The experimental results shown in FIG. 2 demonstrate that the catalytic performances were sensitive to surface morphologies of platinum nanoparticles. Gluconic acid, tartronic acid, oxalic acid and monoacids are depicted in the bars from left to right for each catalyst. Therefore, surface characterization using transmission electron microscopy ("TEM"), scanning electron microscope ("SEM"), ultraviolet-visible spectrophotometry ("UV-Vis") and chemisorption was performed, and the results are shown in Table 2 below.

TABLE 2

| | BET and Chemisorption Data | | | |
|---|---|---|---|---|
| Catalyst | Size from TEM (nm) | Size from H$_2$ sorption (nm) | Pt content w % (ICP) | Cu content w % (ICP) |
| Pt | 4.99 | 5.43 | 0.52 | — |
| Pt$_1$Cu$_1$-c | 4.14 | 4.55 | 0.54 | 0.13 |
| Pt$_1$Cu$_2$-c | 4.16 | 4.68 | 0.43 | 0.32 |
| Pt$_1$Cu$_3$-c | 4.02 | 4.21 | 0.48 | 0.51 |
| Pt$_1$Cu$_{3.5}$-c | 4.98 | 5.84 | 0.58 | 0.69 |
| Pt$_1$Cu$_3$-g | 4.40 | 6.51 | 0.49 | 0.59 |
| Pt$_1$Cu$_3$-s | 3.84 | 4.59 | 0.55 | 0.51 |

Properties of catalyst support: TiO$_2$ support used has a very low surface area (4.9 m$^2$/g) with <5 micrometers and 4.17 g/mL.

Figure 3:
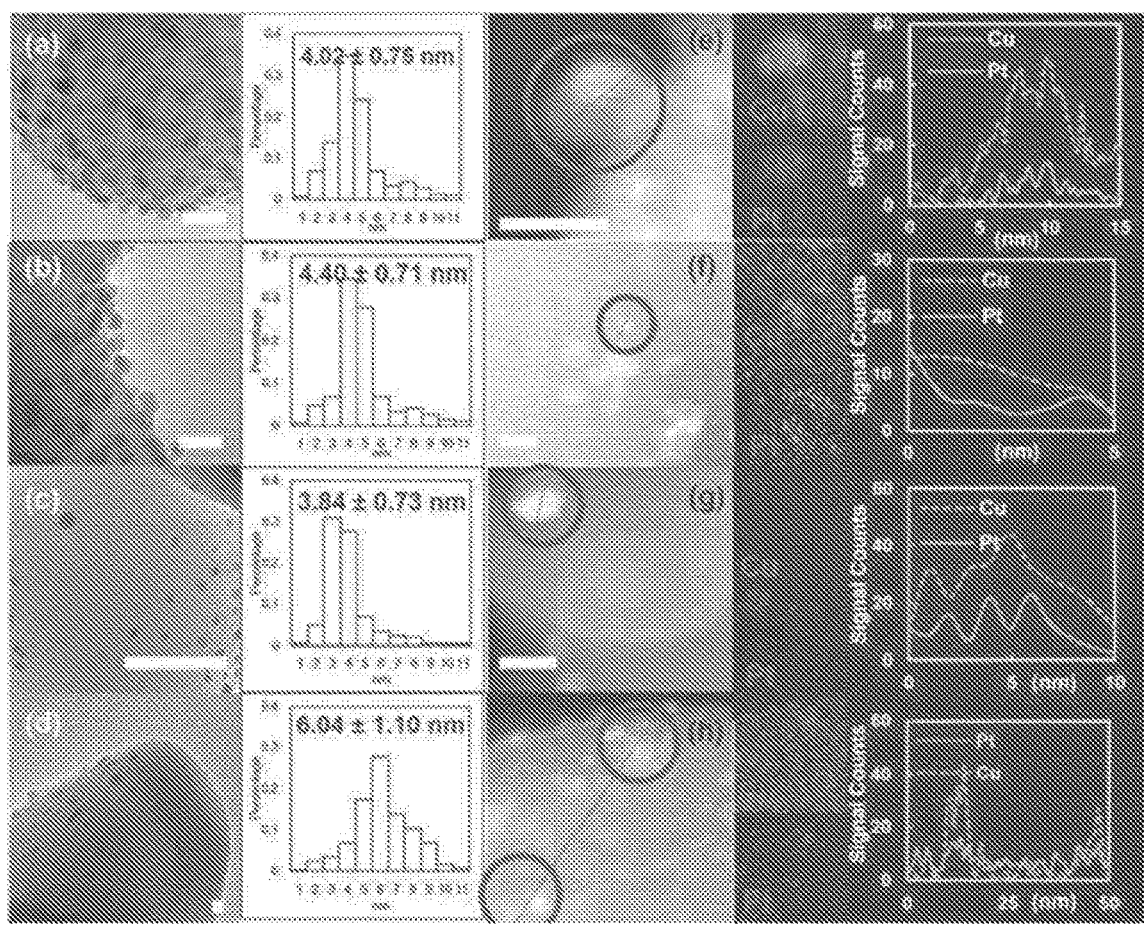
FIG. 3 is the HR-TEM, STEM, and EDX Mapping of PtCu-c, PtCu-g, PtCu-s and spent PtCu-c catalysts.
Figure 5:
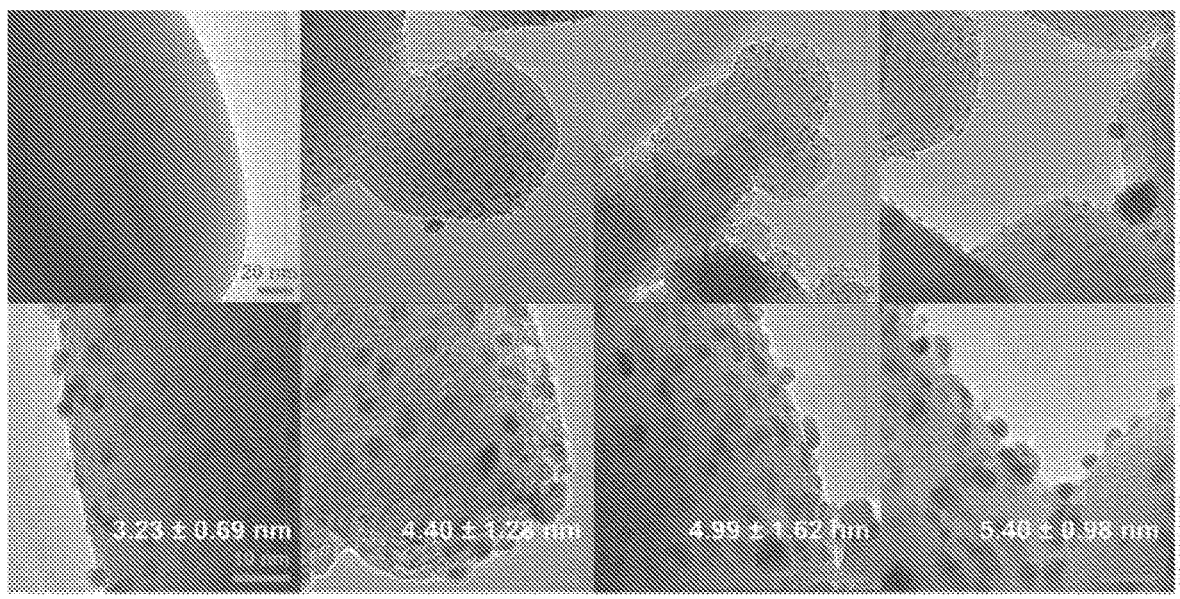
FIG. 5 shows TEM Images of Monometallic Pt/$TiO_2$ Catalysts.
Figure 12:
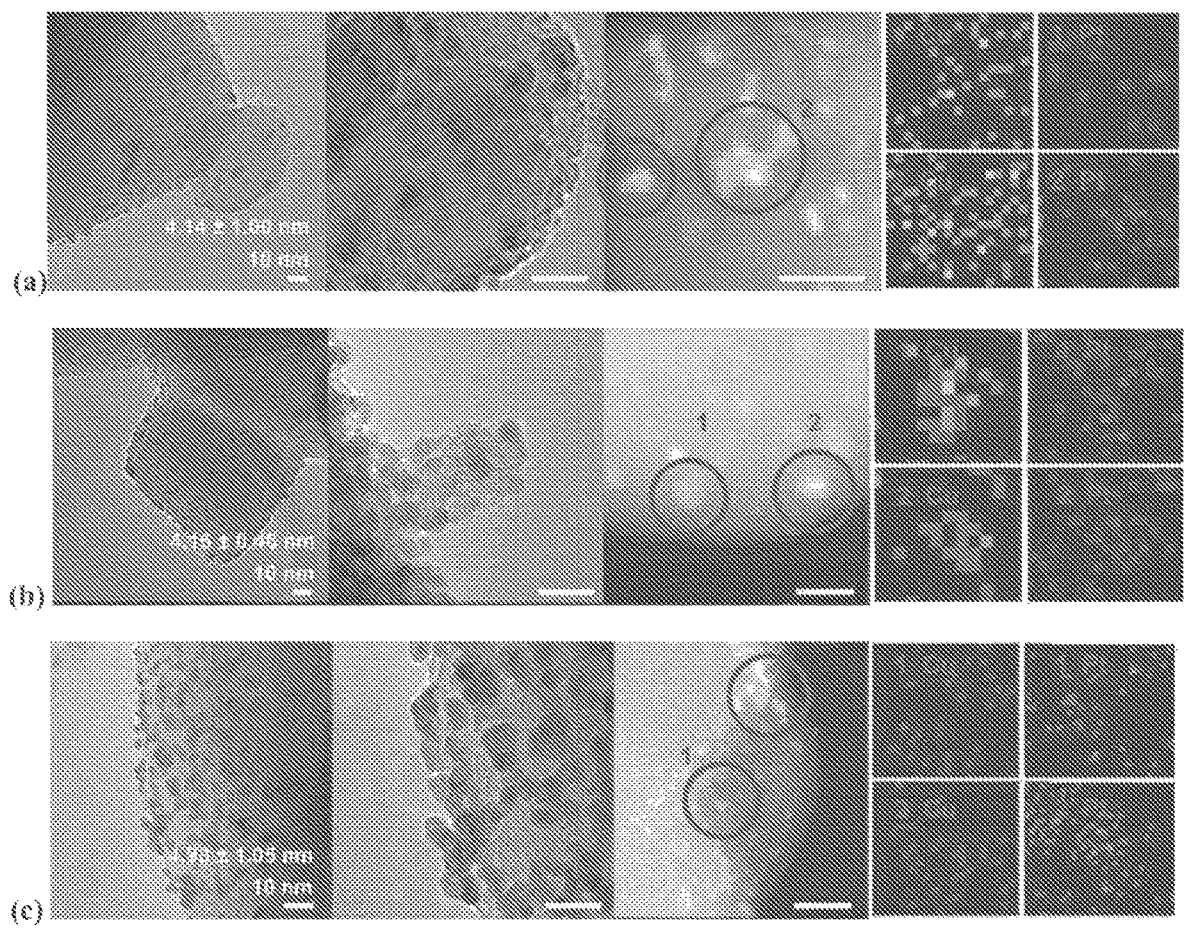
FIG. 12 shows TEM characterization of bimetallic PtCu nanoparticles on $TiO_2$ support.

FIG. 3 shows the HR-TEM, STEM and EDX Mapping of (a) PtCu-c, (b) PtCu-g, (c) PtCu-s and (d) spent PtCu-c (after 3$^{rd}$ recycle) catalysts and EDX spectrum of metal particles on (e) PtCu-c, (f) PtCu-g, (g) PtCu-s and (h) spent PtCu-c (after 3$^{rd}$ recycle) catalysts (while or black bar indicates 10 nm linear dimension. FIG. 5 shows the TEM characterization of monometallic PtTiO$_2$ catalysts. Monometallic particles with a 4.99 nm in size displayed the highest activity for sodium gluconate oxidation and were chosen for detailed studies for performance comparison and reaction profiles. FIG. 12 shows the TEM characterization of bimetallic PtCu nanoparticles on TiO$_2$ support (a) PtCu-c (1:1), (b) PtCu-c (1:2), (c) PtCu-c (1:3.5).

High-resolution transmission electron microscopy ("HR-TEM") images (see FIGS. 3(a-c)) on the bimetallic platinum/copper catalysts (PtCu-c, PtCu-g and PtCu-s) confirmed that each possessed unique bimetallic structures on the surface of the titanium dioxide (TiO$_2$) supports. It was found that the size of each of the bimetallic platinum/copper particles was in the range of about 3.84-4.40 nm, which was slightly smaller than the monometallic platinum particles having the same Pt loading (about 4.99 nm as shown FIG. 5).

Figure 6:
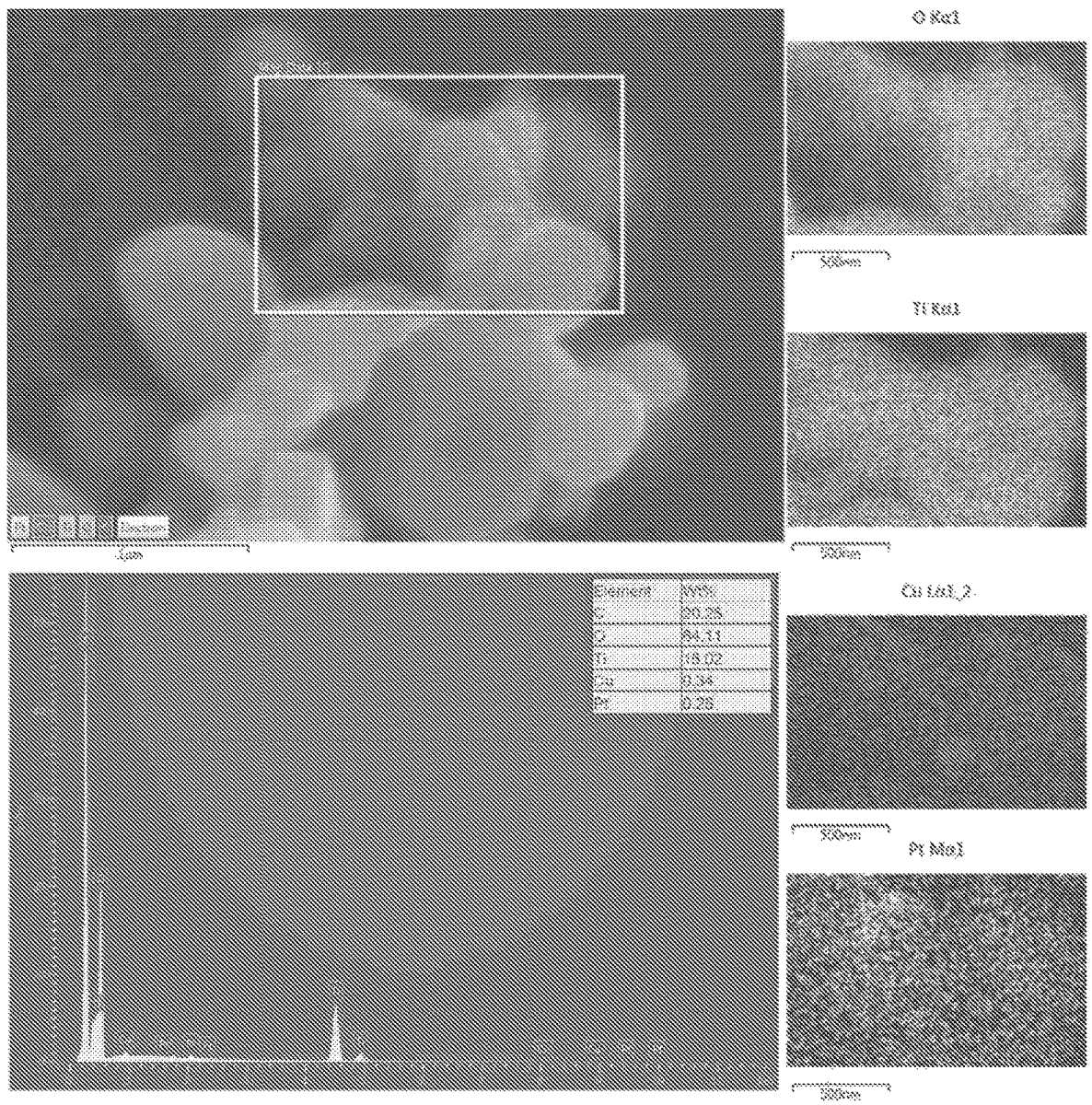
FIG. 6 shows SEM Images of PtCu-c (1:3) sample.
Figure 7:
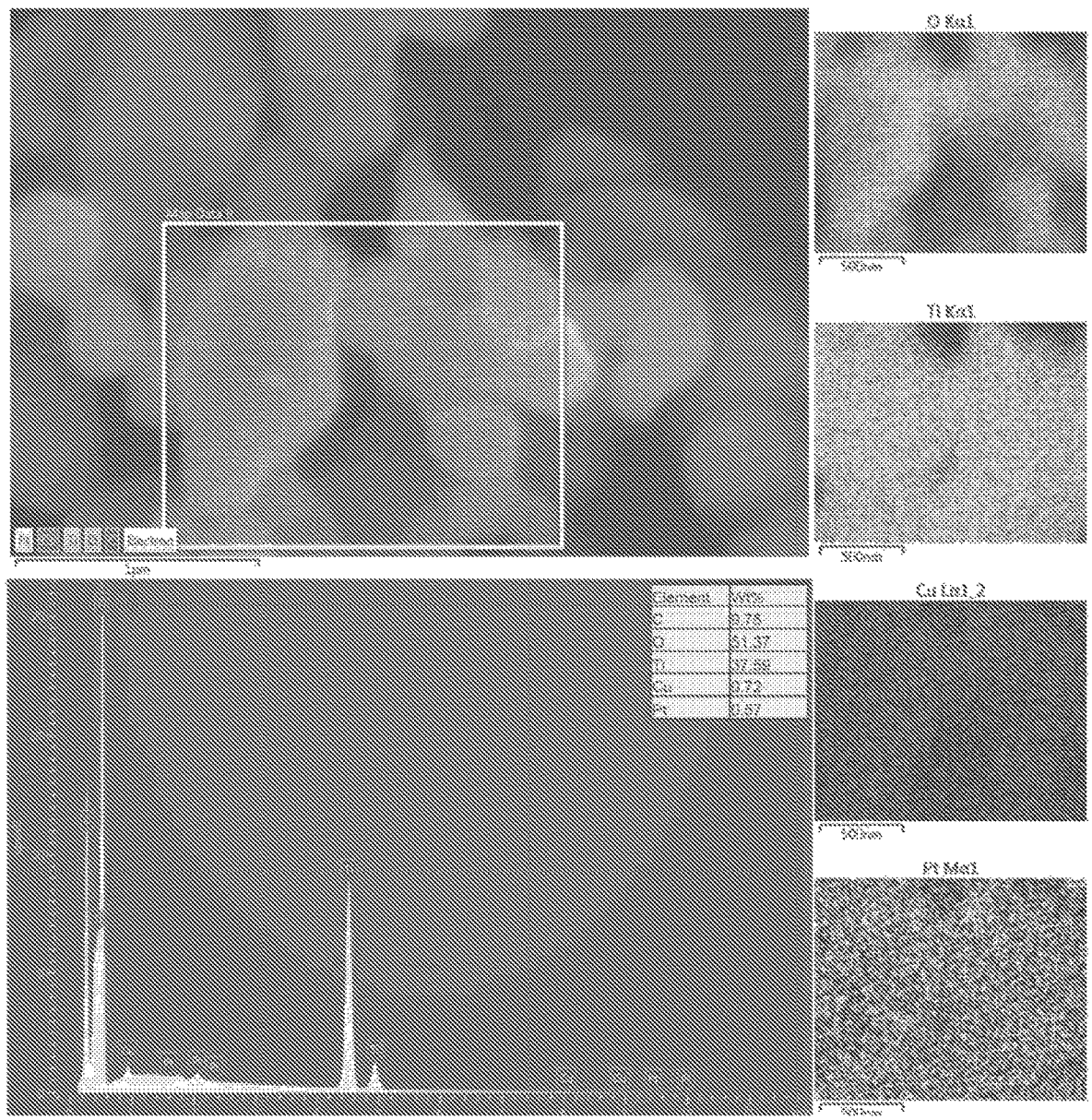
FIG. 7 shows SEM Images of PtCu-g (1:3) sample.
Figure 8:
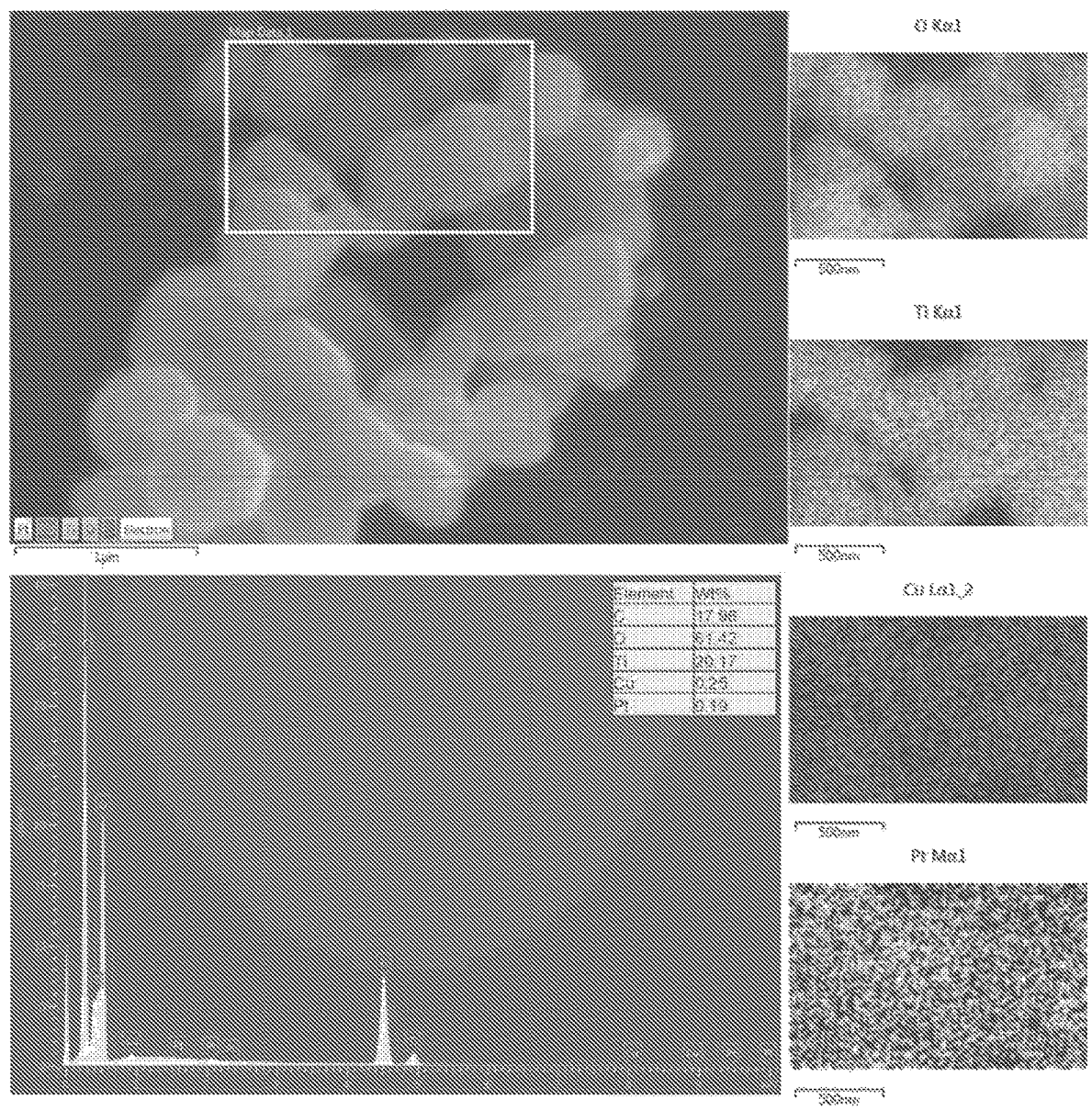
FIG. 8 shows SEM Images of PtCu-s (1:3) sample.

This means that the presence of copper actually favored the dispersion of the platinum species. Energy-dispersive x-ray ("EDX") mapping and spectrum (FIGS. 3(e-g)) of selected regions from scanning transmission electron microscopy ("STEM") revealed that, as described above, the respective particle morphologies for PtCu-c, PtCu-g and PtCu-s are (i) alloy, (ii) copper-rich core, and (iii) platinum-rich core, respectively. FIGS. 6-8 show SEM surface composition analysis of PtCu-c (FIG. 6), PtCu-g (FIG. 7) and PtCu-s (FIG. 8), having a 1:3 Pt:Cu ratio. The PtCu-c nanoparticles were in alloy form due to the co-reduction of both Pt$^{4+}$ and Cu$^{2+}$ ions in the presence of titanium dioxide (TiO$_2$) support.

The surface morphology of the PtCu-g sample was due to the fact that Pt$^{4+}$ ions were introduced after copper nanoparticles were formed. The displacement reaction between Pt$^{4+}$ ions and copper generates metallic Pt and Cu$^{2+}$, which could have led to the displacement of copper species from nanoparticles. However, due to the presence of reducing agents in aqueous solution, the Cu$^{2+}$ species were reduced back on the existing nanoparticle surface, resulting in the formation of structures with a platinum-rich shell and a copper-rich core.

The synthesis of PtCu-s via the solvothermal method outlined above caused the faster reduction rate of Pt$^{2+}$ as compared to Cu$^{2+}$. This favored the formation of a platinum-rich core structure on the titanium dioxide (TiO$_2$) solid support. Detailed inspections of particle size and lattice parameter confirmed that Pt surface plane (the thermodynamically most stable form), was the dominant phase in these samples, while this characteristic was not obvious for the monometallic Pt catalysts (see FIG. 6).

Figure 2A:
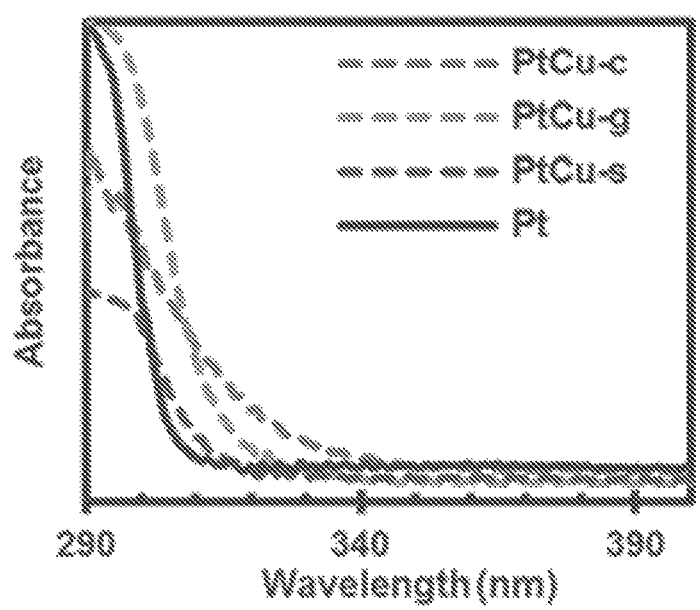
FIG. 2(a) is an enlarged view of the insert of FIG. 2, and shows UV-Vis spectra of Pt, PtCu-c, PtCu-g, and PtCu-s catalysts.
Figure 9:
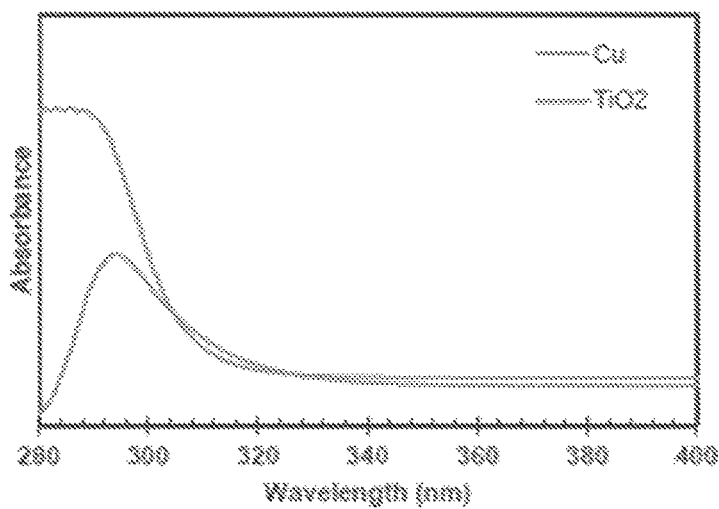
FIG. 9 shows UV-vis spectra of Cu/$TiO_2$ samples.

UV-Vis spectra of the prepared monometallic platinum and bimetallic platinum/copper nanocatalysts were also obtained to further understand the structures of these catalysts, and results are shown in FIG. 2(a). The monometallic platinum catalyst is shown in the solid black line, PtCu-s is depicted by the darkest dashed line, beginning near the middle of the x axis. PtCu-c is depicted by the dashed line beginning on the x axis above PtCu-s. PtCu-g is depicted by the dashed line beginning at the top of the x axis. Since the metal loading only accounted for 1% of the total catalyst weight, the characteristic absorption of the titanium dioxide (TiO$_2$) solid support (about 300 nm wavelength) was dominant in all UV-Vis spectra. However, the shift of absorption peaks indicates plasmon characteristics of metal nanoparticles on the surface of the titanium dioxide (TiO$_2$) solid support. Referring again to FIG. 2(a), the onset of UV-Vis absorption for Pt was around 305-310 nm, which was similar to the value observed for Cu/TiO$_2$ and TiO$_2$ support (300-310 nm) as shown in the UV-vis spectra of Cu/TiO$_2$ sample of FIG. 9 (with TiO$_2$ beginning at the bottom of the x axis and Cu near the top). This implies that plasmon absorption on the surface of the monometallic platinum catalysts supported on titanium dioxide (Pt/TiO$_2$) was insignificant.

The onset of UV-Vis absorption of the bimetallic platinum/copper catalyst samples was, however, found to be very different. In particular, the absorption peaks of the PtCu-s and PtCu-g catalysts were shifted to about 315-325 nm, while the PtCu-c catalyst—the most active catalyst—displayed a much higher bandgap at greater than 340 nm. The red shift of wavelength indicates that the alloy catalyst (PtCu-c) nanoparticles exhibited plasmon absorption while the surface of monometallic platinum catalysts do not show obvious plasmon adsorption on titanium dioxide ($TiO_2$) solid supports. In addition, recent experimental work on platinum/copper systems as well as density functional theory (DFT) predictions have indicated that the presence of adjacent copper species often lowers the binding energy with oxygen containing groups on the surface of platinum catalysts. Taking into account the different catalytic activity of platinum and platinum/copper catalysts for carbon-oxygen bond activation during oxidation reactions, it appears that the unique alloy catalyst structure is responsible for the remarkable enhancement of catalytic activity during the oxidation of sodium gluconate.

Figure 11:
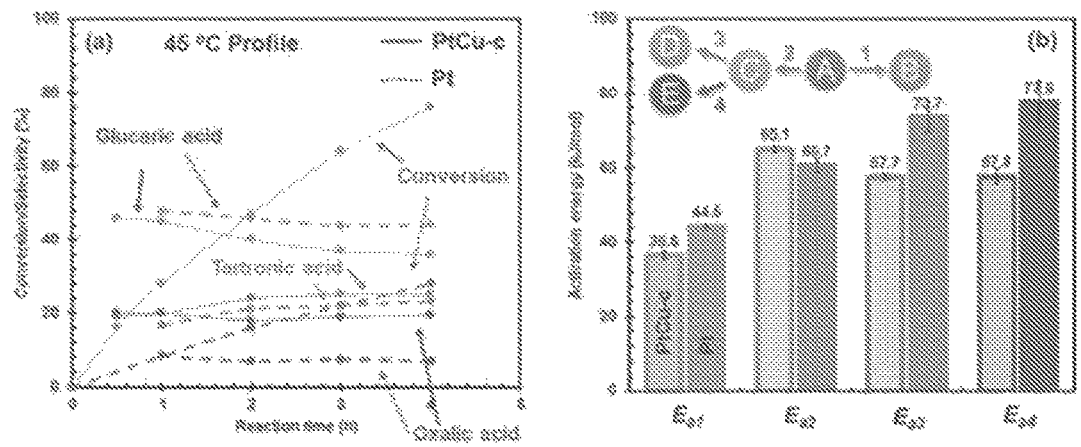
FIG. 11 shows (a) temporal reaction profiles for $Pt_1Cu_3$-c/$TiO_2$ and Pt/$TiO_2$ catalysts at 45° C.; and (b) calculated activation energy based on 45-70° C. experimental rate data.

11(a) shows temporal reaction profiles for $Pt_1Cu_3$-c/$TiO_2$ and Pt/$TiO_2$ catalysts at 45° C.; and FIG. 11(b) shows calculated activation energy based on 45-70° C. experimental rate data. Other reaction conditions were as described with respect to FIG. 2. As shown in FIG. 11(b), a reaction network involving the oxidation of sodium gluconate (A) to glucaric acid (B, r1), C—C cleavage of gluconate to mono carboxylic acids (C, r2), tartronic (D, r3) and oxalic (E, r4) was proposed. The specific reaction rates of sodium gluconate and product formation rates were determined for the two catalysts from the concentration-time profiles. Corresponding rate constants (shown in Table 3 below) were calculated assuming pseudo first order kinetics with respect to sodium gluconate and NaOH (with molecular $O_2$ in excess). The estimated apparent activation energies for r1-r4 on both catalysts are listed in FIG. 11(b).

TABLE 3

| | | Activation Energy on Mono and Bimetallic Pt catalysts | | | |
|---|---|---|---|---|---|
| | rate | Temperature | | | $E_a$ |
| Catalyst | constant | 45° C. | 60° C. | 70° C. | (kJ/mol) |
| $Pt_1Cu_3$ | k1 | 40.82 ± 4.34 | 82.2 ± 11.59 | 110.6 ± 11.4 | 36.6 ± 0.94 |
| | k2 | 7.16 ± 0.99 | 17.6 ± 4.80 | 35.62 ± 0.27 | 57.7 ± 0.84 |
| | k3 | 1.92 ± 0.23 | 4.63 ± 0.89 | 9.70 ± 0.50 | 57.8 ± 2.15 |
| | k4 | 5.47 ± 1.87 | 16.06 ± 3.52 | 33.12 ± 3.98 | 65.1 ± 0.70 |
| Pt | k1 | 5.41 ± 0.43 | 12.31 ± 1.13 | 16.61 ± 0.15 | 44.5 ± 0.44 |
| | k2 | 2.06 ± 0.05 | 7.47 ± 0.48 | 15.62 ± 0.27 | 73.7 ± 0.74 |
| | k3 | 0.19 ± 0.03 | 0.63 ± 0.15 | 1.70 ± 0.20 | 77.8 ± 5.44 |
| | k4 | 1.67 ± 0.19 | 4.96 ± 0.65 | 8.86 ± 1.38 | 60.7 ± 1.82 |

Figure 4:
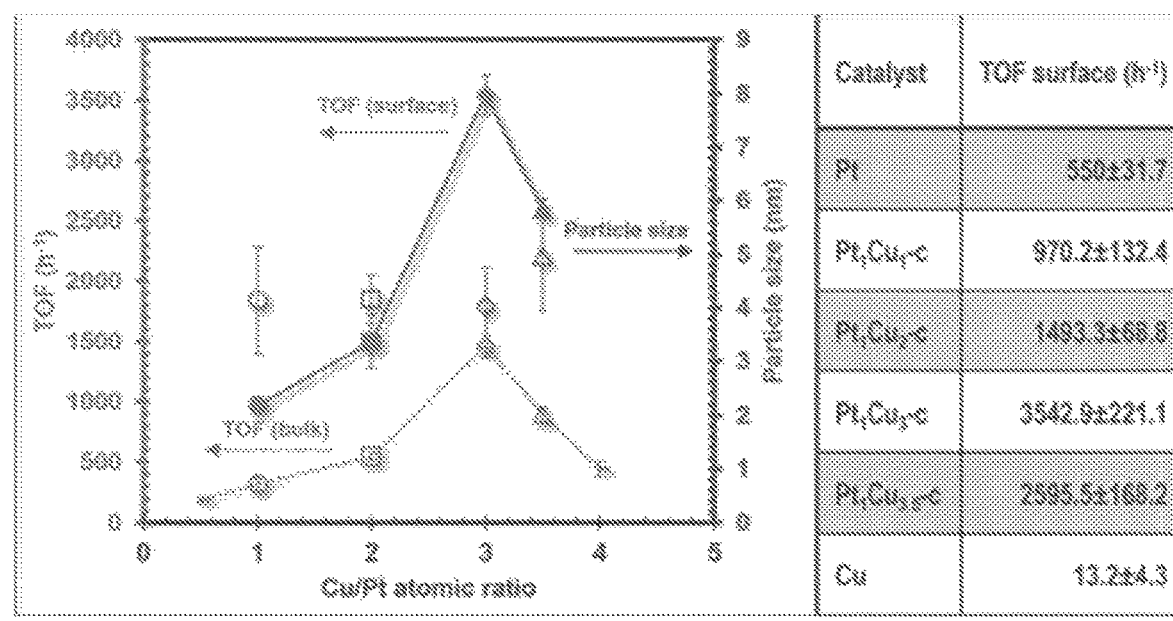
FIG. 4 shows the effect of copper/platinum ratio in $Pt_1Cu_x$-c samples on catalytic activity during oxidation of sodium gluconate.

The effect of the atomic ratio of copper to platinum of the bimetallic platinum/copper alloy catalyst (PtCu-c) on catalytic activity and product selectivity was also studied to understand the synergistic effects on catalytic performance. PtCu-c samples with various atomic ratios of copper to platinum were prepared and evaluated for the oxidation of sodium gluconate and the results are reported in FIG. 4. Reaction conditions were the same as described with respect to FIG. 2. Synergistic effects were found where the atomic ratio of copper to platinum ranged from about 1:1 to 4:1. In particular, the TOF (surface) for $Pt_1Cu_1$-c (copper to platinum atomic ratio of 1:1), $Pt_1Cu_2$-c (copper to platinum atomic ratio of 2:1), $Pt_1Cu_3$-c (copper to platinum atomic ratio of 3:1) and $Pt_1Cu_{3.5}$-c (copper to platinum atomic ratio of 3.5:1) catalysts were 970.2±132.4, 1,493.3±68.8, 3,542.9±221.1 and 2,595.5±168.2 $h^{-1}$, respectively. As shown in FIG. 4, these values were all significantly higher than those obtained with individual platinum and copper catalysts under the same reaction conditions. Increasing the atomic ratio of copper to platinum did not seem to cause the bimetallic platinum/copper alloy particle size to increase until the atomic ratio of copper to platinum is greater than 3:1. This observation was consistent with a slightly reduced TOF for the $Pt_1Cu_{3.5}$-c catalyst.

Figure 10:
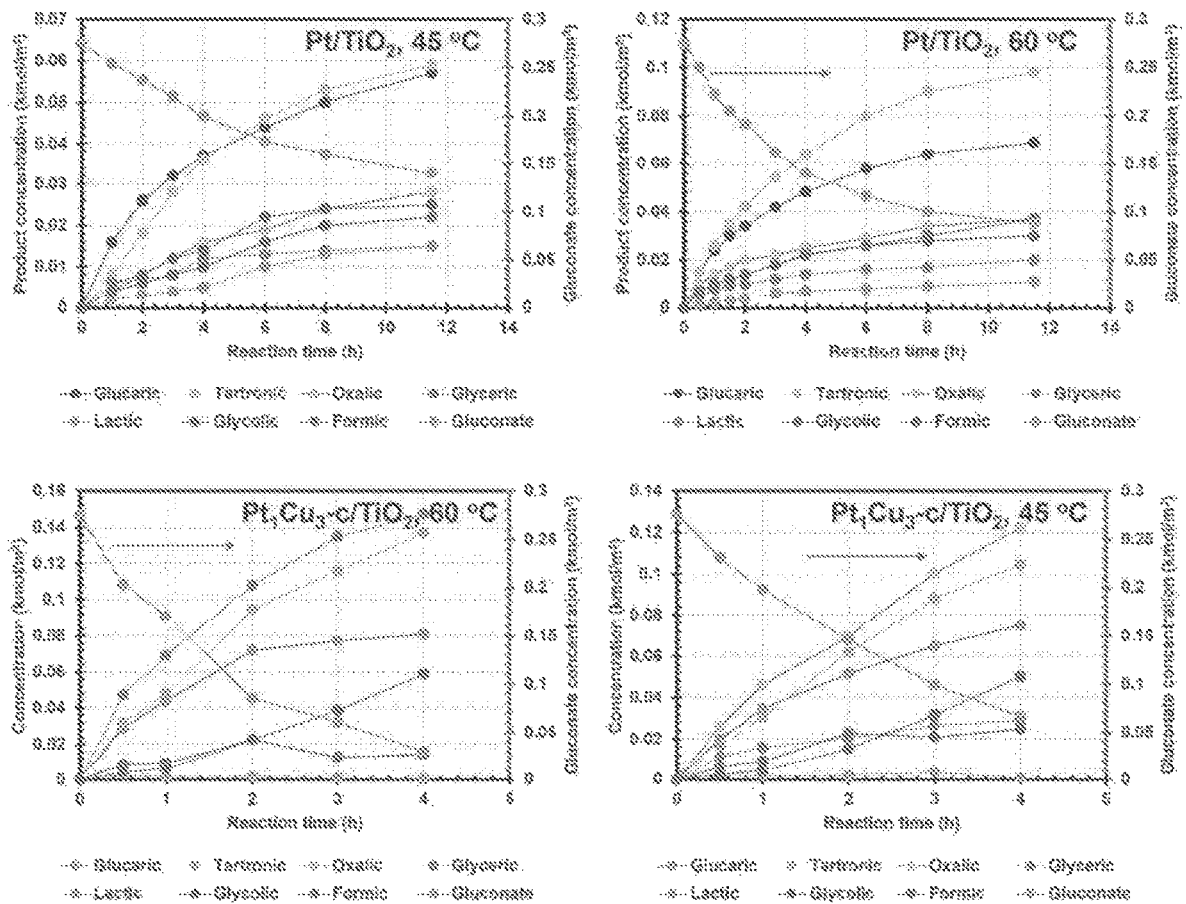
FIG. 10 shows concentration versus time profiles of sodium gluconate oxidation on monometallic and bimetallic catalysts at 45° C. and 60° C.

Since the presence of copper species synergistically enhanced the catalytic activity of platinum catalysts, the effect of copper on the kinetic behavior of platinum catalysts was also investigated. For this purpose, concentration-time profiles were obtained in a semi-batch reactor at different temperatures (from 45 to 70° C.) using both monometallic platinum supported on titanium dioxide (Pt/$TiO_2$) and bimetallic platinum/copper alloy catalysts supported on titanium dioxide ($Pt_1Cu_3$-c). FIG. 10 depicts the concentration v. time profiles of sodium gluconate oxidation on monometallic and bimetallic catalysts at 45° C. and 60° C., as examples FIG.

The reaction profiles on both a bimetallic platinum/copper alloy catalyst supported on titanium dioxide ($Pt_1Cu_3$-c) and a monometallic platinum catalyst supported on titanium dioxide at 45° C. are presented in FIG. 11(a). The conversion of gluconate on the bimetallic platinum/copper alloy catalyst supported on titanium dioxide ($Pt_1Cu_3$-c) (solid lines) was found to be much faster than the monometallic platinum catalyst supported on titanium dioxide (dash lines), while the selectivity of glucaric acid was slightly lower on the bimetallic catalyst (solid lines) than the monometallic catalyst (dash lines). Although tartronic acid selectivity was very similar, oxalic acid selectivity was much higher on the bimetallic platinum/copper alloy catalyst supported on titanium dioxide ($Pt_1Cu_3$-c) (solid lines) than the monometallic catalyst (dash lines). These results indicate more significant retro-aldolization (carbon-carbon bond (C—C) cleavage induced by the presence of carbon-oxygen double bonds (C=O)) on the bimetallic catalyst as compared to the monometallic platinum catalyst supported on titanium dioxide. It further confirms the facilitated oxidation rates of C—O to C=O promoted by copper species on the surface of platinum catalysts, which is believed to be the key for the enhanced oxidation rates of sodium gluconate on the $Pt_1Cu_3$-c/$TiO_2$ catalysts. The activation energies for r1-r4 on both catalysts, calculated from rate constants at 45° C., 60° C., and 70° C., are presented in Table 3. Interestingly, the activation energy for glucaric, tartronic, and oxalic acid formation on the $Pt_1Cu_3$-c/$TiO_2$ catalyst (gradient bars in FIG. 11(b)) was much lower as compared to the Pt/$TiO_2$ catalyst (solid bars). Specifically, the activation energies for glucaric, tartronic, and oxalic acids were 36.6±0.94, 57.7±0.84 and 57.8±2.15 kJ/mol, respectively on the $Pt_1Cu_3$-c/$TiO_2$ catalyst, while these values were higher 44.5±0.44, 73.7±0.74 and 77.8±5.44 kJ/mol, respectively on the Pt/$TiO_2$ catalyst. The activation energy for C—C cleavage of gluconate remained similar for both catalysts. These experimental findings indicate that the addition of copper species to platinum particles alters the possible oxidation paths, thus lowering the activation barriers needed for the formation of aldaric acids (glucaric, tartronic, and oxalic acids).

Since the $Pt_1Cu_3$-c/$TiO_2$ catalyst displayed exceptional performance in the oxidation of sodium gluconate to glucaric acid, experiments utilizing this catalyst were performed for the one-step oxidation of glucose, with glucaric acid being the target product.

Example 2: Oxidation of Glucose

Catalyst Activity Tests Using Glucose as the Substrate.

For each experiment using glucose as the substrate, glucose was first mixed with 25 mL of deionized water to yield 26 mL of a glucose solution with a concentration of 0.56 $kmol/m^3$, and the resulting solution was then added to the glass semi-batch stirred reactor along with the solid catalyst sample. Next, a sodium hydroxide (NaOH) solution with a concentration of 1.56 $kmol/m^3$ was slowly introduced to the glucose solution at a rate of 0.2 mL/min during the reaction rather than mixing before experiments. The addition rate was controlled by a HPLC pump. The catalyst and substrate mixture was heated to the targeted reaction temperature of 45° C. and after thermal equilibrium was attained, oxygen ($O_2$) was bubbled into the solution continuously at a constant flow rate such that the oxygen ($O_2$) pressure was constant. The total reaction time was 24 hours. During the reaction, small amounts of samples (0.5 mL) were taken from the reaction mixture and analyzed by HPLC. The results of these experiments are summarized in Table 4 below.

TABLE 4

Performances of Pt/$TiO_2$ and $Pt_1Cu_3$-c/$TiO_2$ catalyst for glucose oxidation at 45° C.

| | | | | Selectivity (%) | | | | |
|---|---|---|---|---|---|---|---|---|
| # | Catalyst | Time (h) | X (%) | Gluconic | Glucaric | Tartronic | Oxalic | Others |
| 1 | Pt/$TiO_2$ | 6 | 13.0 | 100 | — | — | — | — |
| 2 | Pt/$TiO_2$ | 12 | 33.1 | 81.1 | 2.4 | — | — | 14.9 |
| 3 | Pt/$TiO_2$ | 24 | 60.9 | 1.9 | — | 0.1 | 0.1 | 39.7 |
| 4 | $Pt_1Cu_3$-c/$TiO_2$ | 6 | 100 | 37.7 | 9.3 | 12.9 | 11.5 | 12.9 |
| 5 | $Pt_1Cu_3$-c/$TiO_2$ | 12 | 100 | 22.8 | 18.1 | 16.7 | 13.9 | 18.0 |
| 6 | $Pt_1Cu_3$-c/$TiO_2$ | 24 | 100 | 10.0 | 25.4 | 20.4 | 16.5 | 21.7 |

Others: 5-keto-gluconic, glyceric, lactic, glycolic and formic acids. Some unknown products such as humic substances might be formed in small quantities during glucose conversion.

Both the conversion and the selectivity towards glucaric acid was very low on the Pt/$TiO_2$ catalyst (Experiment Nos. 1-3). Experiment Nos. 4-6 resulted in complete conversion of glucose where the reaction temperature was 45° C. The reactions were complete after 6 hours, and the selectivity of gluconic and glucaric acids was 38% and 9%, respectively. It was also found that a large fraction of $C_2$ and $C_3$ products were also formed leading to the formation of tartronic and oxalic acids. Monocarboxylic acids such as glyceric, lactic and formic acids were also formed. This suggests that the oxidation of glucose to gluconic acid is a relatively easier step as compared to secondary oxidation reactions towards glucaric acid. These results also indicate that the C—C cleavage rate of glucose was much higher than the C—C cleavage rate of sodium gluconate. Experiments at longer reaction times (Experiment Nos. 5 and 6 at 12 and 24 hours, respectively) showed that a combined selectivity of tartronic and oxalic acids increased from 24% to 37%, suggesting that once C—C cleavage occurs in the reaction medium, secondary oxidation of these smaller molecules to dicarboxylic acids was still dominant on the $Pt_1Cu_3$-c/$TiO_2$ catalyst. Similarly, at longer reaction times, the selectivity of glucaric acid was enhanced from 9% to 25%, while the selectivity of gluconic acid was reduced from 38% to 10% as is expected in consecutive reactions. The glucaric acid production rate from glucose was about 56.9 (mole per mole of Pt metal per hour) at 45° C. and 0.1 MPa $O_2$, which was much higher than existing literature reports under harsher conditions (11 mol/g atom Pt·h at 80° C. and 0.8 MPa $O_2$).

Reuse studies, or recycle studies, were also performed on the $Pt_1Cu_3$-c/$TiO_2$ catalyst. As shown in Table 5, it was found in recycle studies that the $Pt_1Cu_3$-c/$TiO_2$ catalyst exhibited good activity and marginal changes in selectivity after three recycles (see Table 5 for reaction results and FIGS. 3(d) and (h) for TEM and EDX analysis after three recycles).

TABLE 5

Recycle studies on $Pt_1Cu_3$-c/$TiO_2$ catalyst for glucose oxidation at 45° C.

| | | | Selectivity (%) | | | | |
|---|---|---|---|---|---|---|---|
| Recycle # | Time (h) | X (%) | Gluconic | Glucaric | Tartronic | Oxalic | Others |
| 1 | 24 | 100 | 11.1 | 25.3 | 18.6 | 16.5 | 23.0 |
| 2 | 24 | 100 | 10.9 | 25.7 | 16.7 | 16.5 | 25.6 |
| 3 | 24 | 100 | 10.8 | 24.4 | 15.7 | 15.4 | 27.1 |

Experimental conditions same as Table 3. After each batch, the solid catalysts were recovered by centrifuge and washed with deionized water for six times.

Example 3: Oxidation of Fructose

Catalyst Activity Tests Using Fructose as the Substrate.

Oxidation experiments utilizing fructose as the substrate were also performed using both a $Pt_1Cu_3$-c/$TiO_2$ catalyst (results shown in Table 6) and Pt/$TiO_2$ and Cu/$TiO_2$ catalysts (results shown in Table 7). The $Pt_1Cu_3$-c/$TiO_2$ catalyst outperformed the Pt/$TiO_2$ and Cu/$TiO_2$ catalysts as to overall conversion (100% after at least 10 hours) and selectivity toward the combination of gluconic, glucaric, and tartronic acids. Experimental procedures were as described with respect to Example 1 with the following experimental conditions: 2.5 g fructose, 1 g NaOH in 50 mL, 0.1 g catalyst, 45° C., 1 bar $O_2$.

TABLE 6

Fructose oxidation on $Pt_1Cu_3$/$TiO_2$ catalyst at 45° C.

| Reaction time (h) | 6 | 10 | 24 |
|---|---|---|---|
| Conversion (%) | 67.2 | 100 | 100 |
| Selectivity (%) | | | |
| Gluconic acid | 32.1 | 24.1 | 12.9 |
| Glucaric acid | 10.2 | 15.6 | 18.5 |
| Tartronic acid | 12.2 | 15.2 | 18.4 |
| Oxalic acid | 1.2 | 2.6 | 5.7 |
| Glyceric acid | 16.9 | 17.6 | 15.1 |
| Lactic acid | 5.1 | 4.2 | 4.3 |

TABLE 6-continued

Fructose oxidation on $Pt_1Cu_3/TiO_2$ catalyst at 45° C.

| Reaction time (h) | 6 | 10 | 24 |
|---|---|---|---|
| Glycolic acid | 9.2 | 8.9 | 9.9 |
| Formic acid | 4.5 | 6.6 | 9.5 |
| Carbon balance % | 91.4 | 94.8 | 94.3 |

TABLE 7

Fructose oxidation on $Pt/TiO_2$ and $Cu/TiO_2$ catalysts at 45° C.

| | Catalyst | | | |
|---|---|---|---|---|
| | $Pt/TiO_2$ | | | $Cu/TiO_2$ |
| Reaction time (h) | 6 | 10 | 24 | 10 |
| Conversion (%) | 11.5 | 19.5 | 32.3 | 4.1 |
| Selectivity (%) | | | | |
| Gluconic acid | 52.1 | 57.4 | 42.9 | 12.8 |
| Glucaric acid | 2.0 | 3.9 | 3.2 | — |
| Tartronic acid | 2.2 | 5.2 | 3.4 | — |
| Oxalic acid | — | — | — | — |
| Glyceric acid | 32.1 | 31.6 | 35.2 | 62.9 |
| Lactic acid | — | — | — | — |
| Glycolic acid | 3.2 | 1.2 | 7.1 | — |
| Formic acid | 4.5 | 6.6 | 9.5 | 19.1 |
| Carbon balance % | 96.1 | 105.9 | 101.3 | 94.8 |

Example 4: Oxidation of 5-Hydroxymethylfurfural (HMF)

Catalyst activity tests using 5-hydroxymethylfurfural (HMF) as the substrate. Oxidation experiments utilizing HMF as the substrate were performed using the $Pt_1Cu_3$-c/$TiO_2$ catalyst. The results are shown in Table 8. As shown, it was found that PtCu-c can be effective in converting HMF into furandicarboxylic acid under very mild conditions. Experimental procedures were as described with respect to Example 1 with the following experimental conditions: 2.5 g HMF, 1 g NaOH in 50 mL, 0.1 g catalyst, 45° C., 1 bar $O_2$. Experimental conditions: 2.5 g substrate in 26 mL of initial volume of solution, 0.2 mL/min NaOH solution (1.56 kmol/m³) addition rate for 2 hours.

TABLE 8

HMF oxidation on $Pt_1Cu_3/TiO_2$ catalyst at 45° C.

| Reaction time (h) | 3 | 6 | 12 | 24 |
|---|---|---|---|---|
| Conversion (%) | 30.1 | 58.3 | 87.9 | 91.1 |
| Selectivity (%) | | | | |
| 5-hydroxymethyl-furan-2-carboxylic acid | 48.7 | 55.9 | 65.4 | 60.2 |
| 5-formyl-furan-2-carboxylic acid | 35.2 | 16.5 | 8.0 | 6.7 |
| 2,5-furandicarboxylic acid | 4.0 | 12.5 | 17.2 | 20.0 |
| Carbon balance % | 87.9 | 84.9 | 90.0 | 86.9 |

The process described herein exhibits a cleaner and more environmentally compatible route over conventional processes. In addition, when compared with previously known catalyst preparation methods, the one-pot catalyst synthesis method discussed herein generates metal particles about 4-5 nm in diameter, which are much smaller than the conventional two-step methods involving (1) nucleation with excess polymers and (2) sequential impregnation on heterogeneous supports (about 10 nm in diameter), even at the same metal precursor concentration. This implies that heterogeneous solid supports such as titanium dioxide and cerium dioxide are actually acting as "ligands" for the formation of nuclei. This in turn causes the generation of well dispersed platinum and copper particles instead of disturbing the particle growth when polymers are present. The bimetallic catalysts reported here show significantly enhanced oxidation activity with improved selectivity for glucaric acid from glucose.

Example 5: Oxidation of Sodium Gluconate Using $PtPd/TiO_2$ Catalysts

Materials.

Glucose, NaOH, sodium gluconate, potassium glucarate, lactic acid, glycolic acid, formic acid and $NaBH_4$ were purchased from Sigma Aldrich. Glyceric and tartronic acids were obtained from Fisher Scientific. Metal precursors such as $H_2PtCl_6$ and $Pd(NO_3)_2$ as well $TiO_2$ (rutile and anatase) powders were also purchased from Sigma Aldrich.

Catalyst Preparation.

Catalysts consisting of PtPd nanoparticles supported on $TiO_2$ were prepared via a simple in situ reduction method in aqueous medium. This method has been found to be effective for immobilizing Pt-based nanoparticles on solid supports. In general, known amounts of $H_2PtCl_6$ and $Pd(NO_3)_2$ were mixed with deionized (DI) water added dropwise into an aqueous phase slurry of $TiO_2$. Depending on how $H_2PtCl_6$ and $Pd(NO_3)_2$ were added, PtPd nanoparticles with alloy, core-shell and cluster-in-cluster configurations were formed on rutile or anatase $TiO_2$ supports ($TiO_{2-r}$, $TiO_{2-a}$). Detailed catalyst preparation procedures followed are described above. (1) For $PtPd_a$ catalyst, predetermined amounts of metal precursors, $H_2PtCl_6 \cdot 6H_2O$ and $Pd(NO_3)_2$ were dissolved in 150 mL DI water, followed by addition of this solution dropwise to a 300 mL aqueous slurry of $TiO_2$ containing acetonitrile. The concentration of precursors in the slurry was in the range of $1.36 \times 10^{-4}$-$1.44 \times 10^{-3}$ kmol/m³. After stirring for 2 hours, a solution of 0.2 g of $NaBH_4$ in 50 mL water was introduced into the slurry dropwise, after which the whole mixture was stirred overnight (16-20 hours). The Pt and Pd metal contents in solid supports were in the range of 0.96-1.12 wt % as determined by ICP. (2) For Pd—Pt sample, $Pd(NO_3)_2$ dissolved in 75 mL DI water was first added dropwise to the $TiO_2$ slurry in 300 mL water. Then 0.1 g of $NaBH_4$ in 25 mL was slowly added to this slurry. After 2 hours, 75 mL of $H_2PtCl_6 \cdot 6H_2O$ solution was added dropwise, after which another 25 mL of 0.1 g $NaBH_4$ was added. The whole mixture was stirred for an additional 2 hours before the solid catalysts were filtered. (3) For the Pt—Pd sample, the order of Pd and Pt precursor addition was changed. (4) For $PtPd_c$ catalyst sample, 75 mL of $H_2PtCl_6 \cdot 6H_2O$ and 75 mL of $Pd(NO_3)_2$ solutions were prepared separately. Then 60 mL of $H_2PtCl_6 \cdot 6H_2O$ and 15 mL of $Pd(NO_3)_2$ solutions were added to the $TiO_2$ slurry in water dropwise before 25 mL of 0.1 g $NaBH_4$ was charged. After 2 hours reduction time, 15 mL of $H_2PtCl_6 \cdot 6H_2O$ and 60 mL of $Pd(NO_3)_2$ solution were added followed by addition of another 25 mL of 0.1 g $NaBH_4$. The catalyst was filtered, washed with DI water and dried in a vacuum oven after additional 2 hours of reduction time. (5) For $PtPd_a7$ sample, the experimental procedure was identical to (1) except that the metal precursors were reduced at pH=7 (tuned with NaOH addition).

Activity Tests.

The activity tests were carried out in a three-neck flask with controlled heating hot plate under magnetic stirring at 1000 RPM. Similar operating procedures have already been discussed above and hence only discussed briefly here. For oxidation experiments, NaOH solution was slowly introduced at a rate of 0.04 mL/min to glucose solution and catalyst slurry. The addition rate was controlled by an HPLC pump. The catalyst and glucose solution mixture was heated at a desired reaction temperature before both NaOH solution and $O_2$ (at a rate of about 60 mL/min) were introduced. The total pressure was maintained at 0.1 MPa throughout each experiment. A liquid condenser was used to condense the vapor. During the reaction, small amounts of samples (0.5-2 mL) were withdrawn from the reaction mixture and analyzed by HPLC, for which analytical conditions and chromatograph used were similar to those described previously. The maximum liquid volume loss during an experiment was observed to be approximately 0.6 mL.

The significance of gas-to-liquid, liquid-to-solid and intra-particle mass transfer limitation was evaluated using the criteria proposed previously and the mass transfer and solubility parameters calculated using literature correlations. The corresponding ratios of observed reaction rate to the maximum rates of gas-to-liquid, liquid-to-solid and intra-particle mass transfer rate were found to be approximately $2.7 \times 10^{-6}$, $6.2 \times 10^{-4}$ and $9.2 \times 10^{-4}$, respectively, suggesting negligible mass transfer limitations under the reaction conditions.

Catalyst Characterization.

Brunauer-Emmett-Teller (BET) measurement, Chemisorption, UV-Vis spectra, transmission electron microscopy (TEM), scanning electron microscopy (SEM) and x-ray diffraction (XRD) were carried out as described previously.

BET:

$N_2$ adsorption studies were carried out using NOVA 2200e Instrument. Detailed measurement procedures were similar to that described previously.

Chemisorption:

$H_2$ adsorption was carried out in Autochem 2910 Instrument. Temperature programmed desorption (TPD) of H2 was carried out in the same pot after chemisorption study of a sample.

UV-Vis Spectra:

Surface absorbance under UV-Vis was carried out using Shimadzu UV-3600 UV-VIS-NIR Spectrophotometer. The samples were dispersed in hexane solution and the solvents were dried on a quartz plate before optic spectrum data was recorded.

Transmission Electron Microscopy (TEM):

Sample preparation and detailed procedures are similar to that previously described. Samples were prepared by suspending the solid catalyst sample in ethanol and agitating in an ultrasonic bath. 10 pt,L of catalyst sample was placed onto a copper mesh grid. The wet grid was allowed to air-dry for several minutes prior to examination under TEM. Around 200 particles were measured and average particle size as well as standard deviation were calculated.

Scanning Electron Microscopy (SEM):

A Versa 3D dual beam Scanning Electron Microscope/Focused Ion Beam (FEI, Hillsboro, Oreg., USA) with a silicon drift EDX detector (Oxford Instruments, X-Max, UK) was used to measure the surface morphology, elemental composition and distribution of metals. All the SEM data reported were obtained at an acceleration voltage of 15 kV, spot size 3.0 and the images were collected with an ET (Everhart Thornley) detector. The elemental mapping and energy spectrums were acquired with Aztec tools (Oxford Instruments, UK).

X-Ray Diffraction (XRD):

This measurement was performed on a Bruker D8 powder diffractometer with a copper target ($CuK_\alpha$ radiation) operating at 40 kV and a current of 40 mA to analyze the crystal structures of materials.

Characterization of Mono $Pt/TiO_2$ and Bimetallic $PtPd/TiO_2$ Catalysts.

Physical Properties and Chemisorption.

Surface area and pore size analysis were carried out for all solid catalyst samples and the results are shown in Table 9.

TABLE 9

Physical properties and chemisorption analysis of solid catalyst samples

| Catalyst | SBET ($m^2$/g) | Vpore ($10^{-2}$ $m^3$/g) | Metal dispersion (%) | Particle size (mesh) |
|---|---|---|---|---|
| $Pt/TiO_{2-a}$ | 9.19 | 1.60 | 46 | 325 |
| $PdTiO_{2-a}$ | 17.2 | 4.60 | 59 | 325 |
| $PtPd_a/TiO_{2-r}$ | 8.03 | 1.56 | 22 | 325 |
| $PtPd_a/TiO_{2-a}$ | 14.6 | 1.56 | 19 | 325 |
| $PtPd_a7/TiO_{2-a}$ | 14.6 | 3.11 | 33 | 325 |
| $PtPd_c/TiO_{2-a}$ | 11.4 | 2.03 | 35 | 325 |
| $Pt—Pd/TiO_{2-a}$ | 16.2 | 3.66 | — | 325 |
| $Pd—Pt/TiO_{2-a}$ | 15.3 | 2.96 | — | 325 |

The total surface area of $TiO_2$ supported catalysts is very low, in the range of 4.5-17.2 $m^2$/g. The overall porosity of $TiO_2$ materials is also low. The densities of $TiO_{2-a}$ and $TiO_{2-r}$ materials are 3.9 g/mL and 4.17 g/mL, respectively. Pt and Pd nanoparticles are therefore predominantly deposited on the surface of the support (confirmed by TEM). Chemisorption using $H_2$ were also carried out for all solid catalyst samples to estimate the active metal dispersion as also shown in Table 9.

TEM.

Figure 15A:
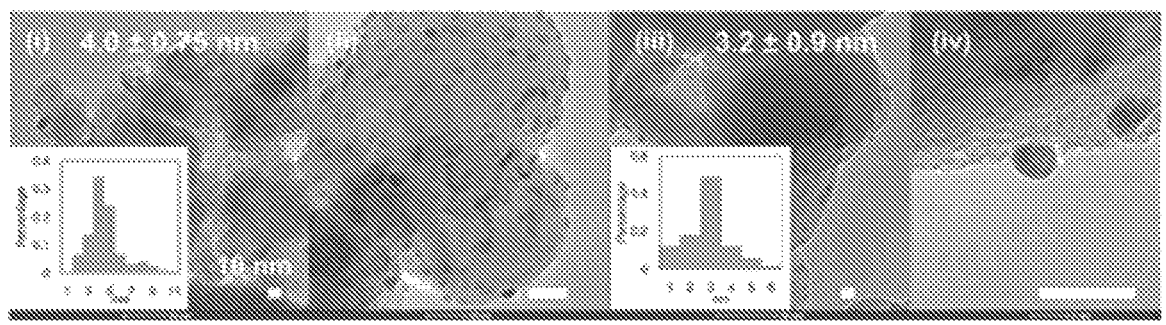
FIG. 15(a) depicts TEM images of Pt/$TiO_{2-r}$ (i, ii) and Pt/$TiO_{2-a}$ (iii, iv) samples.
Figure 15B:
FIG. 15(b) depicts TEM images of $PtPd_d$/$TiO_{2-r}$.
Figure 15C:
FIG. 15(c) depicts TEM images of $PtPd_d$/$TiO_{2-a}$.

TEM images are shown in FIGS. 15(a) $Pt/TiO_{2-r}$ (i,ii) and $Pt/TiO_{2-a}$ (iii,iv), (b) $PtPd_a/TiO_{2-r}$, (c) $PtPd_a/TiO_{2-a}$, and EDX mapping of (d) $PtPd_c/TiO_{2-a}$ and (e) $PtPd_a7/TiO_{2-a}$ catalysts and (f) used $PtPd_a/TiO_{2-a}$ (whitebars indicate 10 mm scale). In particular, we find that monometallic Pt on both rutile [$TiO_{2-r}$, (i)-(ii) in FIG. 15(a)] and anatase [$TiO_{2-a}$, (iii)-(iv) in FIG. 15(a)] support display similar particle sizes (3.2-4.0 nm), suggesting that the different crystalline forms of $TiO_2$ support have negligible effect on the Pt particle formation during $NaBH_4$ reduction. However, when Pd species were added to the monometallic Pt system [FIGS. 15(b) and (c)], larger nanoparticles (6.5-7.5 nm) were observed on both $TiO_2$ supports. As seen from the EDX mapping in FIG. 15(b) (c), PtPd both exhibit alloy structures on the two types of $TiO_2$ supports.

Figures 15D, 15E:
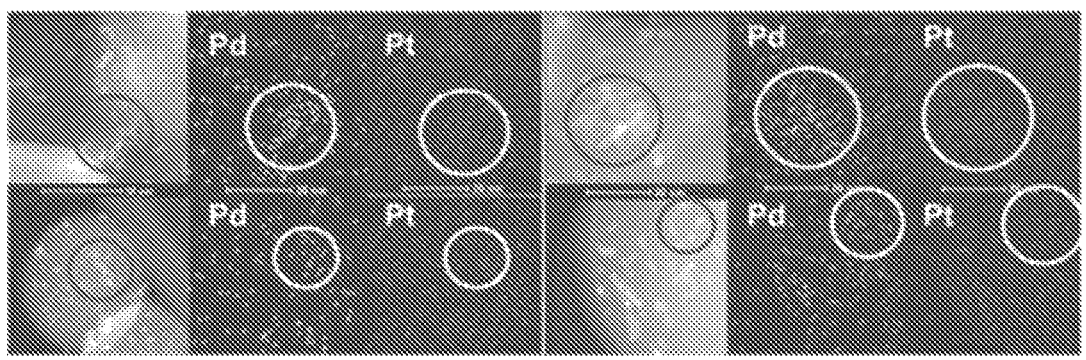
FIG. 15(d) depicts STEM and EDX mapping of $PtPd_d$/$TiO_{2-a}$.
FIG. 15(e) depicts STEM and EDX mapping of $PtPd_a7$/$TiO_{2a}$.
Figure 15F:
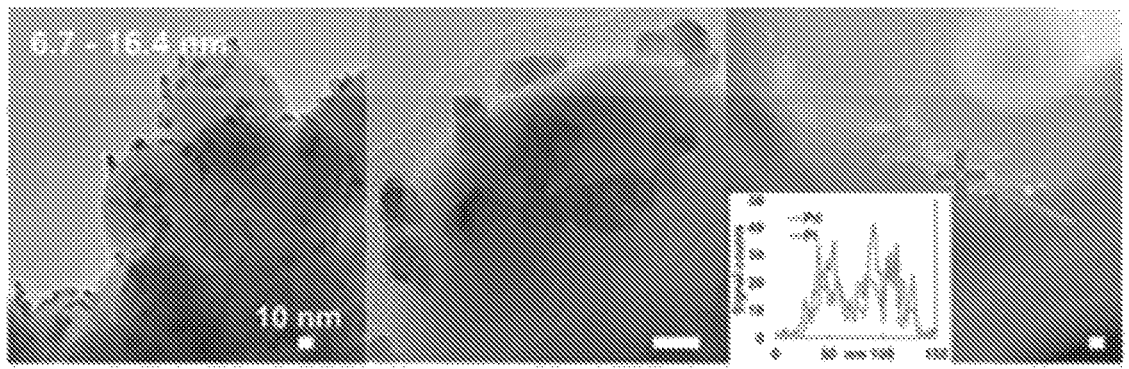
FIG. 15(f) depicts STEM and EDX mapping of used $PtPd_d$/$TiO_{2-a}$ catalysts.
Figure 16:
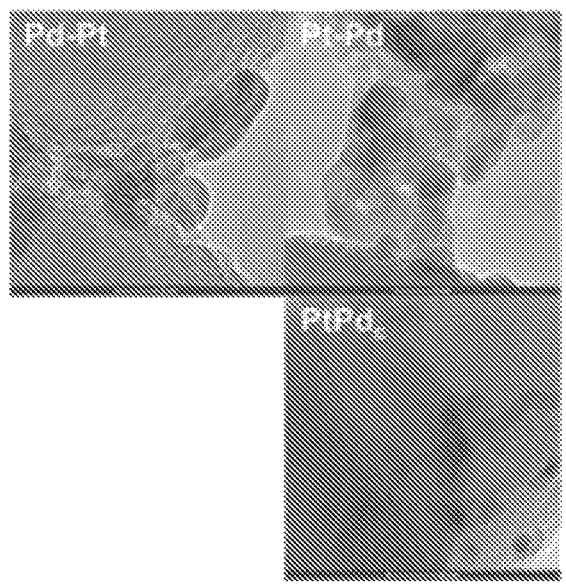
FIG. 16 depicts TEM of Pd—Pt, Pt—Pd and $PtPd_c$ catalyst samples.
Figures 17A, 17B:
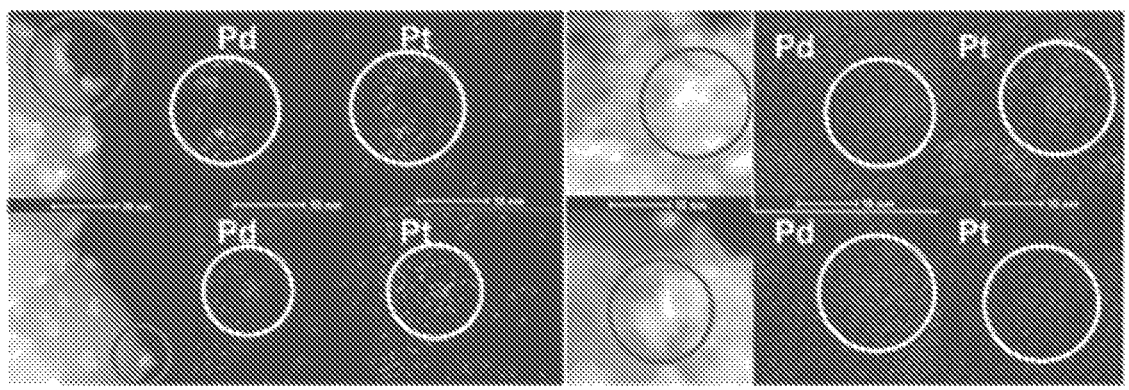
FIG. 17(a) depicts Pd—Pt/$TiO_{2-a}$.
FIG. 17(b) depicts Pt—Pd/$TiO_{2-a}$.

STEM results for $PtPd_c$ and $PtPd_a7$ catalysts are presented in FIGS. 15(d) and (e) while TEM images of Pd—Pt, Pt—Pd, $PtPd_c$ and $PtPd_a7$ catalyst samples are shown in FIGS. 16 and 17. Interestingly, nanoparticles in the $PtPd_c$ sample are more likely random alloy (cluster-in-cluster) structures, as shown in FIG. 15(d). For the comparison purposes, $PtPd_a7$ sample was also prepared at room temperature but at pH=7 instead of pH=3-4 (for $PtPd_a$ sample). This sample displays a Pt-core/Pd-shell structure (FIG. 15(e)).

SEM.

Figure 18A:
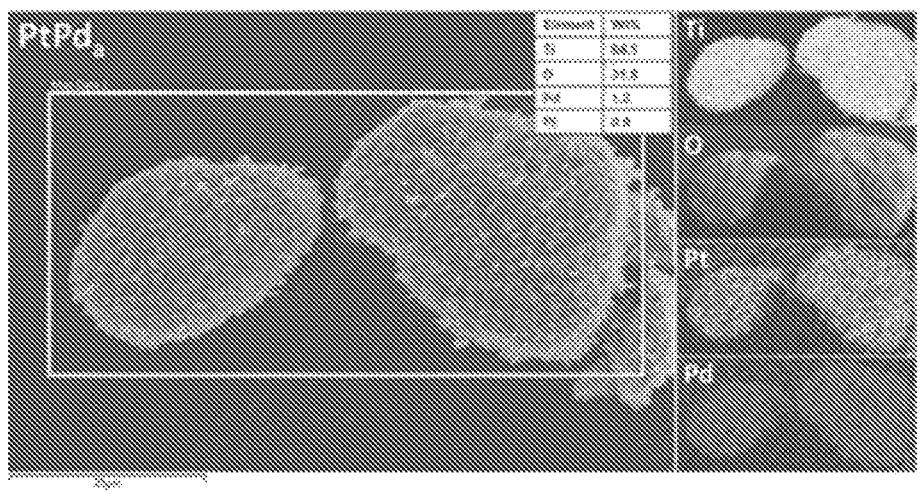
FIG. 18(a) depicts SEM images of PtPd$_d$/TiO$_{2-a}$.
Figure 18B:
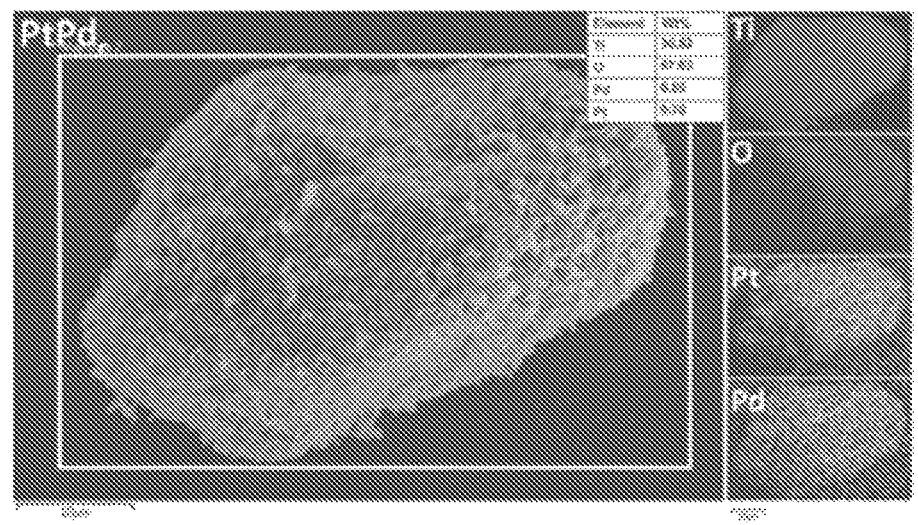
FIG. 18(b) depicts SEM images of PtPd$_c$/TiO$_{2-a}$.
Figure 18C:
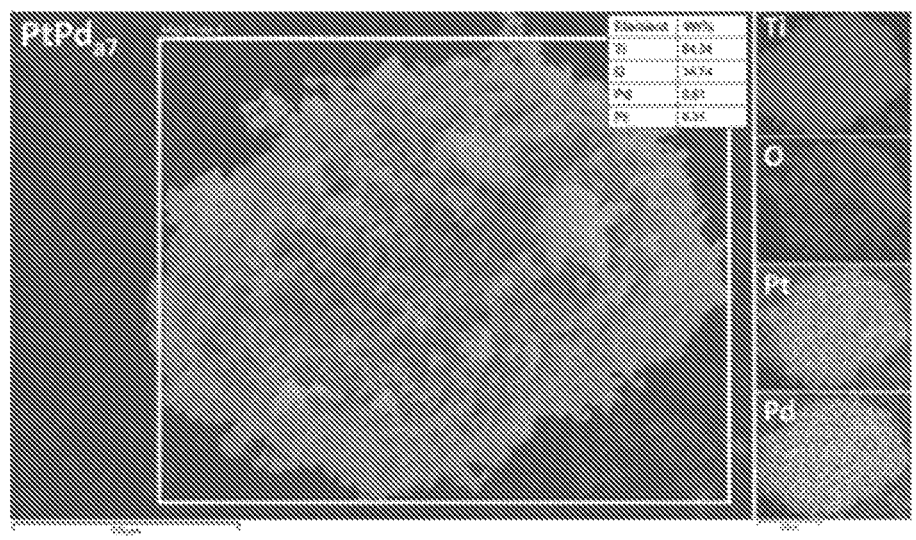
FIG. 18(c) depicts SEM images of PtPd$_a$7/TiO$_{2-a}$.

SEM images of selected bimetallic PtPd catalysts were also collected for the purpose of investigating the surface morphologies of $TiO_2$ supported catalysts. As seen in FIGS. 18(a) $PtPd_a/TiO_{2-a}$, (b) $PtPd_c/TiO_{2-a}$ and (c) $PtPd_a7/TiO_{2-a}$ images along with surface elemental analysis are presented.

Figure 19:
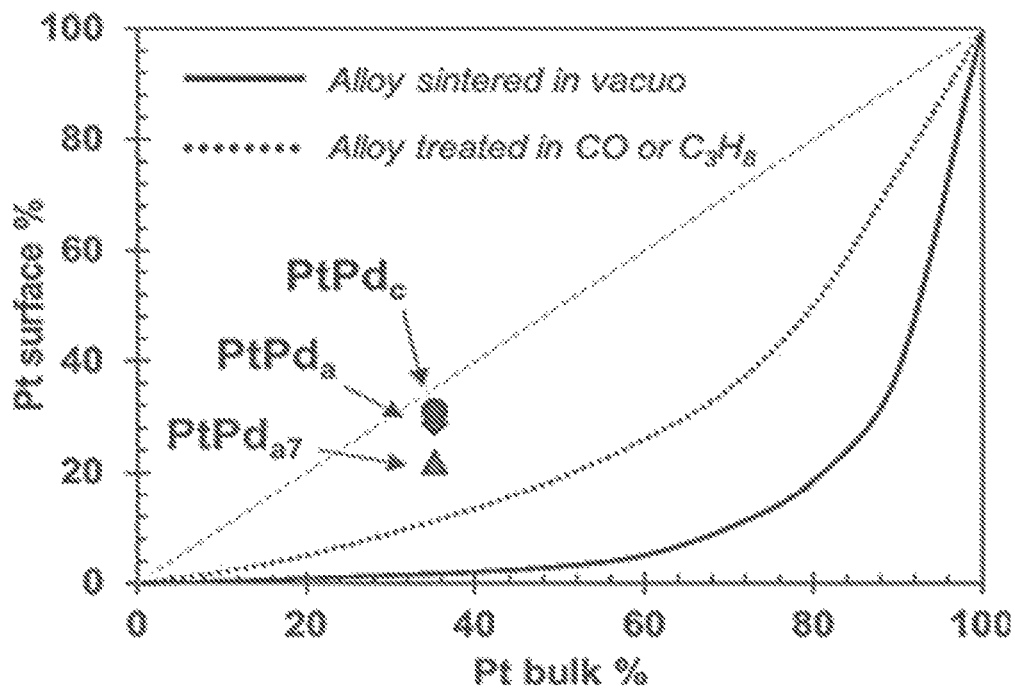
FIG. 19 depicts surface-bulk relationship of PtPd alloy particles.

TiO$_2$ particle sizes are in a range less than 50 jtm for all the three samples, which confirm that our catalysts are in fine powder forms. In addition, Pt and Pd are found to be well dispersed on TiO$_2$ support, which is consistent with information obtained from TEM characterization. We also plotted the bulk and surface Pt metal composition in PtPd$_a$/TiO$_{2-a}$, PtPd$_c$/TiO$_{2-a}$ and PtPd$_a$7/TiO$_{2-a}$ catalyst samples and compared with literature data. Literature reports [solid and dash lines in FIG. 19] show that Pd species tend to migrate towards the surface of nanoparticles, which were prepared by impregnation method. However, it is interesting to find that the surface composition of Pt (atomic ratio of Pt to Pd) of the three samples in this study is higher than literature values, indicating that the aqueous wet chemical reduction of Pd$^{2+}$ is faster than Pt$^{4+}$ resulting in relatively higher Pd concentration in the core of alloy nanoparticles.

UV-Vis.

Figure 20:
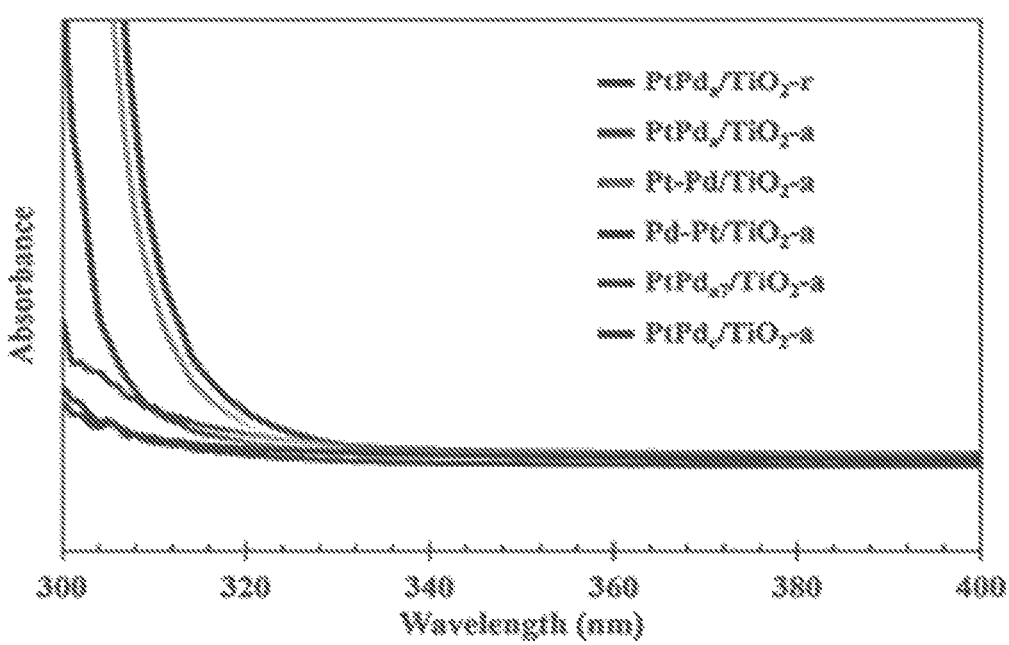
FIG. 20 depicts UV-Vis spectra of bimetallic PtPd/TiO$_2$ catalysts.

Optical absorption characteristics of various bimetallic PtPd/TiO$_2$ catalysts was carried out in order to probe the possible metal-metal and metal-support interactions on catalyst surface and the results are depicted in FIG. 20. Only PtPd$_a$7 sample displays an absorption onset at 310 nm, while all other samples show a shift of onset wavelength towards 330 nm. The bandgap on PtPd$_a$7 (Pd-shell) sample is similar to monometallic Pt/TiO$_2$ absorption, suggesting its plasmon absorbance is insignificant. The red shift on other bimetallic samples indicates a strong plasmon absorbance of these bimetallic PtPd nanoparticles on TiO$_2$ support. More specifically, we find that both PtPd$_a$/TiO$_{2-r}$ and PtPd$_a$/TiO$_{2-a}$ catalysts display almost identical optical behavior. Hence, it is possible that the interactions between PtPd alloy particles with different TiO$_2$ supports are similar. But other bimetallic samples, including Pd—Pt and PtPd$_c$ ones, displaying cluster-in-cluster morphologies with different extents, show relatively weak absorbance signals compared with PtPd$_a$/TiO$_{2-r}$ and PtPd$_a$/TiO$_{2-a}$ catalysts.

XRD.

Figure 21:
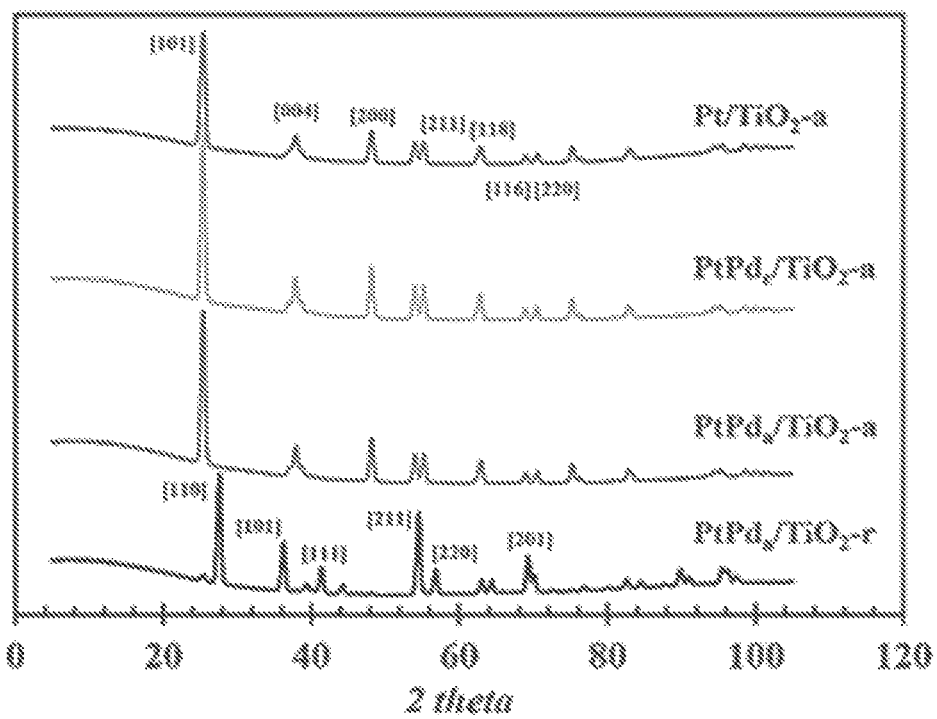
FIG. 21 depicts x-ray diffraction patterns of different TiO$_2$ supported PtPd catalysts.

XRD analysis was further conducted on selected catalyst samples. XRD patterns of rutile and anatase TiO$_2$ supported monometallic Pt and bimetallic PtPd catalysts are shown in FIG. 21. For PtPd$_a$/TiO$_{2-r}$ sample, strong diffraction peaks at 27° C., 36° C. and 55° C. indicate [110], [101] and [211] lattices in rutile phase, while 25° C. and 48° C. peaks found on TiO$_{2-a}$ supported samples suggest the presence of [101] and [220] phases. Due to the lower loading of Pt and Pd metals, it is difficult to detect their characteristic peaks. We find that Pt [111] peak overlaps with one of the peaks on TiO$_{2-r}$ support around 40° C., while a small peak at 82° C. might indicate existence of Pt [311] on the surface. A similar peak is also found on TiO$_{2-a}$ samples but shifted slightly towards 85° C., which indicates a possible interaction with Pd species on the support. Pd [111] exhibits a similar diffraction peak around 40° C., which is also weak. The small peak at 47° C. in bimetallic PtPd samples suggests that Pd [200] might exist on the catalyst surface.

Activity and Selectivity of Mono and Bimetallic Catalysts.

Figure 22:
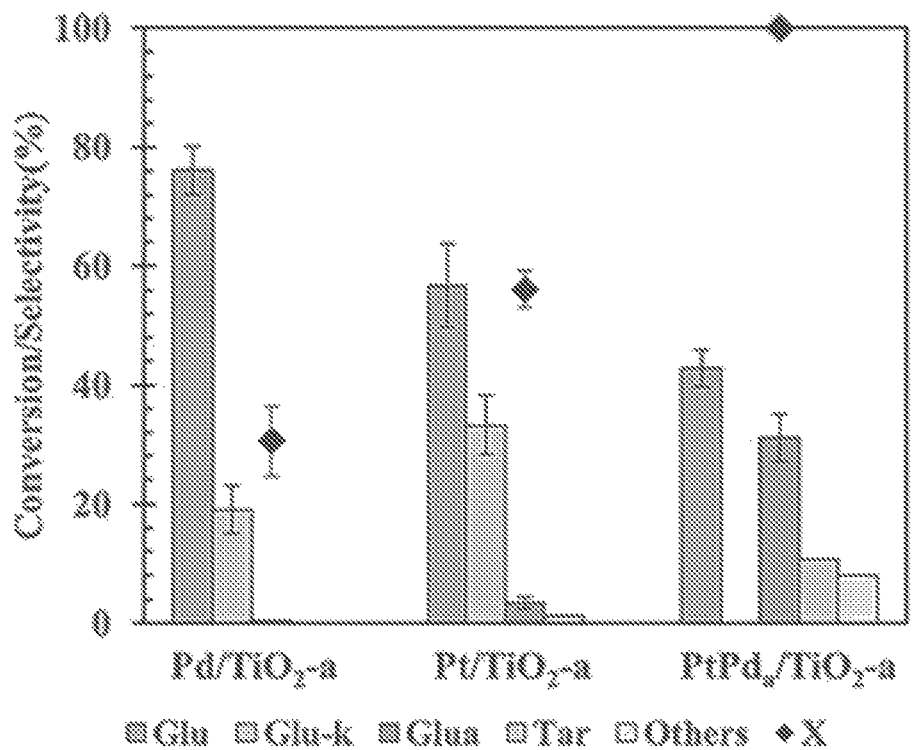
FIG. 22 depicts conversion and selectivity of glucose oxidation on Pd/TiO$_{2-a}$, Pt/TiO$_{2-a}$ and PtPd$_d$/TiO$_{2-a}$ catalysts.

In the benchmark studies on direct oxidation of glucose, we found that bimetallic PtPd$_a$/TiO$_2$ catalysts display a synergistic effect in enhancing both the catalytic activity and glucaric acid selectivity compared to monometallic Pt/TiO$_2$ and Pd/TiO$_2$ catalysts under the following reaction conditions, as shown in FIG. 22: T: 45° C., substrate concentration: 0.28 kmol/m$^3$, 1.50 kmol/m$^3$ of NaOH solution was added to glucose solution at 0.04 mL/min rate, catalyst loading: 0.1 g, solvent: DI H2O, total liquid volume: 50 mL, O$_2$ bubbling rate: 60 mL/min at 0.1 MPa. Reaction time: 12 hours for Pd/TiO$_{2-a}$ and Pt/TiO$_{2-a}$, 10 hours for PtPd$_a$/TiO$_{2-a}$). In particular, the preliminary studies were carried out on mono and bimetallic Pd/TiO$_{2-a}$, Pt/TiO$_{2a}$ and PtPd$_a$/TiO$_{2-a}$ catalysts at 45° C. as shown in FIG. 22 and Table 10.

TABLE 10

Benchmark Experiments on Oxidation of Glucose on Monometallic Pt/TiO$_2$ and Pd/TiO$_2$ Catalysts

| # | Catalyst | Time (h) | X (%) | Selectivity (%) | | | | |
|---|---|---|---|---|---|---|---|---|
| | | | | Glu | Glu-k | Gla | Tar | Others$^\&$ |
| 1 | Pt/TiO$_{2-r}$ | 6 | 16.0 | 100 | — | — | — | — |
| 2 | Pt/TiO$_{2-r}$ | 12 | 38.9 | 86.1 | 13.3 | 1.4 | — | — |
| 3 | Pt/TiO$_{2-r}$ | 24 | 61.1 | 55.5 | 36.7 | 1.9 | 0.1 | 0.1 |
| 4 | Pt/TiO$_{2-a}$ | 6 | 24.5 | 98.9 | — | — | — | — |
| 5 | Pt/TiO$_{2-a}$ | 12 | 56.1 | 56.7 | 33.3 | 3.4 | 1.1 | — |
| 6 | Pt/TiO$_{2-a}$ | 24 | 88.8 | 33.6 | 50.2 | 9.1 | 5.1 | 0.5 |
| 7 | Pd/TiO$_{2-a}$ | 6 | 11.6 | 100 | — | — | — | — |
| 8 | Pd/TiO$_{2-a}$ | 12 | 30.5 | 76.1 | 19.1 | 0.4 | — | — |
| 9 | Pd/TiO$_{2-a}$ | 24 | 49.9 | 49.5 | 30.1 | 9.6 | 5.8 | 0.9 |

Glu: gluconic acid, Glu-k: 5-keto-gluconic acid, Gla: glucaric acid, Tar: tartronic acid,
$^\&$Others: oxalic, glyceric, lactic, glycolic and formic acids.

Glucose conversion on Pd/TiO$_{2-a}$ and Pt/TiO$_{2-a}$ catalysts was found to be 30% and 56% respectively in 12 hours, while with a bimetallic PtPd$_a$/TiO$_{2-a}$ catalyst complete conversion of glucose was achieved in 10 hours. The glucose oxidation activities measured as TOF on Pd/TiO$_{2-a}$, Pt/TiO$_{2-a}$ and PtPd$_a$/TiO$_{2-a}$ catalysts are 50, 248 and 2,404 h$^{-1}$, respectively.

With respect to product distribution, both monometallic Pd/TiO$_{2-a}$ and Pt/TiO$_2$. a catalysts give high selectivity towards gluconic acid (S=57-76%) with negligible glucaric acid formation (S~4%) during 12 hours reaction time. In sharp contrast, glucaric acid selectivity is found to be 31% on bimetallic PtPd$_a$/TiO$_{2-a}$ catalyst. Besides, 5-keto-gluconic acid (a by-product resulting from isomerization of glucuronic acid) selectivity is about 19-33% on monometallic catalysts, while the formation of this product is negligible on the bimetallic catalyst. These differences in activity and selectivity indicate that the bimetallic PtPd catalyst has higher oxidation activity for gluconic to glucaric acid while this reaction is very weak on monometallic Pt and Pd catalysts. In addition, other products, tartronic, oxalic, glyceric, glycolic and lactic acids were also detected on the bimetallic catalyst while the selectivity towards these products is low on monometallic catalysts.

Support effects on activity and selectivity of monometallic Pt and bimetallic PtPd catalysts were also studied and the results presented in Tables 11 and 12 under the specified reaction conditions.

TABLE 11

Benchmark data for oxidation reactions on PtPd/TiO$_2$ catalysts

| # | Catalyst | Substrate | Time (h) | X (%) | Selectivity (%) | | | | |
|---|---|---|---|---|---|---|---|---|---|
| | | | | | Glu | Gla | Tar | Oxa | Others* |
| 1 | PtPd$_a$/TiO$_{2-r}$ | Gluconate | 6 | 41.4 | — | 41.2 | 28.7 | 6.8 | 17.0 |
| 2 | PtPd$_a$/TiO$_{2-a}$ | Gluconate | 6 | 78.5 | — | 37.8 | 28.8 | 8.0 | 16.5 |
| 3 | PtPd$_a$/TiO$_{2-a}$ | Glucose** | 6 | 100 | 57.7 | 25.3 | 6.9 | 2.5 | 2.9 |
| 4 | PtPd$_a$/TiO$_{2-a}$ | Glucose** | 10 | 100 | 42.8 | 31.1 | 10.7 | 3.9 | 4.0 |
| 5 | PtPd$_a$/TiO$_{2-a}$ | Glucose** | 24 | 100 | 28.0 | 40.4 | 15.4 | 5.5 | 6.7 |

Experimental conditions. T: 45° C., substrate concentration: 0.28 kmol/m$^3$, NaOH concentration: 0.75 kmol/m$^3$, catalyst loading: 0.1 g, solvent: DI H$_2$O, total liquid volume: 50 mL, O$_2$ bubbling rate: 60 mL/min at 0.1 MPa. Glu: gluconic acid, Gla: glucaric acid, Tar: tartronic acid, Oxa: oxalic acid.
*Others: glyceric, lactic, glycolic and formic acids.
**1.50 kmol/m$^3$ of NaOH solution was added to glucose solution at 0.04 mL/min rate.

TABLE 12

Benchmark Experiments on Oxidation of Glucose on PtPd/TiO$_2$ Catalysts

| # | Catalyst | Time (h) | X (%) | Selectivity (%) | | | | |
|---|---|---|---|---|---|---|---|---|
| | | | | Glu | Gla | Tar | Oxa | Others* |
| 1 | PtPd$_a$/TiO$_{2-a}$ | 6 | 100 | 54.0 | 25.3 | 7.8 | 3.9 | 3.9 |
| 2 | PtPd$_a$/TiO$_{2-a}$ | 12 | 100 | 29.0 | 36.8 | 11.2 | 6.7 | 4.7 |
| 3 | PtPd$_a$/TiO$_{2-a}$ | 24 | 100 | 16.2 | 44.3 | 17.8 | 8.6 | 5.8 |

Experimental conditions same as Table 10, but with 1.0 g glucose and 1.8 g of sodium gluconate (equivalent to 1.5 g glucose in molar amount) as substrate. Selectivity was calculated based on 2.5 g glucose as starting material. Glu: gluconic acid, Gla: glucaric acid, Tar: tartronic acid, Oxa: oxalic acid. Others: glyceric, lactic, glycolic and formic acids.

TiO$_{2-a}$ outperformed TiO$_{2-r}$ in terms of oxidation activity (Entries #1 and #2 in Table 11, Entries #1-#6 in Table 12). Further experimental results using PtPd$_a$/TiO$_{2-a}$ catalyst (Entry #3) showed that glucose was actually completely converted even before 6 hours at 45° C. The combined selectivity of C6 (gluconic and glucaric acid) products is higher than 82%, implying that occurrence of C—C cleavage reactions was negligible within 6 hour reaction time. When the reaction was prolonged to 12 hours, the selectivity of gluconic acid decreases from 58% to 43% while that of glucaric, tartronic and oxalic acids increases from 34.7% to 45.7%. After 24 hours reaction, the selectivity to glucaric, tartronic and oxalic acids is 40.4%, 15.4% and 5.5% respectively. These results suggest that gluconic acid is a key intermediate for the formation of these aldaric acids (glucaric, tartronic and oxalic acids). Although C—C cleavage occurs simultaneously with glucaric acid formation, most of the products were aldaric rather than aldonic acids (gluconic, glyceric, glycolic, lactic and formic acids), indicating that secondary oxidation reactions were significant on the bimetallic PtPd$_a$/TiO$_{2-a}$ catalyst surface. The oxidation performance of bimetallic PtPd catalysts on TiO$_{2-a}$ was therefore the main focus of further studies in this work.

Structure-Activity Relationship.

Figure 23:
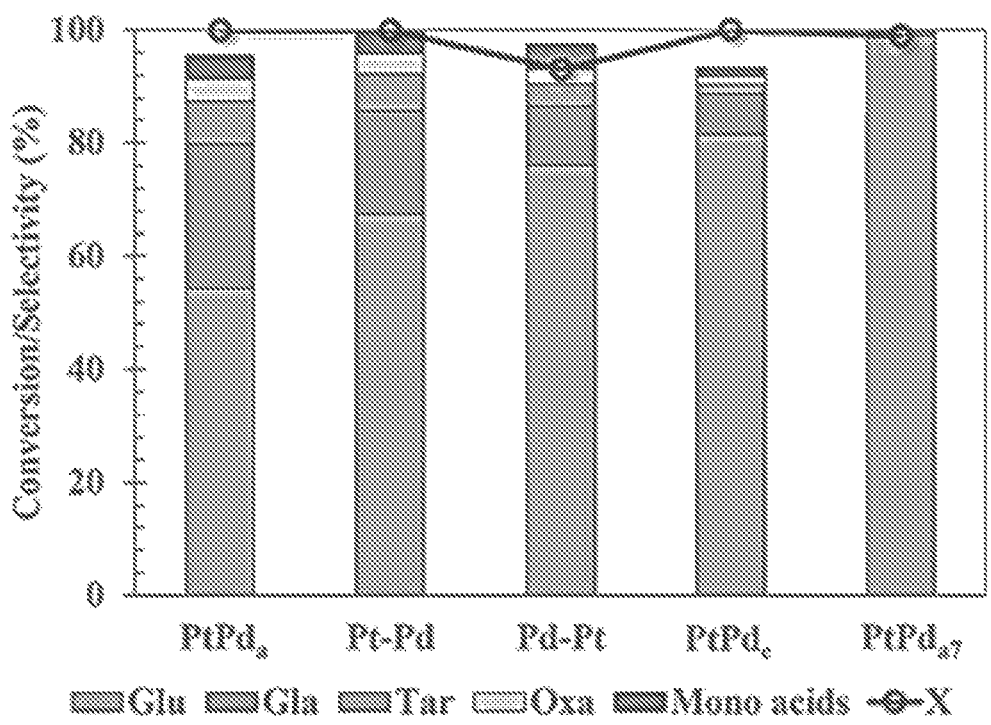
FIG. 23 depicts glucose conversion and selectivity on different PtPd/TiO$_2$ catalysts at 45° C. in 6 hours.

Various bimetallic PtPd$_a$, Pt—Pd, Pd—Pt, PtPd$_a$7 and PtPd$_c$ catalysts supported on TiO$_{2-a}$ were prepared and evaluated for glucose oxidation at 45° C. and 0.1 MPa O$_2$ pressure under the following reaction conditions: 1.50 kmol/m$^3$ of NaOH solution was added to glucose solution at 0.04 mL/min rate, catalyst loading: 0.1 g, solvent: DI H2O, O$_2$ bubbling rate: 60 mL/min at 0.1 MPa. Glu: gluconic acid, Gla: glucaric acid, Tar: tartronic acid, Oxa: oxalic acid. *Others: glyceric, lactic, glycolic and formic acids. The results during 6 hours reaction time are shown in FIG. 23. Glucose conversion was total on all PtPd catalysts. With regard to the selectivity towards oxidation products, PtPd$_a$ catalyst exhibits 25.3%, 6.9% and 2.5% selectivity to glucaric, tartronic and oxalic acids respectively, while only 10.4%, 3.9% and 2.6% of these acids were observed on Pd—Pt catalyst. Furthermore, the combined selectivity to C1-C3 acids is relatively higher on Pd—Pt catalyst (S>17%) compared with PtPd$_a$ (S=12%). PtPd$_a$7 catalyst exhibits dominant gluconic acid selectivity after 6 hours, suggesting its poor secondary oxidation activity.

As shown in TEM characterization of these bimetallic PtPd catalysts, we find that PtPd$_a$, PtPd$_c$, PtPd$_a$7 are alloy, cluster-in-cluster, and Pd-shell structures, respectively. PtPd$_a$ alloy structure displays better oxidation performance than other morphologies while cluster and Pd-shell structures exhibit relatively poor activity and selectivity. In terms of possible metal-support and metal-metal interactions, as already shown in FIG. 20, we observed that both PtPd$_a$ and Pt—Pd samples show strong metal-TiO$_2$ interaction. For PtPd$_a$7 (Pd-shell structure) catalyst, the bandgap is similar to monometallic Pt/TiO$_2$, suggesting that Pt and TiO$_2$ interaction is insignificant. This phenomenon is consistent with its poor secondary oxidation activity. In addition, although PtPd$_c$ catalyst also showed bandgap shift (about 330 nm), the absorbance is lower than the alloy and random alloy structures (PtPd$_a$ and Pt—Pd), indicating that the metal-metal interaction in cluster-in-cluster structure is relatively weak.

In order to understand the dependence of global oxidation reaction rates, including primary and secondary oxidation as well as C—C cleavage reactions on PtPd structures, reaction profiles of glucose oxidation were experimentally measured on selected PtPd catalysts. We chose PtPd$_a$, PtPd$_c$ and PtPd$_a$7 catalysts for this study. The corresponding concentration-time profiles are shown FIGS. 24-27 under the following reaction conditions: 1.50 kmol/m$^3$ of NaOH solution was added to glucose solution at 0.04 mL/min rate. Catalyst loading: 0.1 g, solvent: DI H2O, O$_2$ bubbling rate: 60 mL/min at 0.1 MPa. In the FIGs., Glu: gluconic acid, Gla: glucaric acid, Tar: tartronic acid, Oxa: oxalic acid. *Others: glyceric, lactic, glycolic and formic acids.

Figure 24:
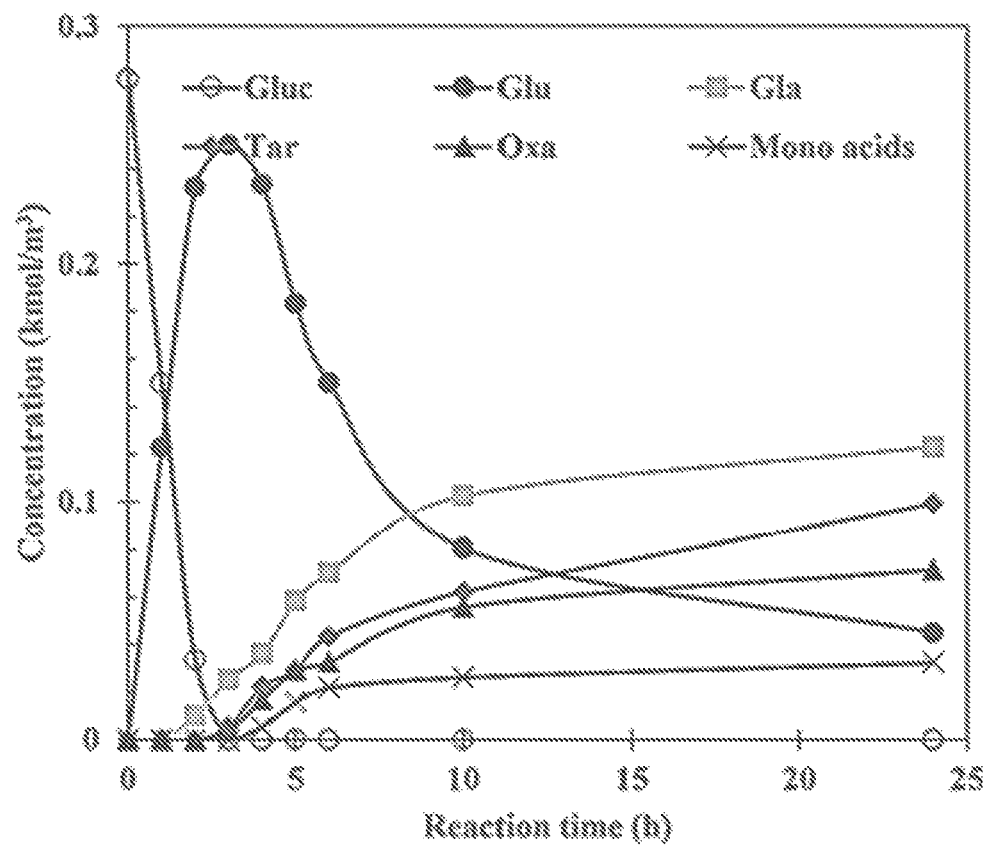
FIG. 24 depicts glucose concentration-time profiles on PtPd$_d$/TiO$_{2-a}$ catalyst at 45° C.

As shown in FIG. 24, concentration profiles on PtPd$_a$ catalyst at 45° C. show that glucose concentration decreased from 0.28 kmol/m$^3$ to zero within only 3 hours. Notably, gluconic acid was the dominant product before glucose was completely consumed. The formation of glucaric acid as well as other carboxylic acids with lower C numbers was detectable only after 3 hours, with gluconic acid reaching a peak and then decreasing from 0.27 kmol/m$^3$ to <0.05 kmol/m$^3$ within 24 hours. The concentrations of glucaric, tartronic and oxalic acids increased from almost zero before 3 hours to approximately 0.11, 0.095, and 0.07 kmol/m$^3$ respectively within 24 hours.

Figure 25:
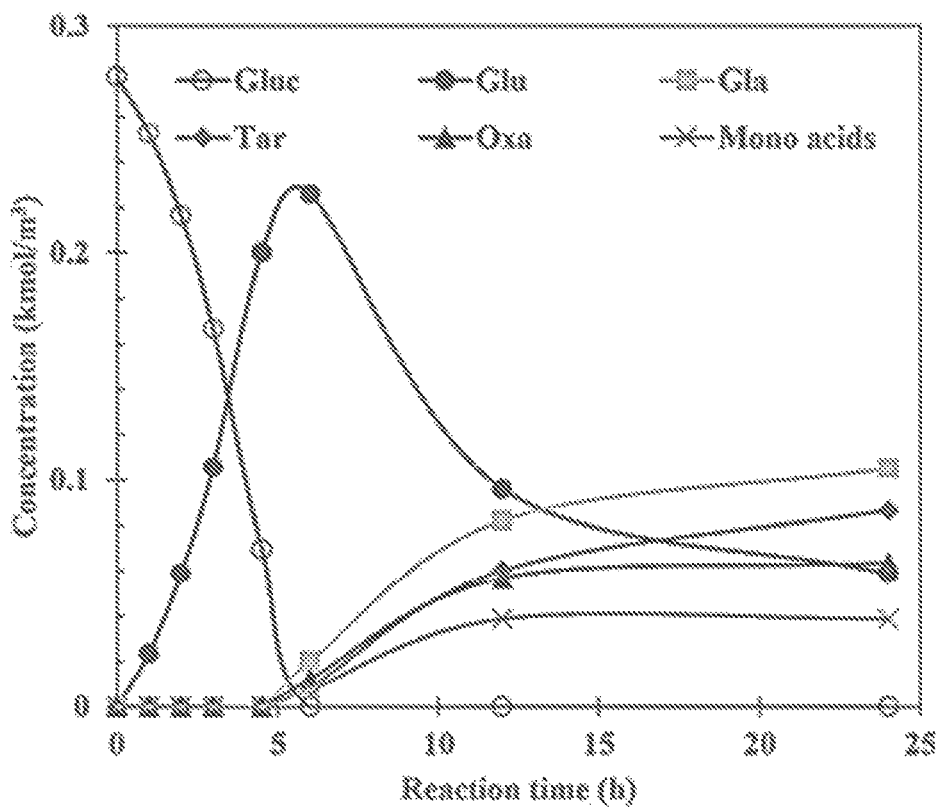
FIG. 25 depicts glucose concentration-time profiles on PtPd$_c$/TiO$_{2-a}$ catalyst at 45° C.

Glucose conversion profiles for PtPd$_c$ catalyst at 45° C. are shown in FIG. 25. It is found that glucose concentration decreased from 0.28 kmol/m$^3$ to zero within 6 hours reaction, suggesting a relatively lower glucose oxidation rate on PtPd$_c$ compared to PtPd$_a$ catalyst. Interestingly, before glucose was completely consumed, the concentration of aldaric acids was negligible, suggesting a similar glucose inhibition effect in secondary oxidation reactions as observed for both PtPd$_a$ and PtPd$_c$ catalysts. With regard to the concentration of secondary oxidation products, the formation of glucaric, tartronic and oxalic acids was only slightly lower on PtPd$_c$ catalyst at 24 hours compared to PtPd$_a$ catalyst.

The observed inhibition effect on PtPd$_a$ and PtPd$_c$ catalysts indicates that the C═O bond in glucose might interact/adsorb strongly on the bimetallic PtPd surface. This intriguing possibility might provide insights into the plausible reaction pathways. Hence, additional experiments were specifically designed.

Figure 26:
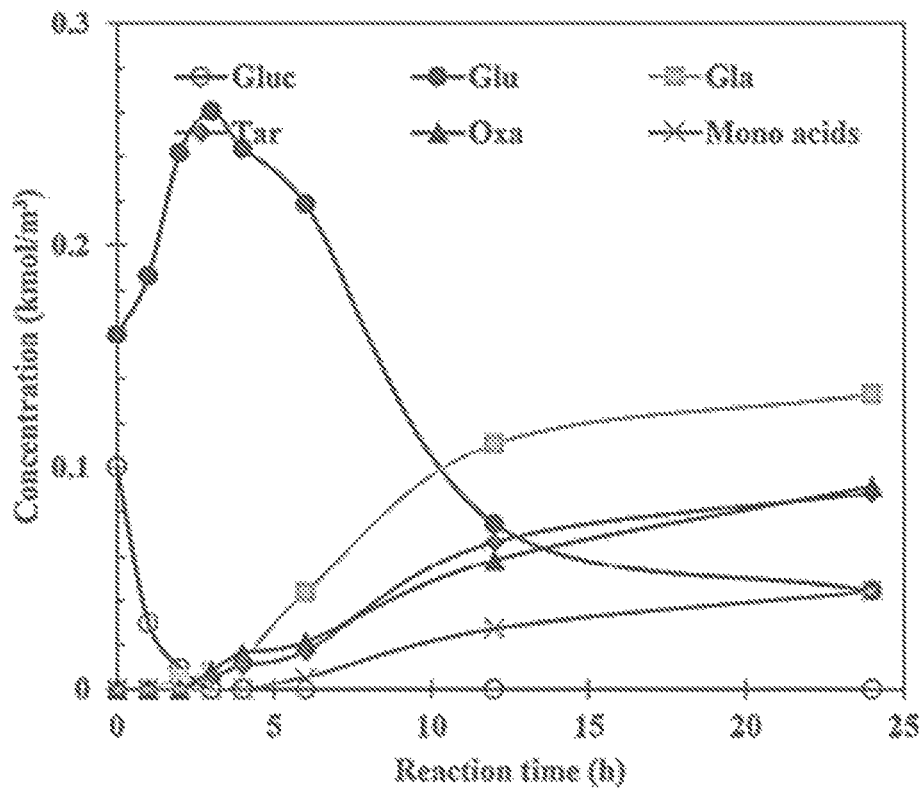
FIG. 26 depicts concentration-time profiles on PtPd$_c$/TiO$_{2-a}$ catalyst at 45° C. with glucose and sodium gluconate as starting materials.

(1) A control experiment was carried out with both glucose and sodium gluconate (molar ratio: 4/6) as the starting materials, simulating conditions for 60% conversion of glucose (FIG. 26). It is observed that glucose was completely converted less than 4 hours, while the concentration of gluconic acid also reached the peak value of 0.27 kmol/m$^3$ before starting to decline. Importantly, before glucose was consumed completely, the concentrations of glucaric, tartronic and oxalic acids were again found to be negligible.

Figure 27:
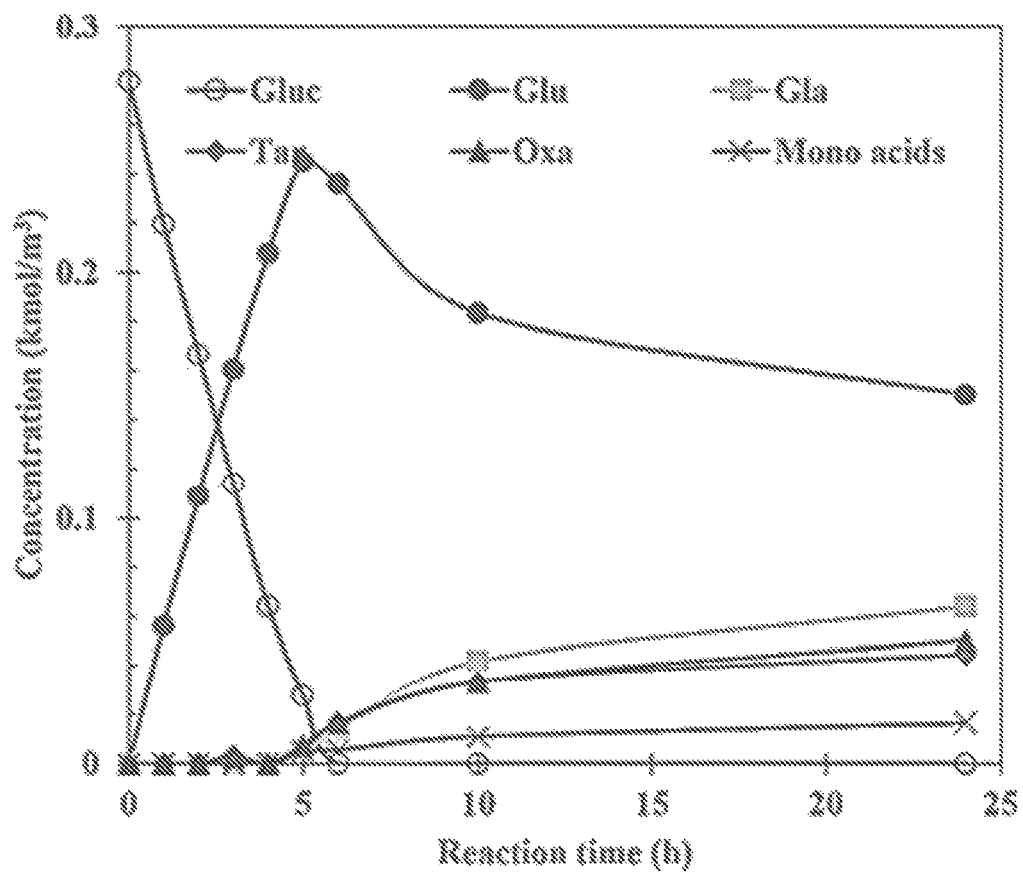
FIG. 27 depicts glucose concentration-time profiles on PtPd$_{a7}$/TiO$_{2-a}$ catalyst at 45° C.

(2) In addition, reaction profiles on bimetallic PtPd$_a$7 were also measured (see FIG. 27). For this experiment, the glucose concentration was found to decrease from initial 0.28 kmol/m$^3$ to zero within 6 hours reaction, suggesting primary oxidation rate is similar to PtPd$_c$ catalyst. However, the gluconic acid concentration only decreased from 0.26 to 0.16 kmol/m$^3$ within 24 hours' time. And the concentration of glucaric acid as well as tartronic and oxalic acid is only less than half of that obtained on both PtPd$_a$ and PtPd$_c$ catalysts within 24 hours reaction, indicating a significantly lower secondary oxidation rates on PtPd$_a$7 catalyst at 45° C.

Results in both (1) and (2) agree very well with the experimental findings in FIGS. 24 and 25, further confirming our hypothesis of the possible glucose inhibition effect on bimetallic PtPd catalysts. This effect actually favorably prevents the side reactions such as C—C cleavage of glucose in the reaction medium in the initial phase of the reaction. Thus, it is highly possible that C—C cleavage occurs significantly with gluconic acid in the reaction medium. This observed inhibition effect was not well understood in previous studies, where researchers found that the primary oxidation and C—C cleavage reactions occurred simultaneously as parallel reactions on metal catalyst surface. Considering the fact that monometallic Pt and Pd catalysts studied in the benchmark experiments displayed poor selectivity for glucaric acid, it appears that the combination of two metal species accelerates the formation of carboxylic RCO—O bond, not only promoting both primary and secondary oxidation reactions but also restraining C—C cleavage during the conversion of glucose.

Figure 28:
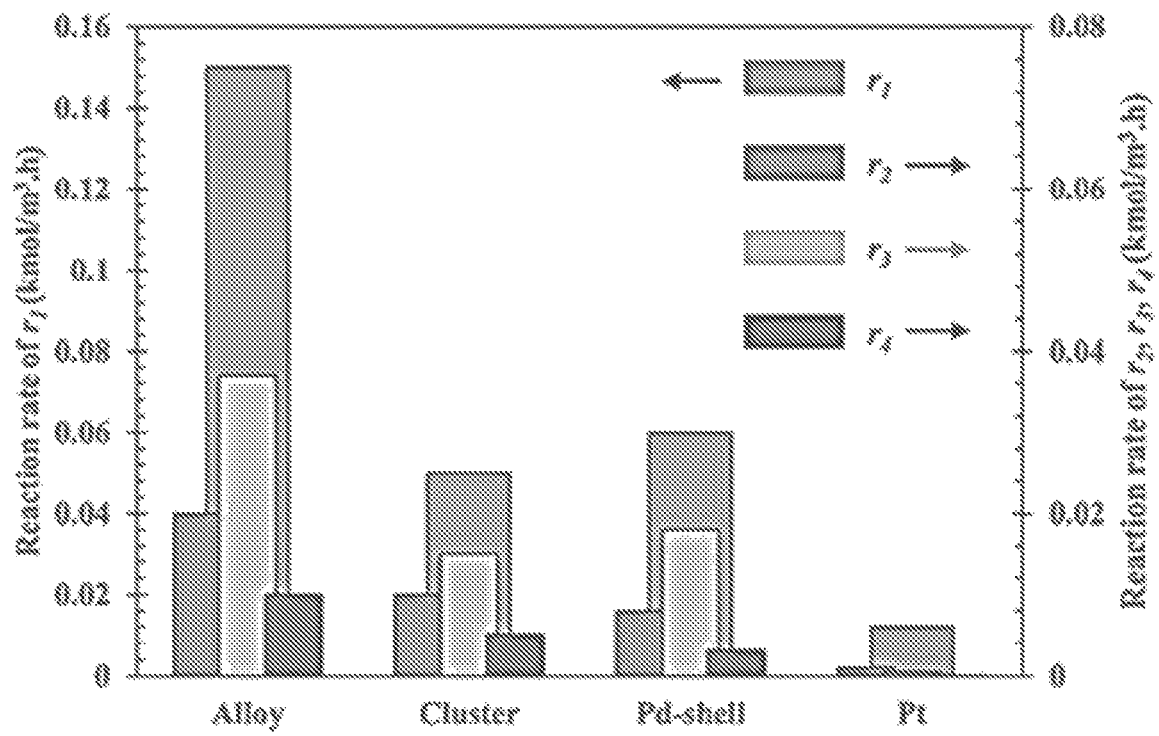
FIG. 28 depicts formation rates of gluconic acid (r1), glucaric acid (r2), tartronic and oxalic acids (r3) as well as monocarboxylic acids (r4, glyceric, lactic, glycolic and formic acids) at 45° C. on different Pt-based catalysts.

Furthermore, the formation rates of gluconic acid (r1, primary oxidation), glucaric acid (r2, secondary oxidation), tartronic and oxalic acids (r3, C—C cleavage and secondary oxidation) as well as monocarboxylic acids (r4, glyceric, lactic, glycolic and formic acids, C—C cleavage reactions) are plotted for bimetallic PtPd$_a$ (alloy), PtPd$_c$ (cluster-in-cluster) and PtPd$_a$7 (Pd shell) and monometallic Pt catalysts (FIGS. 24-26, Table 10). The reaction rates were measured when a particular species formation started in the reaction medium (initial formation rate). For example, r2 on the alloy structure (PtPd$_a$ catalyst) was calculated when glucaric acid formation started in reaction medium (from FIG. 24). As seen from FIG. 28 depicting formation rates of gluconic acid (r1), glucaric acid (r2), tartronic and oxalic acids (r3) as well as monocarboxylic acids (r4, glyceric, lactic, glycolic and formic acids) at 45° C. on different Pt-based catalysts (catalyst loading: 2 kg/m$^3$), the formation rate of gluconic acid (r1, orange bar) is significantly higher on alloy structure compared with others, suggesting that PtPd alloy nanoparticles promote the primary oxidation reaction of glucose in the reaction medium. As expected, the measured rate for r2 (green bar) is much lower than r1 on all investigated catalysts. In particular, r2 is approximately two times higher on PtPd alloy catalyst (PtPd$_a$) compared to other structures. The alloy catalyst also outperformed others in terms of r3 and r4.

Effects of Reaction Conditions.

Two additional experiments, one at 35° C., and another one with lower glucose concentration (0.167 kmol/m$^3$) at 45° C. were carried out on PtPd$_a$ catalyst in order to understand the effects of reaction conditions on glucose oxidation (using the same experimental conditions as described with respect to Table 11), as shown in Table 13.

TABLE 13

Glucose oxidation on PtPda alloy catalyst under different initial conditions

| # | Concentration (kmol/m3) | T (° C.) | Time (h) | X (%) | Selectivity (%) | | | | |
|---|---|---|---|---|---|---|---|---|---|
| | | | | | Glu | 5-k-Glu | Gla | Tar | Oxa | Others* |
| 1 | 0.277 | 35 | 12 | 100 | 77.2 | 3.1 | 8.4 | 3.2 | 1.2 | 0.9 |
| 2 | 0.277 | 35 | 24 | 100 | 55.6 | 0.1 | 22.2 | 10.8 | 3.1 | 6.1 |
| 3 | 0.277 | 35 | 72 | 100 | 21.1 | — | 44.3 | 17.4 | 5.3 | 9.1 |
| 4 | 0.167 | 45 | 6 | 100 | 69.2 | — | 11.0 | 9.9 | 3.6 | 5.9 |
| 5 | 0.167 | 45 | 12 | 100 | 33.6 | — | 22.1 | 14.4 | 6.6 | 7.8 |
| 6 | 0.167 | 45 | 24 | 100 | 8.9 | — | 41.2 | 19.9 | 6.3 | 8.8 |

As shown in Entry #1 of Table 13, small amounts of 5-keto-gluconic acid were detected in the reaction mixture whereas its concentration was negligible at 45° C. under otherwise similar reaction conditions (Table 11). The selectivity towards glucaric acid is only 8.4% after 12 hours, which is significantly lower than that at 45° C. (Entry #4 in Table 11). This observation implies that as reaction temperature decreases, the secondary oxidation rate (oxidation of gluconic acid) is slowed down considerably, suggesting relatively higher second step oxidation barriers compared with the first step oxidation. When the reaction was prolonged to 24 hours (Entry #2 of Table 13), 5-keto-gluconic acid disappeared with increasing selectivity to glucaric acid (22%) and tartronic acid (10.8%).

After 72 hours, gluconic acid selectivity decreased to approximately 21% while that towards glucaric and tartronic acids increased to 44.3% and 17.4%, respectively. The results at 35° C. and 45° C. indicate that the temperature, while influencing the reaction rates, has negligible effects on glucaric acid and tartronic acid selectivity on the $PtPd_a$ alloy catalyst.

Experimental results with lower initial glucose concentration are shown in Entries #4-#6 of Table 13. When we compare the results on $PtPd_a$ alloy catalyst in Entry #4 with FIG. 23, it is found that although glucose conversion was completed within 6 hours in both cases, the selectivities towards primary and secondary products are very different. Specifically, the selectivity of gluconic acid is 69% with 0.167 $kmol/m^3$ while this value is lower (55%) with 0.277 $kmol/m^3$ of initial glucose concentration. The difference indicates that the secondary reactions are more significant when glucose concentration is higher. In terms of secondary products, glucaric, tartronic and oxalic acid selectivities were 11%, 10%, and 3.6% (see Table 13), while these were 25%, 7%, and 4% respectively in the case shown in FIG. 23. When the reaction was prolonged to 24 hours (Entry #6), glucaric acid selectivity was increased to 41% with large amounts of tartronic and oxalic acids formation as co-products. This observation means that higher alkali to substrate ratio actually promotes further conversion of gluconic acid to lower aldaric acids via C—C cleavage.

Stability studies were also carried out on $PtPt_a/TiO_2$ catalyst at 45° C. and 0.1 MPa $O_2$, with results shown in Table 14, using the same reaction conditions used with respect to Table 11. Solid catalyst was recovered by centrifuge and washed with deionized water for six times prior to use in subsequent batch studies.

TABLE 14

Stability study on $PtPta/TiO_2$ catalyst at 45° C. and 0.1 MPa $O_2$

| Recycle # | Time (h) | X (%) | Selectivity (%) | | | | |
|---|---|---|---|---|---|---|---|
| | | | Glu | 5-k-Glu | Gla | Tar | Oxa | Others* |
| 1 | 24 | 100 | 28.7 | — | 40.9 | 15.6 | 4.5 | 7.8 |
| 2 | 24 | 100 | 27.9 | — | 42.1 | 14.3 | 3.6 | 6.7 |
| 3 | 24 | 100 | 29.1 | — | 39.5 | 16.4 | 2.2 | 6.0 |

After three recycles, the catalyst still displays complete glucose conversion with similar glucaric and tartronic acid selectivities. These results suggest that $PtPt_a/TiO_2$ catalyst is very stable under our reaction conditions.

Reaction Pathways.

Figure 29:
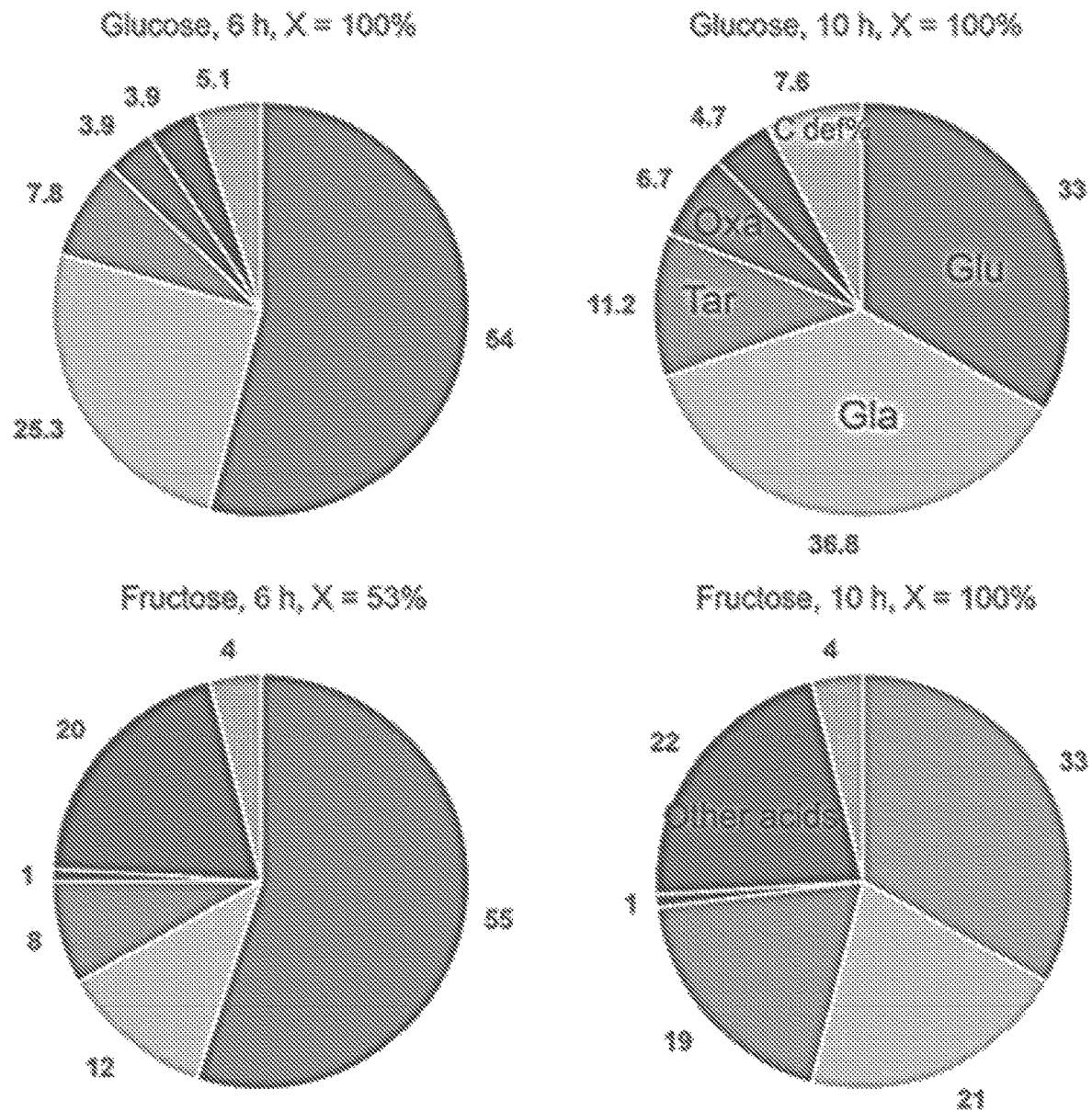
FIG. 29 depicts conversion and product distribution of glucose and fructose oxidation at 45° C. on PtPd$_d$/TiO$_{2-a}$ catalyst.

Based on concentration-time profiles, glucose displays a substrate inhibition effect for second step oxidation reactions as well as C—C cleavage (retro-aldolization) thus also affecting the selectivity pattern. In order to further understand this interesting behavior, out another set of control experiments was carried out with fructose, an isomer of glucose and obtained temporal conversion and selectivity data at 45° C. Results are depicted in FIG. 29 (Glu: gluconic acid; Gla: glucaric acid; Tar: tartronic acid; Oxa: oxalic acid; Other acids: glyceric, glycolic, lactic and formic acids; C def %: carbon deficit in the system).

The top two pie graphs in FIG. 29 present the conversion and product distribution data of glucose oxidation at 6 hours and 10 hours. Although glucaric acid formation was negligible at the beginning, due to the glucose inhibition effect, glucaric acid selectivity was enhanced from almost zero to 25%, from 3 hours to 6 hours (FIG. 23), and further to 37% within 10 hours.

Interestingly, we did not observe a similar substrate inhibition effect during fructose oxidation, as shown in the bottom two pie graphs in FIG. 29. Within 6 hours reaction, fructose only displays 53% conversion on $PtPd_a$ alloy catalyst at 45° C. Even before fructose was completely converted, other reactions such as C—C cleavage already occur. Notably, glucose was not detected in the reaction solution, indicating that once fructose slowly isomerized to glucose, oxidation occurred to consume it. As seen from the results during a 6 hour run, gluconic acid was still the dominant product during fructose conversion.

Only 12% glucaric acid selectivity was observed, suggesting that isomerization, primary oxidation as well as secondary oxidation reactions compete on $PtPd_a$ catalyst surface.

In sharp contrast to results with glucose as substrate, appreciable glyceric acid formation was observed during fructose conversion. This suggests that both retro-aldolization of fructose (C3-C3 cleavage) as well as further oxidation of the C3 intermediates are significant. These results support two of our hypotheses: (a) Inhibition induced by terminal C=O (aldose) surface species is more significant than secondary C=O (ketose) species during oxidation reactions. (2) Existence of secondary C=O bond in fructose favors facile C—C cleavage, although overall reaction rate is lower than glucose oxidation.

Glucose oxidation results of this work was compared with reported glycerol (a C3 sugar polyol) oxidation results over Pt-based catalysts. In the reference studies on glycerol oxidation, poor liquid-phase carbon balance (67%-85%) is reported when glycerol conversion was high (>30%, 50-90° C.). This is because once C=O bond (i.e. carbonyl species) was formed from glycerol, decarbonylation catalyzed by noble metals led to a side reaction generating CO, which either deactivated the catalysts or formed $CO_2$ (in the form of carbonate salt) in the reaction medium. These products could not be quantitatively assessed by HPLC. However, in our glucose oxidation study, improved liquid phase carbon balance (88-96%, see Tables 11 and 13, FIG. 29) was observed in most of the experiments, suggesting that decarbonylation of glucose is not significant compared with that of glycerol. The difference might be possibly caused by the different nature of C3 and C6 substrates.

Based on the conversion data shown in FIGS. 24-29, plausible reaction pathways for glucose and fructose conversion are proposed below:

Scheme 1. Plausible reaction pathways of glucose oxidation
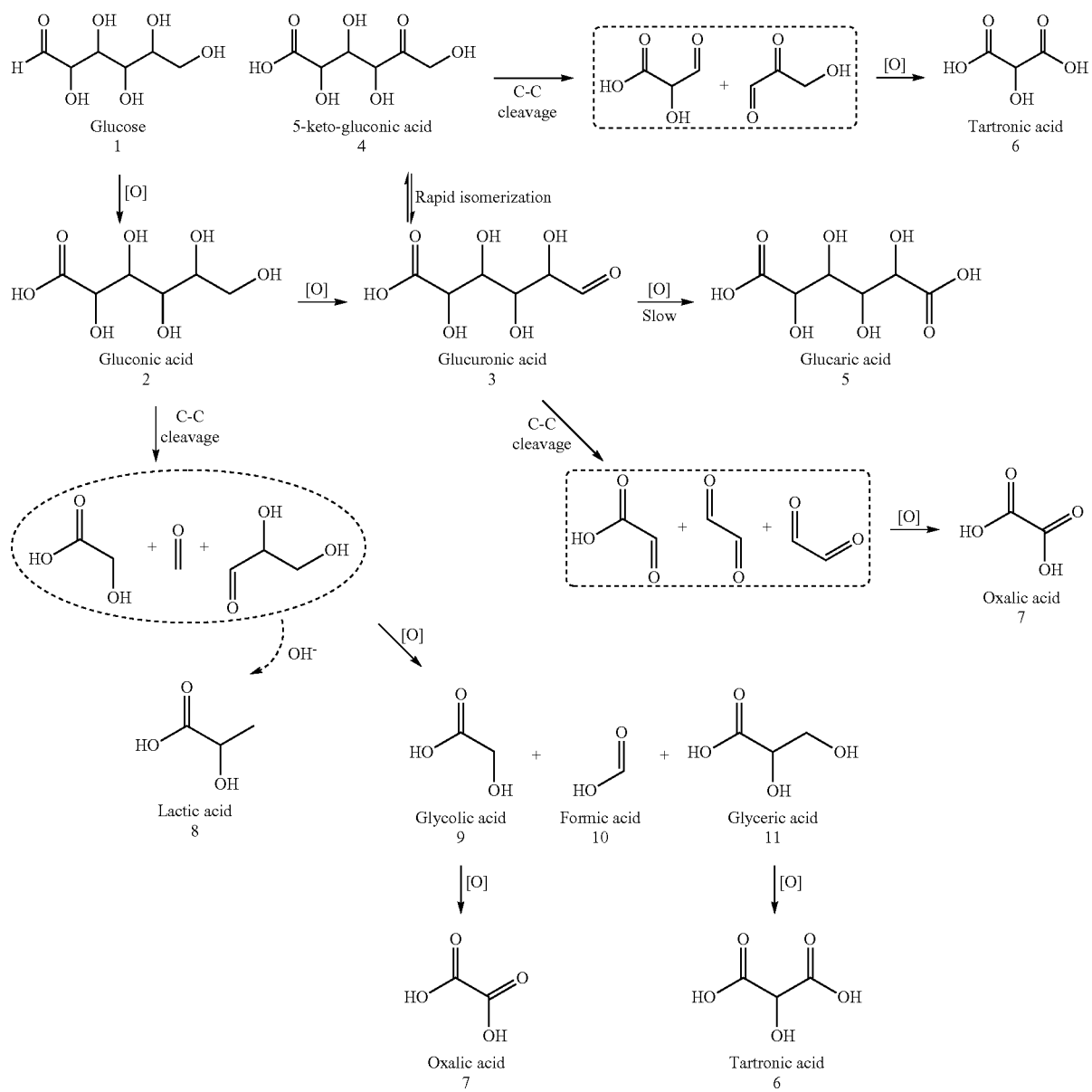
Scheme 2. Plausible reaction pathways of C-C cleavage of fructose
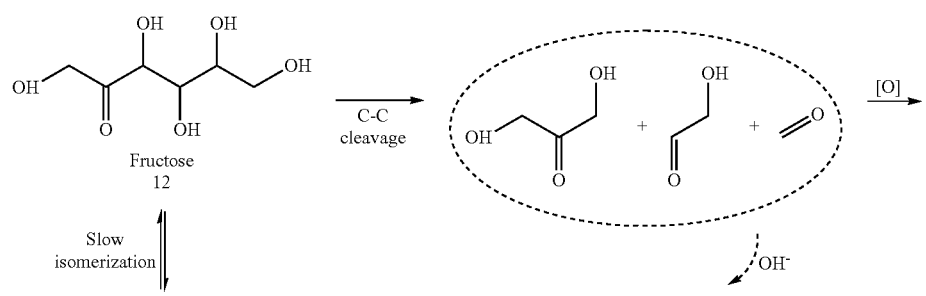

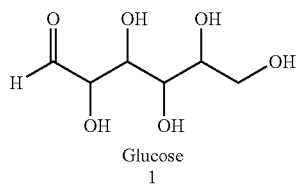

Glucose
1

-continued

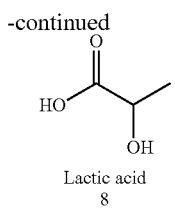

Lactic acid
8

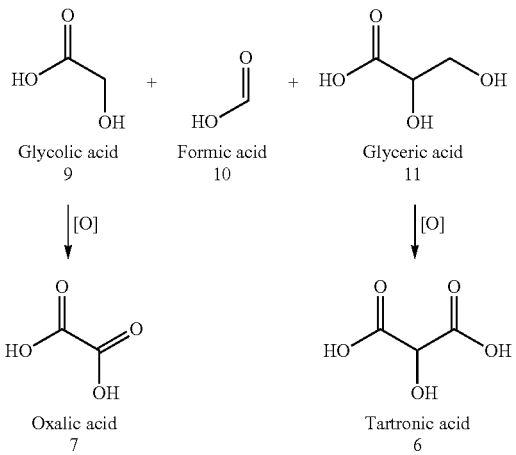

The foregoing describe the direct one-pot oxidation of glucose to glucaric acid (S=44%) with tartronic (S=15%), oxalic (S=6%) acids as co-products using a bimetallic PtPd alloy catalyst at 35-45° C., 0.1 MPa $O_2$. In particular, the structure-dependent oxidation activity of bimetallic PtPd nanoparticles was studied for glucose oxidation. $TiO_2$ supported PtPd catalysts exhibited synergistic activity compared with monometallic Pt and Pd ones for both primary and secondary oxidation of glucose at 45° C. and 0.1 MPa $O_2$. Surface characterization using TEM, SEM, XRD and UV-Vis of various bimetallic PtPd nanocatalysts further confirmed that the alloy structure showed the best oxidation activity among all the bimetallic structures. Concentration-time profiles on different bimetallic PtPd catalysts showed glucose inhibited the second step oxidation of gluconic acid in the reaction medium, with the secondary oxidation and C—C cleavage occurring after glucose was consumed.

Example 6: Oxidation of Glycerol to Dicarboxylic Acids Using Cobalt Catalysts

Materials.
All chemicals used in this paper were purchased from Sigma Aldrich.
Catalyst Preparation and Characterization.
(1) Co-precipitation. Co, Mg, and Al nitrate aqueous solution was prepared with predetermined Co/Mg/Al molar ratio of x/3/1 (x=0.15, 0.30), the total concentration of the three metal cations was 1 kmol/m³. This solution was denoted as A. Next, 0.25 kmol/m³ of NaOH and 0.8 kmol/m³ of $Na_2CO_3$ were mixed with DI water and this solution was denoted as B. In another beaker, 50 mL of DI water was introduced (Solution C). Then A and B were added to C dropwise and co-currently at room temperature, during which pH was maintained at 10-11. After aged for 24 hours, the slurry was filtered and dried in the oven overnight. Before tested for glycerol (GLY) oxidation, the sample was further calcined at 400° C. under air flow and activated at 300° C. under $H_2$ flow. The catalysts obtained from this method were denoted as $Co_x/Mg_3Al$-c. (2) Sol-gel method. Different from Co-precipitation method, Co species was added after Mg—Al hydroxide gel was formed. Particularly, solution A', containing only Mg and Al nitrate aqueous solution and solution B, were introduced to C dropwise and co-currently. After aged for 12 hours, Co nitrate aqueous solution (D) was added to the gel slowly and the slurry was aged for another 12 hours. Similarly to (1) Co-precipitation, the catalyst sample was filtered, dried, calcined and activated before oxidation tests. The catalysts were denoted as $Co_x/Mg_3Al$-s.

Figure 30A:
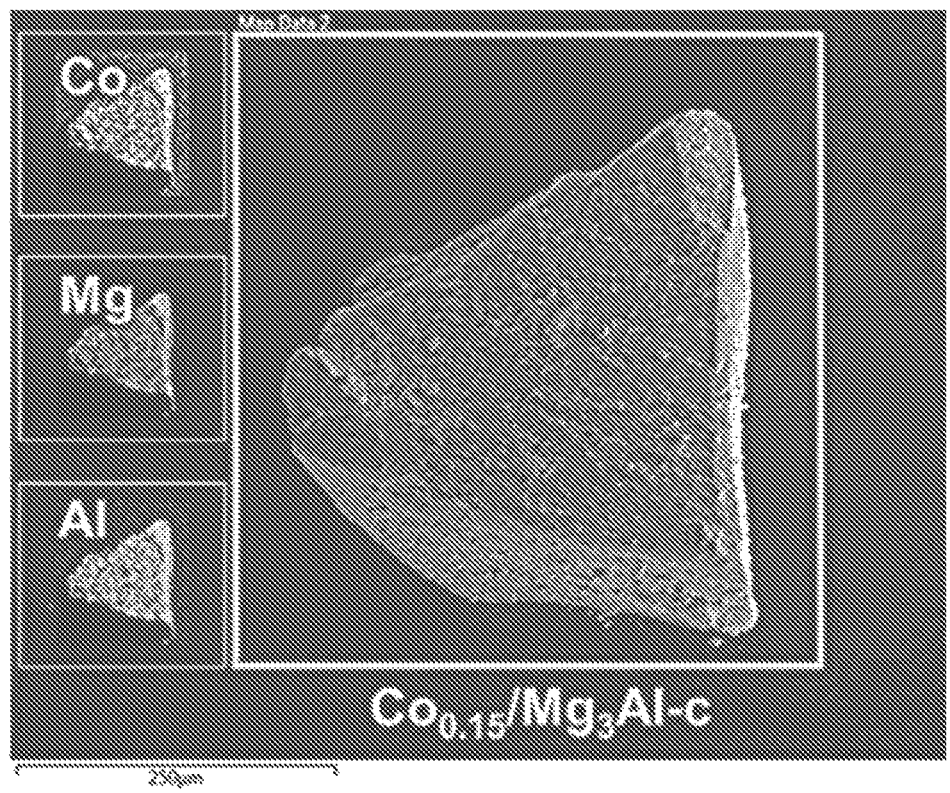
FIG. 30(a) depicts SEM images and EDX mapping of Co$_{0.15}$/Mg$_3$Al-c.
Figure 30B:
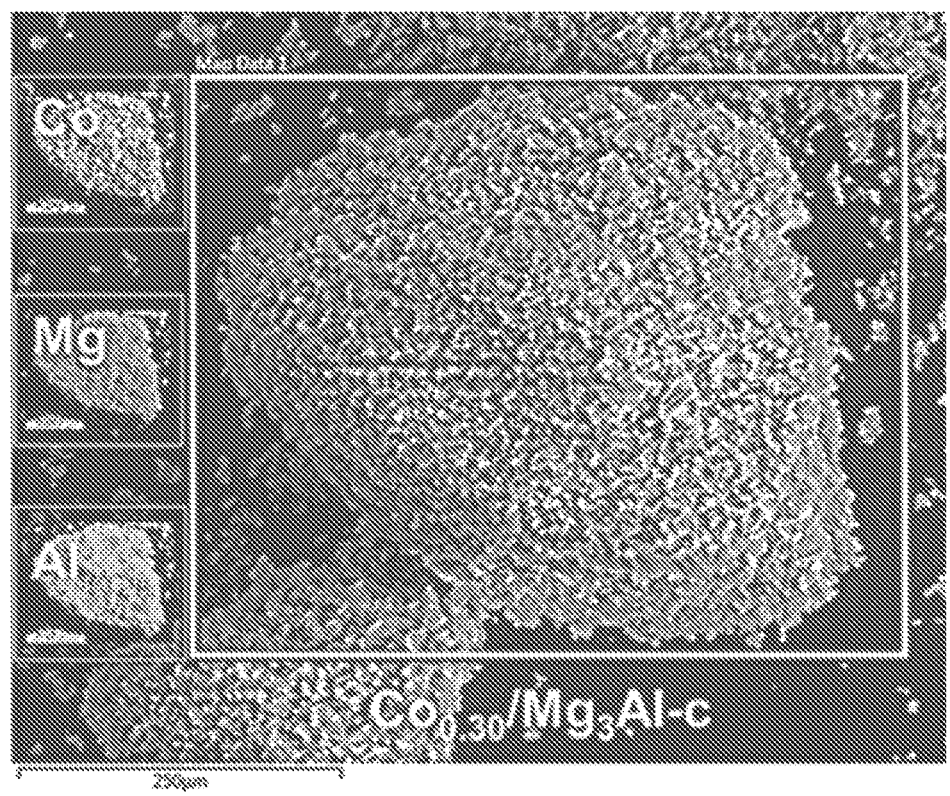
FIG. 30(b) depicts SEM images and EDX mapping of Co$_{0.30}$/Mg$_3$Al-c.
Figure 30C:
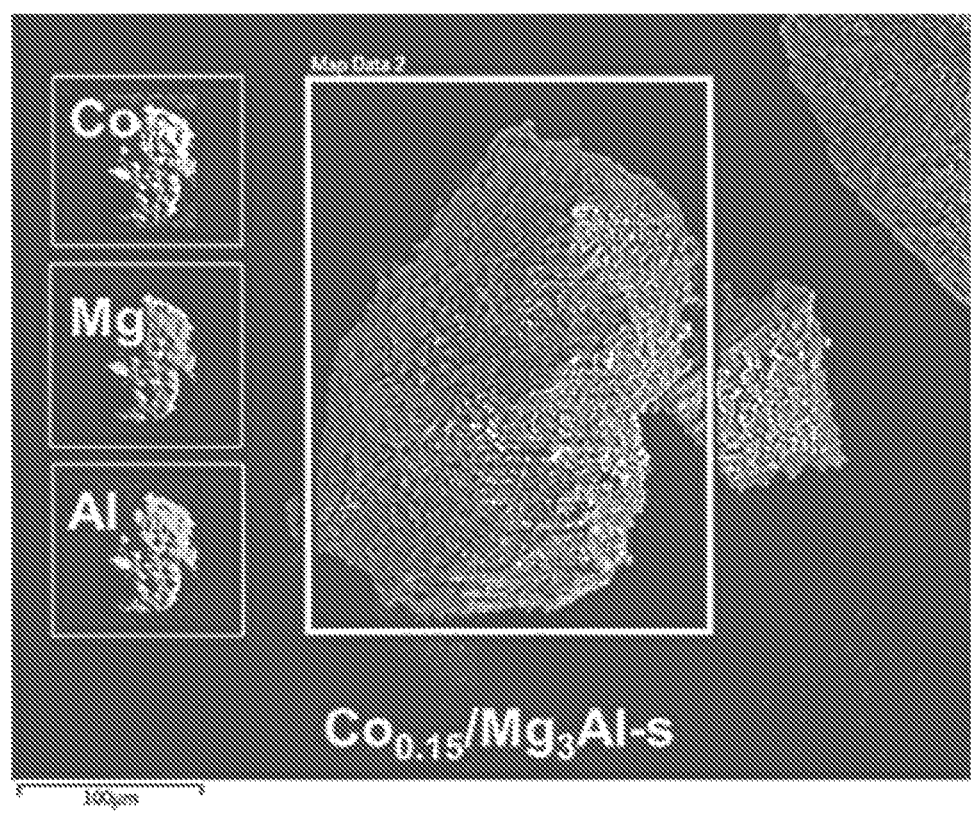
FIG. 30(c) depicts SEM images and EDX mapping of Co$_{0.15}$/Mg$_3$Al-s.

Surface characterization was carried out as described above. X-ray diffraction (XRD): This measurements was performed on a Bruker D8 powder diffractometer with a copper target ($CuK_\alpha$ radiation) operating at 40 kV and a current of 40 mA to analyze the crystal structures of materials. $CO_2$ temperature programmed desorption ($CO_2$-TPD): The basicity of Co catalysts was measured using AutoChem 2910 Instrument. In a typical measurement, solid catalyst samples were first dried at 120° C. for 1 hour and then saturated with $CO_2$ at 50° C., after which desorption tests were conducted at a ramping rate of 10° C. till 500° C. $CO_2$ signal was recorded by a thermal conductivity detector. Transmission electron microscopy (TEM): sample preparation and detailed procedures were similar to that described in the literature. Samples were prepared by suspending the solid catalyst in ethanol and agitating in an ultrasonic bath. 10 μL of catalyst sample was placed onto a copper mesh grid. The wet grid was allowed to air-dry for several minutes prior to examination under TEM. Scanning electron microscopy (SEM: a Versa 3D dual beam Scanning Electron Microscope/Focused Ion Beam (FEI, Hillsboro, Oreg., USA) with a silicon drift EDX detector (Oxford Instruments, X-Max, UK) was used to measure the surface morphology, elemental composition and distribution of metals. All the SEM data reported were obtained at an acceleration voltage of 15 kV, spot size 3.0 and the images were collected with an ET (Everhart Thornley) detector. The elemental mapping and energy spectrums were acquired with Aztec tools (Oxford Instruments, UK). SEM images of Co catalysts studied in this paper are shown in FIG. 30 (a) $Co_{0.15}$/$Mg_3Al$-c, (b) $Co_{0.30}$/$Mg_3Al$-c, and (c) $Co_{0.15}$/$Mg_3Al$-s.

Activity Tests.

Figure 31:
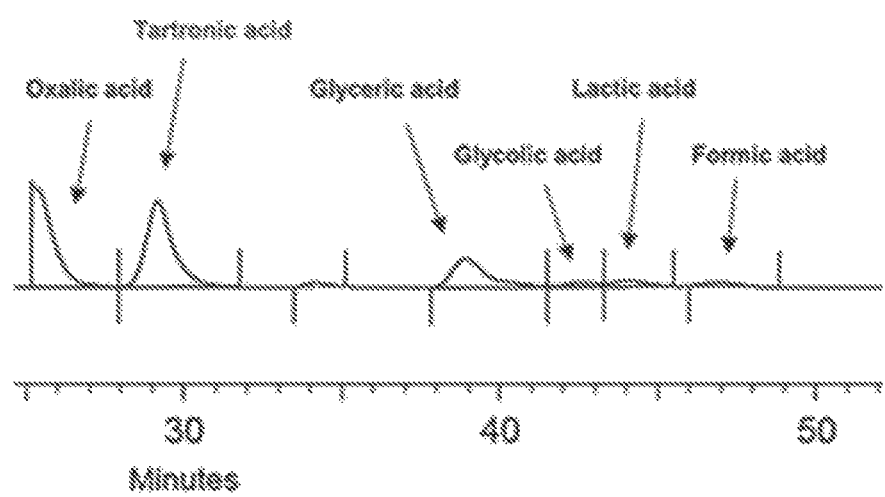
FIG. 31 depicts an example of HPLC results from glycerol oxidation using a copper/magnesium catalyst.

The procedures for aqueous phase oxidation (APO) of GLY tests are described here in brief. Typically, about 0.2 g of solid Co catalysts were added to 25 mL aqueous solution containing GLY and NaOH. GLY and NaOH concentration was 0.22 mol/L and 1.5 mol/L respectively. The reaction mixture was heated in a temperature controlled oil bath and heated up to reaction temperature (e.g. 55° C., 70° C.). Once the slurry reached reaction temperature, stirring rate was set at 1000 RPM, and $O_2$ was started to be introduced to the liquid by bubbling. During each batch experiment, approximately 0.5 mL of liquid samples was taken and acidified with $H_2SO_4$ solution before injected into HPLC (SH1011 column, 0.005 N $H_2SO_4$ solution as mobile phase). An example of HPLC analysis is shown in FIG. 31 in which the following conditions were used: Column: SH1011, oven temperature: 70° C., mobile phase: 0.005 N $H_2SO_4$ aqueous solution, flow rate: 0.2 mL/min. The concentration of GLY and oxidation products including glyceric, tartronic, lactic, oxalic, glycolic acids, were obtained for the calculation of conversion (X), selectivity (S), carbon balance (C %) and turnover frequency (TOF, in mol/$mol_{Co}$.h). Conversion is defined as the ratio of moles of GLY converted to that initially charged. Selectivity towards a specific product, tartronic acid for example, is defined as the ratio of total moles of carbon atom in this product generated during certain reaction time over that in converted GLY. Carbon balance is defined as the ratio of total amount of carbon in all products to that of converted GLY. TOF is defined as the amount of GLY converted over Co content in the reaction system per time.

Catalyst Characterization.

Co catalysts prepared by co-precipitation and sol-gel methods were characterized by XRD, $CO_2$-TPD, TEM and SEM techniques as show in FIGS. 32(a)-(d). In particular, TEM images of $Co_{0.15}$/$Mg_3Al$-c (FIG. 32(a)) and $Co_{0.30}$/$Mg_3Al$-c (FIG. 32(b)) catalysts reveal the nature of their surface morphologies. Neither catalyst sample exhibited detectable Co nanoparticles, while both of them exhibit several thin layers with several folded structures. EDX in FIGS. 1 (a) and (b) show that Co, Mg and Al element are well dispersed in the samples. Interestingly, for $Co_{0.15}$/$Mg_3Al$-s catalyst [FIG. 32(c)], which was prepared by sol-gel method, the layer structure is still dominant but the extent of folding is significantly higher than previous two. This observation implies that the addition of Co species to the $Mg_3Al(OH)_y(CO_3)_z$ gel also influence the surface morphology of final catalyst sample. EDX analysis of $Co_{0.15}$/$Mg_3Al$-s also confirms the uniform distribution of Co element in the catalyst. SEM images in FIG. 30 also support this point. In addition, EDX bulk analysis and ICP measurement reveal the actual Co/Mg/Al molar ratios in $Co_{0.15}$/$Mg_3Al$-c, $Co_{0.30}$/$Mg_3Al$-c and $Co_{0.15}$/$Mg_3Al$-s catalysts are 1.89/30.55/9.37, 3.76/24.78/8.90 and 1.49/29.6/10.5, respectively. These data further confirm that the strong interaction with colloidal structures in the aqueous phase enhance the deposition of Co species within or on the surface of MgO and $Al_2O_3$ network.

Figure 32A:
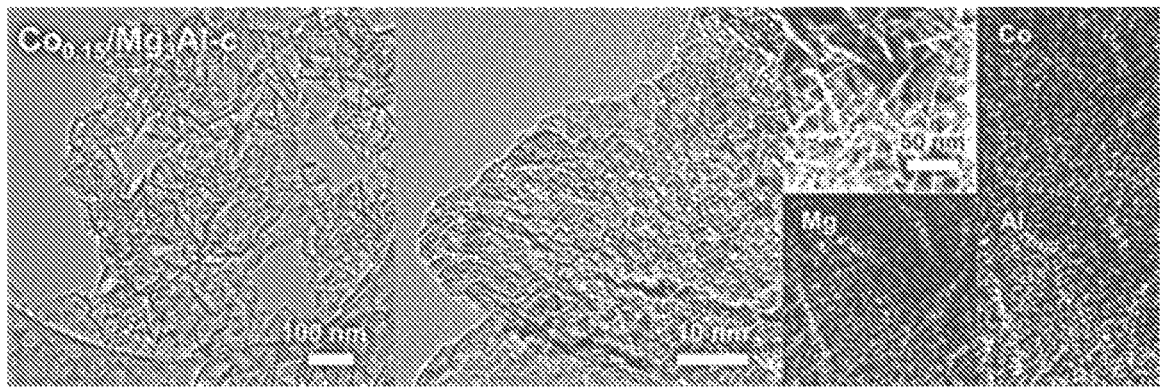
FIG. 32(a) depicts TEM images and EDX mapping of fresh Co$_{0.15}$/Mg$_3$Al-c.
Figure 32B:
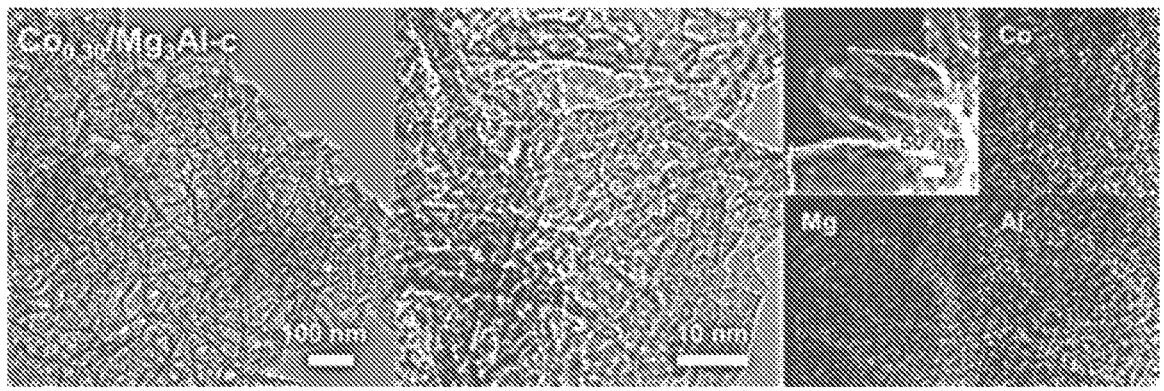
FIG. 32(b) depicts TEM images and EDX mapping of fresh Co$_{0.30}$/Mg$_3$Al-c.
Figure 32C:
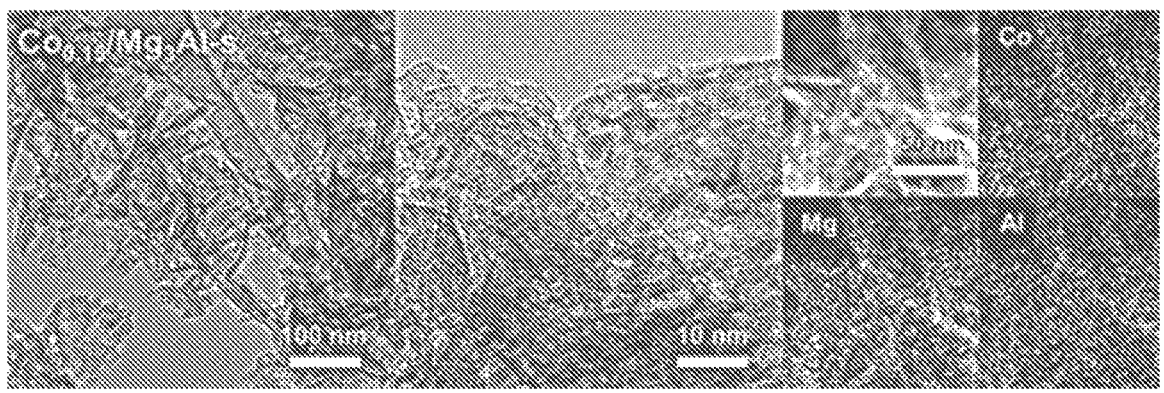
FIG. 32(c) depicts TEM images and EDX mapping of fresh Co$_{0.15}$/Mg$_3$Al-s.
Figure 32D:
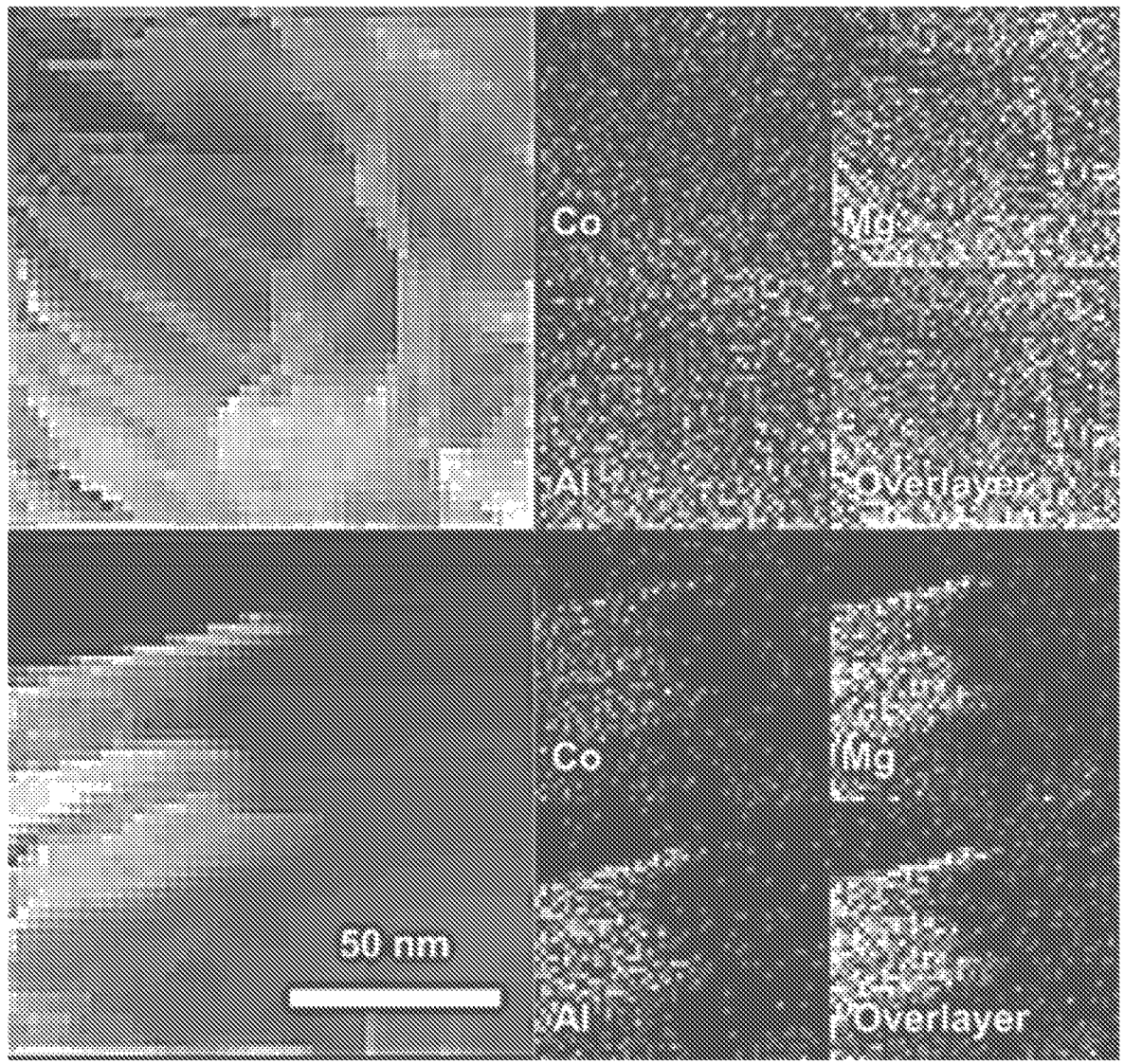
FIG. 32(d) depicts STEM and element mapping of used Co$_{0.15}$/Mg$_3$Al-s catalysts.

STEM images and element mapping of used $Co_{0.15}$/$Mg_3Al$-s catalyst are shown in FIG. 32(d). An observable morphological change is found in this sample, in comparison with fresh $Co_{0.15}$/$Mg_3Al$-s catalyst. We find that several thin layered species were peeled off from bulky phases and tend to form folded structures. Element mapping of two selected regions [shown in FIG. 32(d)] confirm that there is no Co agglomeration in used catalyst sample, suggesting good structural stability after recycle studies.

Figure 33:
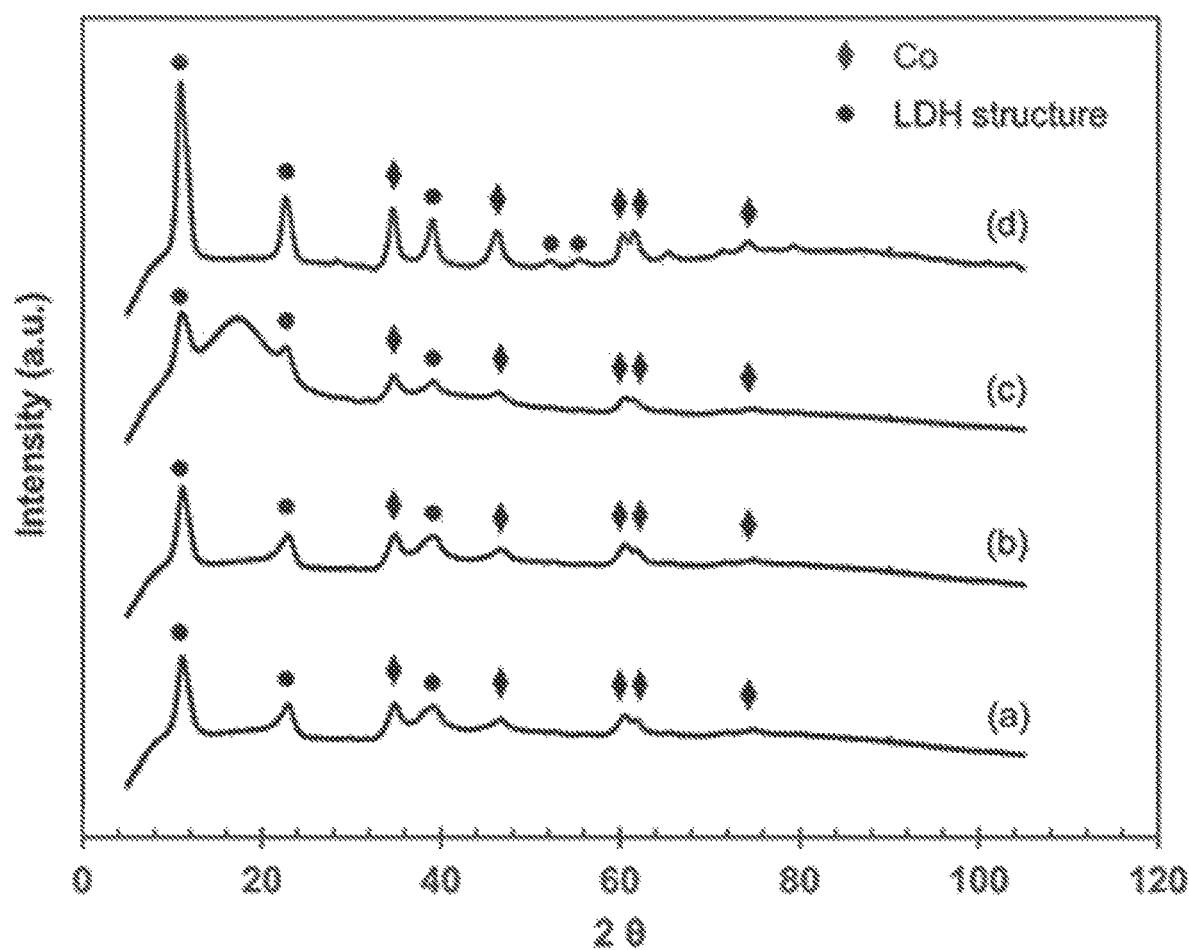
FIG. 33 depicts XRD of fresh (a) Co$_{0.15}$/Mg$_3$Al-c, (b) Co$_{0.30}$/Mg$_3$Al-c and (c) Co$_{0.15}$/Mg$_3$Al-s and (d) used Co$_{0.15}$/Mg$_3$Al-s catalysts.

To further illustrate the surface species of all Co catalyst samples, x-ray diffraction (XRD) powder analysis was conducted. In particular, as shown in FIG. 33 powder diffraction patterns of (a) $Co_{0.15}$/$Mg_3Al$-c, (b) $Co_{0.30}$/$Mg_3Al$-c, (c) $Co_{0.15}$/$Mg_3Al$-s and used (d) $Co_{0.15}$/$Mg_3Al$-s samples are shown. For the four solid samples, characteristic peaks for [311], [400], [511], [220] and [220] for Co species at 360, 45°, 60°, 62°, and 75° were observed. Compared to $Co_{0.15}$/$Mg_3Al$-c and $Co_{0.30}$/$Mg_3Al$-c, $Co_{0.15}$/$Mg_3Al$-s catalysts display relatively wider and lower weak peaks at 36°, 45°, 60°, and 62°, suggesting that the crystalline size of Co is small on this sample. For MgO and $Al_2O_3$ phases, sharp peaks in all samples at 10°, 22°, and 49° confirm the existence of [003], [006] and [200] crystals of layered double hydrotalcite ($Mg_3AlO_{4.5}$) structure. However, the wide peak at 160 indicate that the spinal $MgAl_2O_4$ structure exist in $Co_{0.15}$/$Mg_3Al$-s catalyst, while this peak is not present in other catalyst samples. This suggests that the spinal structure tend to form, when Co species are not present with Mg and Al during precipitation processes. Intensity of all peaks for Co, Mg, and Al species in $Co_{0.15}$/$Mg_3Al$-s sample is enhanced and shapes become sharper, which implies that the crystal sizes increase significantly after recycle studies. In addition, the peaks at 520 and 57° of used $Co_{0.15}$/$Mg_3Al$-s sample suggest the formation of thin layered $Mg_3AlO_{4.5}$ [1011] and [1013] structures with 8.98 Å spacing (Chem. Commun., 2008, 5188-5190) after recycle studies. This implies that then layered double structures start to peel from the original bulky structures, which is well agreed with the observation from STEM images.

Figure 34:
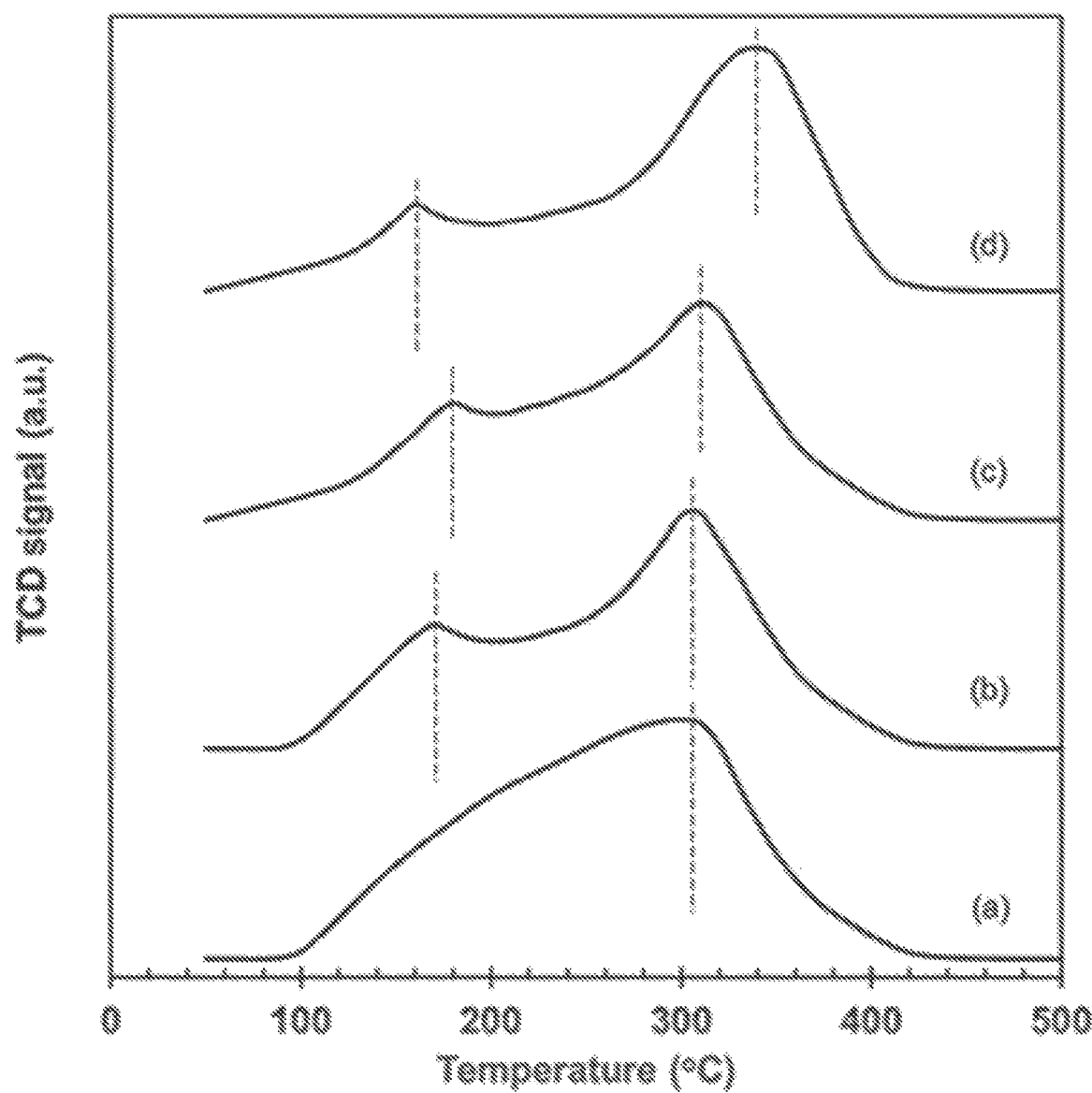
FIG. 34 depicts CO$_2$-TPD of fresh (a) Co$_{0.15}$/Mg$_3$Al-c, (b) Co$_{0.30}$/Mg$_3$Al-c and (c) Co$_{0.15}$/Mg$_3$Al-s and (d) used Co$_{0.15}$/Mg$_3$Al-s catalysts.

To further understand the possible interaction, $CO_2$-TPD characterization was also conducted to measure the surface basicity of different Co catalysts, the results of which are shown in FIG. 34 which depicts $CO_2$-TPD of fresh (a) $Co_{0.15}$/$Mg_3Al$-c, (b) $Co_{0.30}$/$Mg_3Al$-c and (c) $Co_{0.15}$/$Mg_3Al$-s and (d) used $Co_{0.15}$/$Mg_3Al$-s catalysts.

Oxidation of Glycerol.

The conversion and selectivity of GLY oxidation on $Co_{0.15}$/$Mg_3Al$-c, $Co_{0.30}$/$Mg_3Al$-c and $Co_{0.15}$/$Mg_3Al$-s catalysts was studied. The results are shown in Table 15.

TABLE 15

Glycerol oxidation on solid cobalt catalysts at 70° C.

| Entry# | Catalyst | Time (h) | X (%) | S (%) TAR | GLYA | OXA | Others |
|---|---|---|---|---|---|---|---|
| 1 | $Co_{0.15}$/$Mg_3Al$-c | 6 | 16.1 | 32.3 | 58.1 | 4.0 | 5.2 |
| 2 | $Co_{0.30}$/$Mg_3Al$-c | 6 | 21.7 | 38.0 | 52.8 | 3.1 | 2.0 |
| 3 | $Co_{0.15}$/$Mg_3Al$-s | 6 | 47.0 | 36.7 | 49.1 | 4.2 | 3.4 |
| 4 | $Co_{0.1}$/$Mg_3Al$-c | 24 | 100 | 46.9 | 29.2 | 13.4 | 4.3 |
| 5 | $Co_{0.30}$/$Mg_3Al$-c | 24 | 100 | 45.4 | 28.8 | 16.2 | 7.6 |
| 6 | $Co_{0.15}$/$Mg_3Al$-s | 24 | 100 | 63.5 | 2.1 | 24.0 | 3.8 |

Experimental conditions: 0.5 g glycerol, 1.5 g NaOH, 25 mL, 0.2 g solid catalysts. Others: lactic, glycolic and formic acids.

At 70° C., $Co_{0.6}$/$Mg_3Al$-c catalyst exhibits a 16% conversion within 6 hours reaction (Entry #1 in Table 15), the selectivity towards glyceric acid (GLYA), tartronic acid (TAR) and oxalic acid (OXA) being 58%, 32% and 4% respectively. As more Co content present in solid catalysts, $Co_{0.30}$/$Mg_3Al$-c (Entry #2) shows 22% conversion and 53%, 38%, and 3% selectivity towards these acids after 6 hours. Other carboxylic acids, including lactic, glycolic and formic acids account for approximately 2%-5% in selectivity. When catalysts were prepared using sol-gel method instead of co-precipitation, we find that the catalyst performances were significantly improved. As seen in Entry #3, GLY conversion on $Co_{0.15}/Mg_3Al$-s catalyst is 47%, about 3-fold higher than $Co_{0.15}/Mg_3Al$-c, although selectivity to GLYA, TAR, and OXA is similar to the previous two catalysts. Catalytic activity measured on $Co_{0.15}/Mg_3Al$-c and $Co_{0.30}/Mg_3Al$-c catalysts are 0.88 mol/$mol_{Co}$.h and 0.64 mol/$mol_{Co}$.h at 70° C., respectively. In contrast, $Co_{0.15}/Mg_3Al$-s exhibits a remarkable 3.0 mol/$mol_{Co}$.h. These results suggest that catalysts prepared by sol-gel method show better oxidation performances than the ones from co-precipitation method.

When reaction time prolonged from 6 hours to 24 hours, GLY conversion is found to be 100% on all three catalysts, the selectivity towards TAR is however different. Specifically, both $Co_{0.15}/Mg_3Al$-c (Entry #4 in Table 15) and $Co_{0.30}/Mg_3Al$-c (Entry #5) lead to 45%-47% TAR selectivity, while on $Co_{0.15}/Mg_3Al$-s catalyst (Entry #6) it is 63%. In addition, GLYA selectivity is about 29% on $Co_{0.15}/Mg_3Al$-c and $Co_{0.3}/Mg_3Al$-c catalysts. But this value is much lower on $Co_{0.15}/Mg_3Al$-s catalyst (2%). For OXA, the selectivity is 16% on $Co_{0.15}/Mg_3Al$-c and $Co_{0.3}/Mg_3Al$-c catalysts, while it is higher (24%) in the presence of $Co_{0.15}/Mg_3Al$-s. Selectivity towards lactic, glycolic and formic acids is also relatively higher on $Co_{0.15}/Mg_3Al$-s catalyst.

Figure 35A:
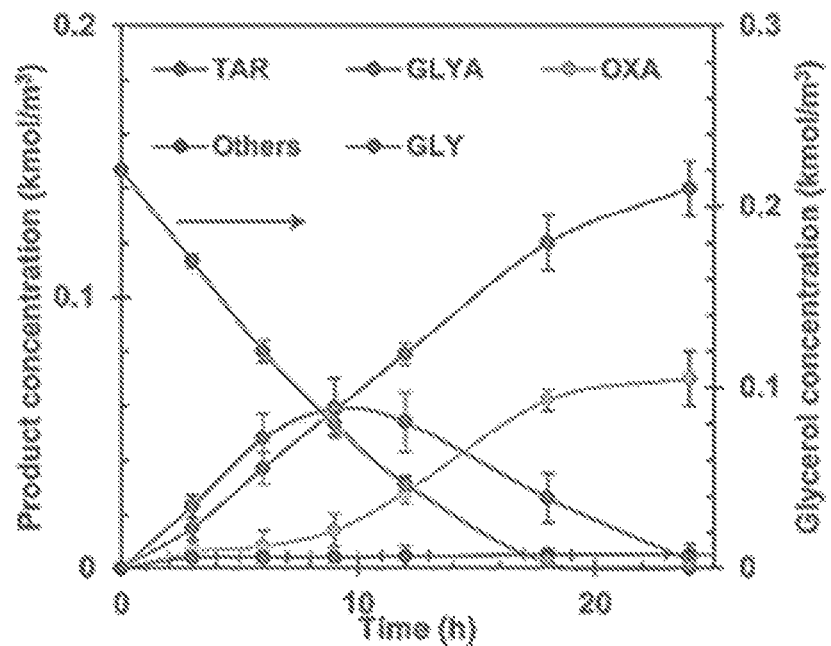
FIG. 35(a) depicts concentration-time profiles of glycerol oxidation on Co$_{0.15}$/Mg$_3$Al-s catalyst at 70° C.

Further experiments on $Co_{0.15}/Mg_3Al$-s catalyst were carried out and substrate and product concentration were collected at different reaction time at 70° C. and 55° C. with other experimental details remaining the same. Results are shown in FIG. 35 at (a) 70° C. and (b) 55° C. As seen from FIG. 35(a), GLY concentration decreases from 0.22 kmol/$m^3$ to 0.12 kmol/$m^3$ within 6 hour reaction time. The concentration GLYA increases from zero at the beginning to a maximum value of 0.058 kmol/$m^3$ at 9 hours then decreases to almost zero within 24 hours reaction. For TAR, its concentration increases slowly at the beginning then enhanced to approximately 0.14 kmol/$m^3$ at 24 hours, suggesting that secondary oxidation (oxidation of GLYA) becomes dominant along with reaction time. In another parallel reaction, we find that OXA formation rate is very low when GLA concentration is high, but its concentration is enhanced significantly after 10 hours. This phenomenon indicates that C—C cleavage reaction is another major reaction when GLA is consumed in the reaction medium.

Figure 35B:
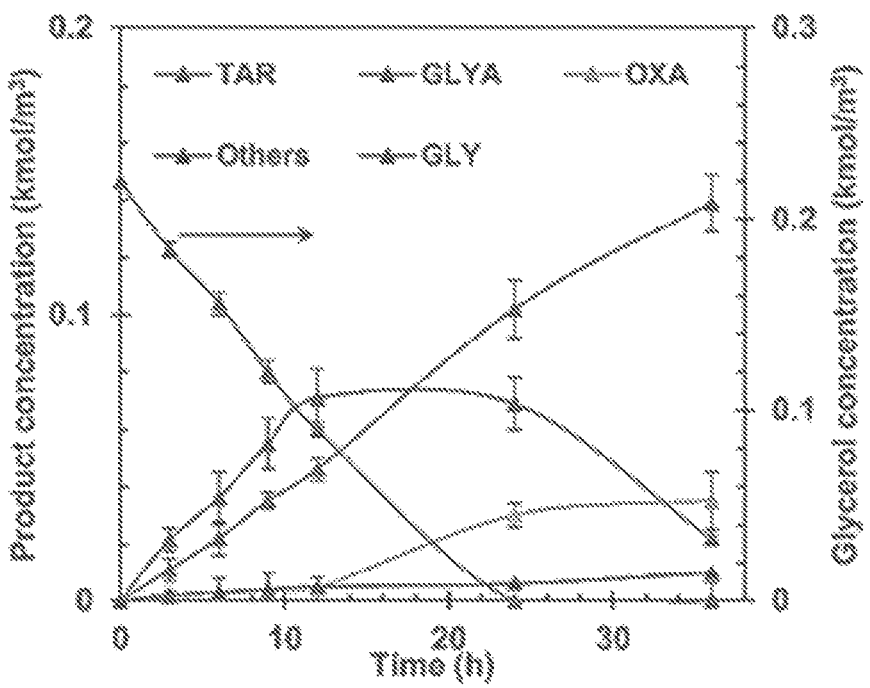
FIG. 35(b) depicts concentration-time profiles of glycerol oxidation on Co$_{0.15}$/Mg$_3$Al-s catalyst at 55° C.

In comparison, as shown in FIG. 35(b) at 55° C., glycerol concentration decreases to about 0.10 kmol/$m^3$ after 6 hours reaction. The peak value of GLYA concentration is about 0.55 kmol/$m^3$ around 18 hours reaction, after which it decreases to 0.022 kmol/$m^3$ after 36 hours. TAR concentration increases gradually with reaction time, while the overall OXA concentration is obviously much lower than at 70° C.

Possible Reaction Pathways.

Figure 36A:
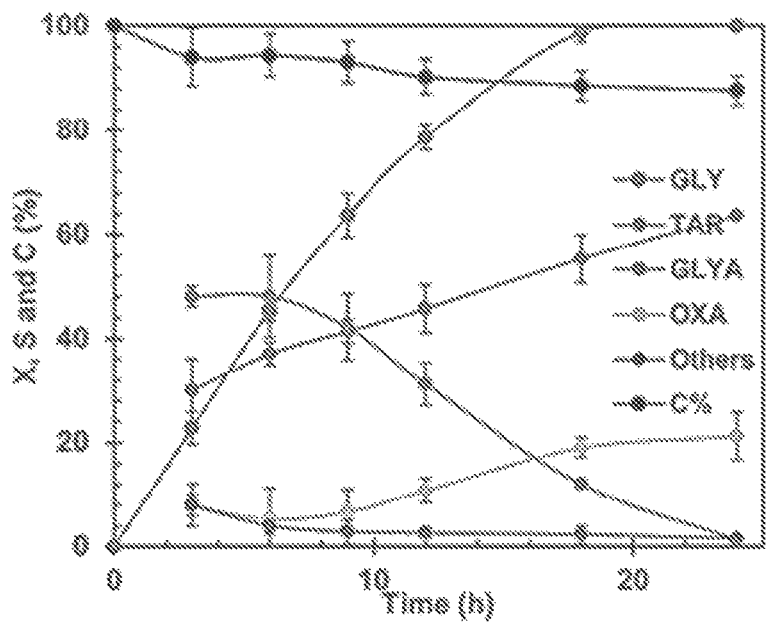
FIG. 36(a) depicts a conversion/selectivity/carbon balance vs time profiles of glycerol oxidation on Co$_{0.15}$/Mg$_3$Al-s catalyst at 70° C.
Figure 36B:
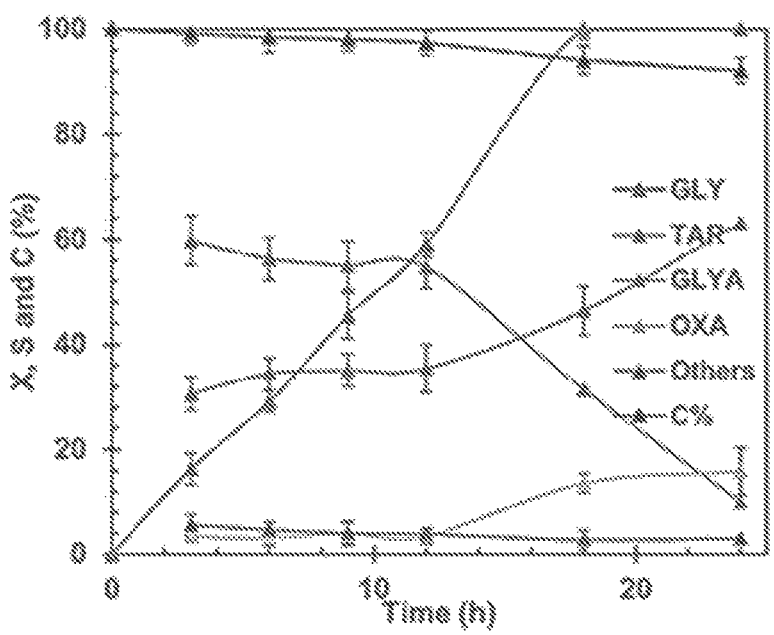
FIG. 36(b) depicts a conversion/selectivity/carbon balance vs time profiles of glycerol oxidation on Co$_{0.15}$/Mg$_3$Al-s catalyst at 55° C.

Under both reaction temperatures, the concentration of OXA (a $C_2$) is relatively low at the beginning but undergoes a quick increase once GLYA (a $C_3$) concentration start to decrease. This phenomenon suggests that OXA might be generated from further reaction of GLYA. Correspondingly, a $C_1$ species should also form at the same time. However, the concentration of formic acid (in "Others") is always negligible through the whole reaction process, which appears to be inconsistent with other experimental findings. Conversion (X), selectivity (S) and carbon balance (C) were plotted vs reaction time for (a) 70° C. and (b) 55° C. in FIG. 36. FIG. 36(a) demonstrates that glycerol conversion increases to 65% within 9 hours reaction at 70° C., where GLYA selectivity is almost constant. After 9 hours, there exists a significant decrease in GLYA selectivity while both TAR and OXA selectivity undergo an obvious increase. The selectivity towards glycolic and formic acids ("Others") is negligible throughout the whole reaction time. The total C % decreases from 100% at the beginning to approximately 86% after 24 hours. Therefore, the missing C % might result from decarboxylation of GLYA.

Figure 37:
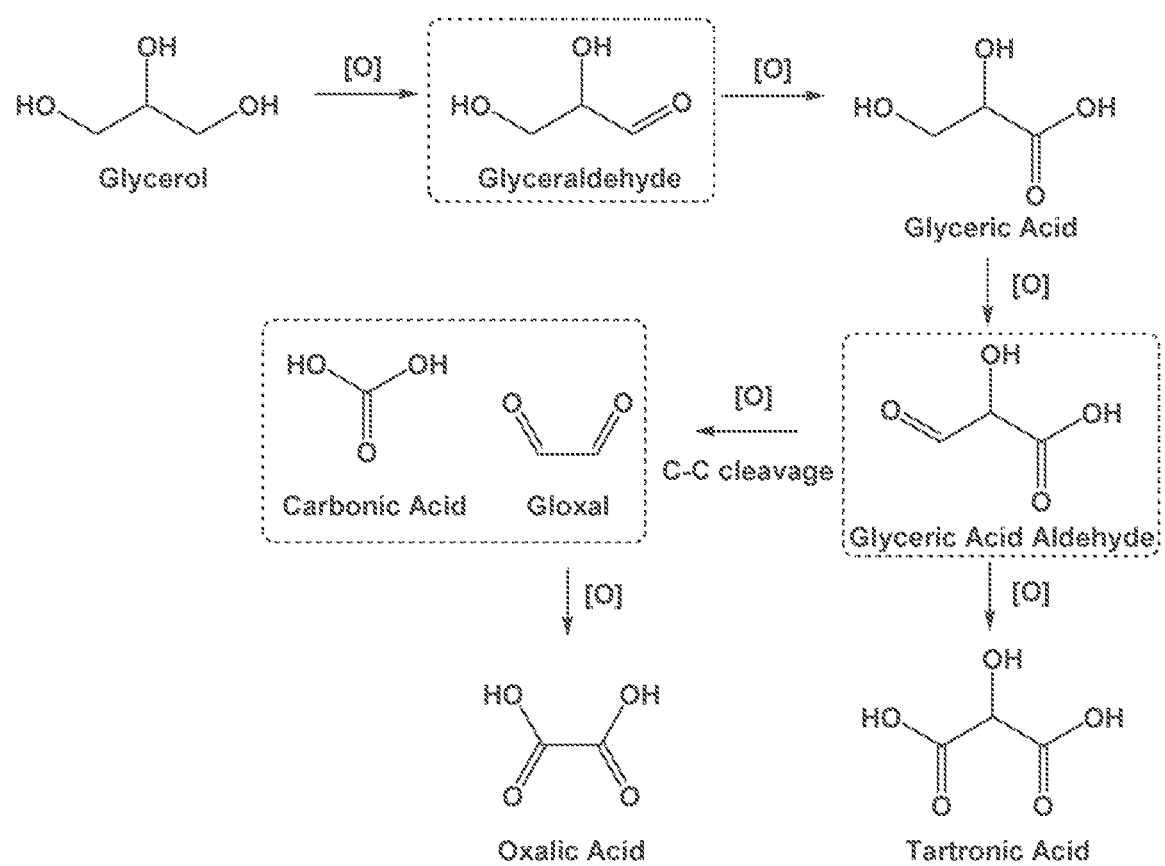
FIG. 37 depicts a plausible reaction pathways for tartronic and oxalic acids formation from glycerol.

A similar selectivity trend with time is also observed at 55° C., although the selectivity to OXA and C % deficit is not as significant as at 70° C. In both cases, the final TAR selectivity is approximately 63%, although after different reaction time. Based on the product distribution shown in FIGS. 35 and 36, plausible reaction pathways of GLY oxidation to TAR are shown in FIG. 37, primary oxidation of glycerol may lead to the formation of GLYA in presence of Co catalysts, while secondary oxidation to TAR also occurs simultaneously. As more GLYA formed in aqueous phase, C—C cleavage, a parallel reaction to secondary oxidation becomes significant. Therefore OXA ($C_2$ species) starts to form. Due carboxylation reactions, one $C_1$ is lost to carbonate. As products from other side reactions, combined selectivity towards lactic, glycolic and formic acids is almost negligible.

$Co_{0.15}/Mg_3Al$-s catalyst was also tested for glucose oxidation at 70° C. and 0.1 MPa $O_2$. Complete conversion was obtained after 10 hours reaction time with major products including TAR (S: 29%), GLYA (19.4%), gluconic acid (9.5%), glucaric acid (11.1%) and other monocarboxylic acids (lactic acid, glycolic acid, formic acid: 19.5%). This result shows that the proposed Co catalysts can be effective in converting other cellulosic feedstocks to value-added DCAs.

Figure 38:
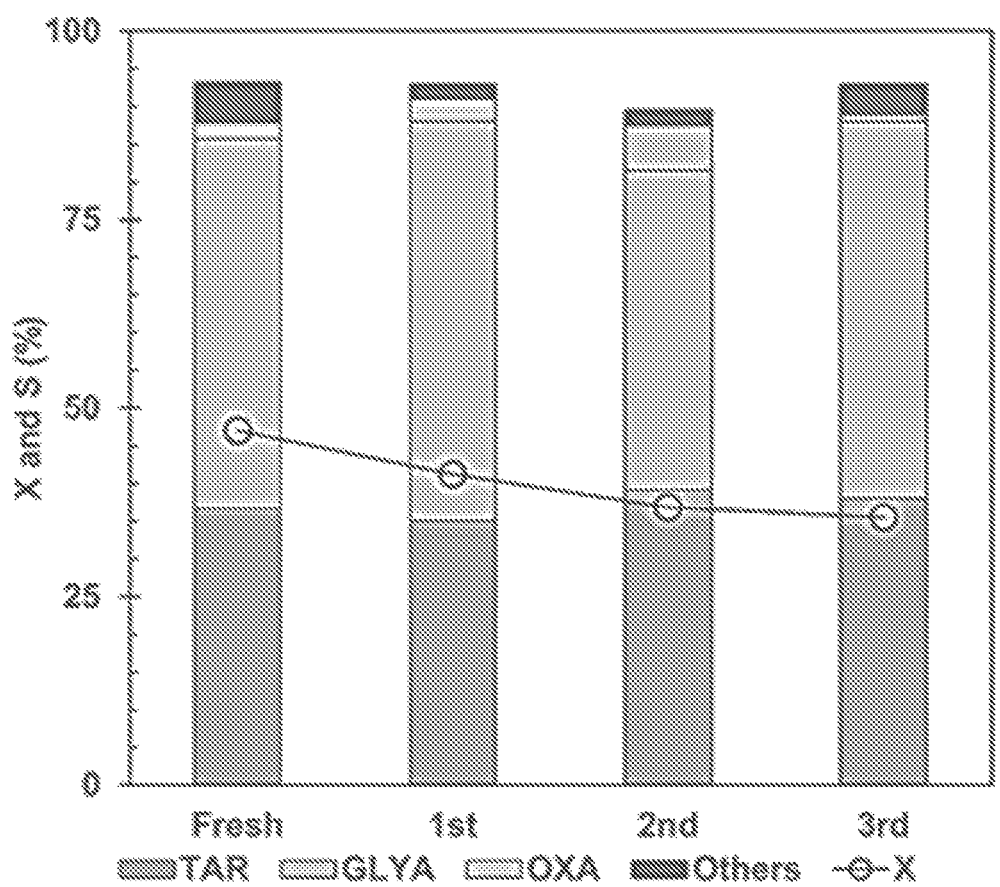
FIG. 38 depicts a conversion and selectivity of Co$_{0.15}$/Mg$_3$Al-s catalyst at 70° C.

Recycle experiments were carried out to study the stability of $Co_{0.15}/Mg_3Al$-s catalyst at 70° C. for glycerol conversion and results are shown in FIG. 38 at 6 hours reaction time. As seen from FIG. 38, the conversion of glycerol decreases from 47% to 35% after third recycle, suggesting catalyst deactivation occur during recycle study. The selectivities towards TAR and GLYA are almost unchanged.

It was found that Co catalysts immobilized on MgO—$Al_2O_3$ oxides prepared by sol-gel method exhibit 3.0 mol/$mol_{Co}$.h oxidation activity for glycerol conversion at 70° C. and 0.1 MPa $O_2$, with selectivity towards tartronic acid, glyceric acid and oxalic acid being 63%, 11%, and 17%, respectively. Compared to conventional stoichiometry oxidation by mineral chemicals, as well as reported noble metal catalysts, the studied Co catalysts show significant environmental and economic advantages for efficient tartronic acid production from biomass. Experimental studies on Co catalyst design show that catalysts from sol-gel method show 80% of combined selectivity towards tartronic acid and oxalic acid. Reaction profiles reveals the possible reaction pathways involved in formation of tartronic acid and other co-products in aqueous phase.

Example 7: PtFe Catalyst

Chemicals.

All chemicals used in this paper were purchased from Sigma Aldrich.

Synthesis of Monometallic Pt and Fe Catalysts Supported on $CeO_2$.

A solvothermal synthesis method was used to prepare monometallic Pt and Fe nanocatalysts. Particularly, about 20 mM of $Pt(acac)_2$ or $Fe(acac)_2$ were mixed with 20 mL of dimethylformamide (DMF) and certain amounts of $CeO_2$ powder in a glass insert. The mixture was then transported to a 100 mL Parr reactor. The reactor was sealed and flushed with $N_2$ thrice. The reactor was charged with 10 bar $N_2$ pressure at room temperature, before heated to target synthesis temperature (e.g., 200° C.). The slurry was stirred at 800 RPM for 12 hours before cooled down. The solid catalyst samples were centrifuged and washed with ethanol/$H_2O$ mixture (2/1 vol/vol) at least seven times to remove the surface DMF residues during catalyst synthesis. The as prepared catalysts were dried in a vacuum oven at 60° C. overnight before used in APO tests.

Synthesis of Bimetallic PtFe Catalysts Supported on $CeO_2$.

The procedures were similar to these shown in preparing monometallic catalysts. Specifically, 20 mM of Pt(acac)$_2$ with different amounts Fe(acac)$_2$ were mixed with DMF and certain amounts of $CeO_2$ powder in a glass insert. The molar ratio of Pt/Fe was ranged from 1/0.5, 1/1, 1/2, and 1/3. The following steps are the same as shown above. The catalysts were denoted as PtFe(0.5), PtFe(1), PtFe(2), respectively. In all mono and bimetallic catalysts, the weight loading of Pt is 1 w %.

Surface Characterization.

Transmission electron microscopy (TEM): sample preparation and detailed procedures were similar to that previously described. Samples were prepared by mixing solid catalyst with ethanol and agitating in an ultrasonic bath. 10 µL of catalyst sample was placed onto a copper mesh grid. The wet grid was allowed to air-dry for several minutes prior to examination under TEM. Around 200 particles were measured and average particle size as well as standard deviation were calculated. X-ray diffraction (XRD): This measurements was performed on a Bruker D8 powder diffractometer with a copper target ($CuK_\alpha$ radiation) operating at 40 kV and a current of 40 mA to analyze the crystal structures of materials.

APO of Glycerol.

The procedures for APO of glycerol tests were similar to these we previously described and thus are presented here in brief. In a typical run, about 0.05 g of solid catalyst were added to 25 mL glycerol (1.0 g) and NaOH (1.7 g) aqueous solution, which was transported to a 100 mL of three neck flask. The slurry was heated in an oil bath with precise temperature control before heated up to reaction temperature (e.g. 60° C., 80° C.). Once the liquid slurry was at reaction temperature, stirring rate was set at 1000 RPM, and $O_2$ was introduced in to the liquid by bubbling, which signified the start of an experimental run. Small amounts of liquid samples was taken during batch studies and acidified with $H_2SO_4$ solution before injected into HPLC (SHIMADZU with SH1011 column. Among all experiments, we find that the maximum solvent loss due to gas bubbling is about 2.9%, which is insignificant. The concentration of glycerol and oxidation products were thus obtained for the calculation of conversion (X), selectivity (S), carbon balance (C %) and turnover frequency (TOF, in mol/mol$_{Pt}$.h). Conversion is defined as the ratio of amount of glycerol converted to that initially charged. Selectivity towards a specific product is defined as the ratio of total amount of carbon atoms in this product generated during certain reaction time over that in converted glycerol. Carbon balance is defined as the ratio of total amount of carbon in all products to that of converted glycerol. TOF is defined as the amount of glycerol converted over Pt content in the reaction system per time. The definitions are shown below:

$$Conversion = \frac{C^{initial}_{moles,glycerol} - C^{final}_{moles,glycerol}}{C^{initial}_{moles,glycerol}} \quad \text{Formula 1}$$

$$Selectivity = \frac{C^{final}_{moles,products}}{C^{initial}_{moles,glycerol} - C^{final}_{moles,glycerol}} \quad \text{Formula 2}$$

$$Carbon(\%) = \frac{C^{final}_{moles,products}}{C^{converted}_{moles,glycerol}} \quad \text{Formula 3}$$

$$TOF = \frac{N_{glycerol,converted}}{N_{Pt} \cdot Time} \quad \text{Formula 4}$$

For kinetic modeling, a pseudo-first order kinetics with regard to glycerol concentration was considered as $O_2$ pressure is constant during experiments.

Figure 39:
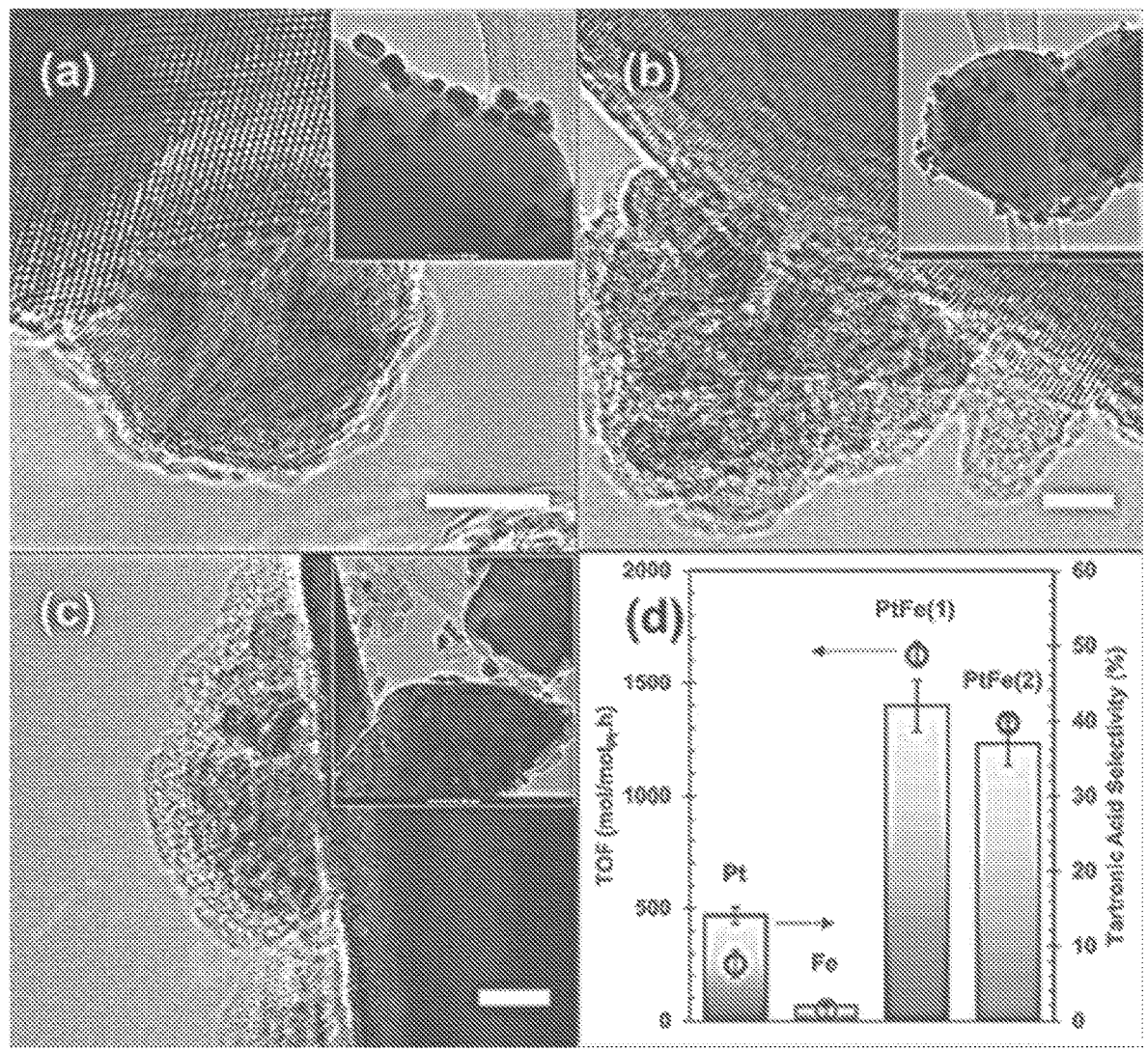
FIG. 39 depicts TEM images and glycerol performances of Pt, Fe, PtFe(1) and PtFe(2) catalysts.

The preliminary studies on APO of glycerol were carried out using $CeO_2$ supported Pt, Fe, PtFe(1) and PtFe(2) catalysts under the following experimental conditions: TOF values were calculated based on 0.5-2 hours reaction results at 70° C., tartronic acid selectivity was obtained at 24 hours reaction time at 70° C. Glycerol concentration: 0.43 kmol/m$^3$, NaOH/glycerol molar ratio: 4.0, catalyst amount: 2.2 kg/m$^3$, $O_2$ pressure: 0.1 Mpa. FIG. 39 depicts TEM images and glycerol performances of (a) Pt, (b) PtFe, (c) PtFe(2) (white bars indicate Snm). The results are presented in FIG. 39. Particularly, FIG. 39(a) shows that immobilized monometallic Pt species are polyhedron nanoparticles with both [111] and [100] surface facets exposed on $CeO_2$ support. The particle size ranges from 8 to 12 nm. Interestingly, when both Pt and Fe precursors were present during catalyst synthesis in dimethylformamide (DMF) solvent, unique disordered bimetallic PtFe clusters were observed. The high resolution TEM [HR-TEM, FIG. 39(b)] confirms this heterogeneous structure. Due to the large lattice mismatch between the two metals, disordered structures with both Pt and Fe clusters embedded with each other are dominantly present in PtFe (1) sample. PtFe (2) sample shown in FIG. 39(c) also exhibit a similar herocluster structure.

The APO studies on Pt, Fe, PtFe (1) and PtFe (2) catalyst samples demonstrate a synergistic activity and enhanced selectivity for glycerol conversion. It is necessary to mention that the major oxidation products from glycerol conversion include glyceric, tartronic, lactic, glycolic, oxalic and formic acids. Primary oxidation of glycerol generates glyceraldehyde as the key intermediate. This intermediate can be quickly oxidized to glyceric acid as the major product, which may undergo further (secondary) oxidation of another hydroxyl group to form valuable tartronic acid. If dehydration occurs, glyceraldehyde can lead to the formation of lactic acid, while C—C cleavage followed by further oxidation will generate formic and glycolic acids. Based on the experiments, as seen in FIG. 39(d), monometallic Pt and Fe only display 252.6±61.9 mol/mol$_{Pt}$.h and 47.7±29.3 mol/mol$_{Fe}$.h oxidation activity in glycerol conversion, while bimetallic PtFe(1) and PtFe(2) both display synergistic enhancement. Particularly, PtFe(1) sample exhibits a remarkable 1626.2±54.8 mol/mol$_{Pt}$.h and PtFe(2) shows 1322.4±28.1 mol/mol$_{Pt}$.h oxidation activity. Moreover, the selectivity towards tartronic acid on monometallic Pt catalyst is approximately 14% (after 24 hours reaction), while in sharp contrast, bimetallic PtFe(1) and PtFe(2) catalysts give about 37-42% selectivity.

The mechanism of lattice mismatch growth and the structure dependent glycerol oxidation rates on bimetallic PtFe nanocatalysts were also studied. The possible mechanism of cluster formation during solvothermal synthesis was first investigated by doping various amounts of Fe species to Pt structures ranging from 1/0.5 to 1/2 Pt/Fe molar ratios. This was followed by a detailed reaction modeling of glycerol oxidation on selected PtFe and Pt catalysts.

Figure 40:
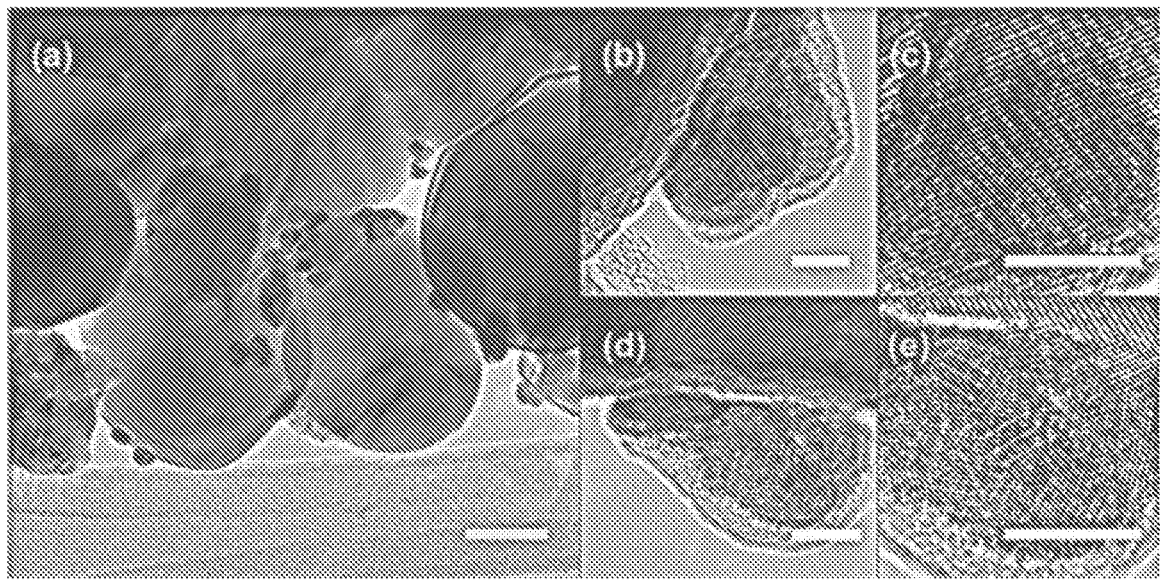
FIG. 40 depicts TEM images for PtFe(0.5) catalyst sample.
Figure 42:
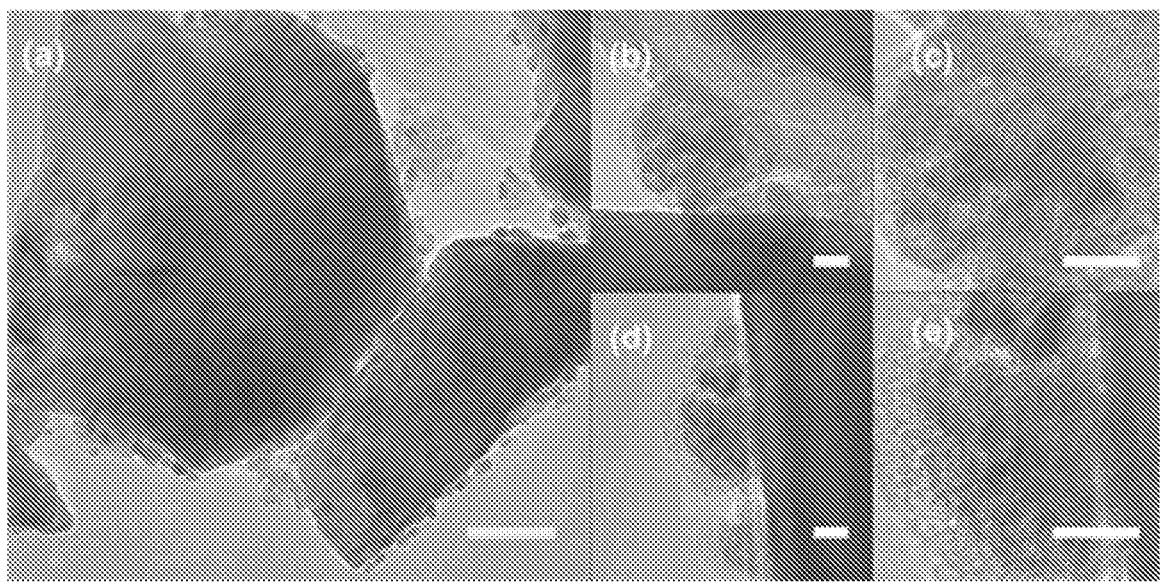
FIG. 42 depicts TEM images for PtFe(2) catalyst sample.
Figure 43A:
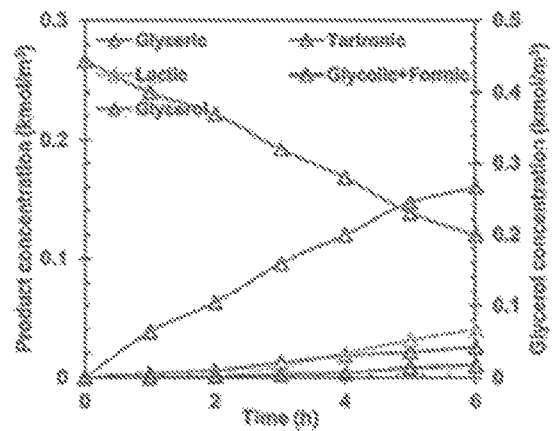
FIGS. 43(a)-(f) depict concentration-time profiles of glycerol conversion on Pt/CeO$_2$ and PtFe/CeO$_2$.
Figure 43D:
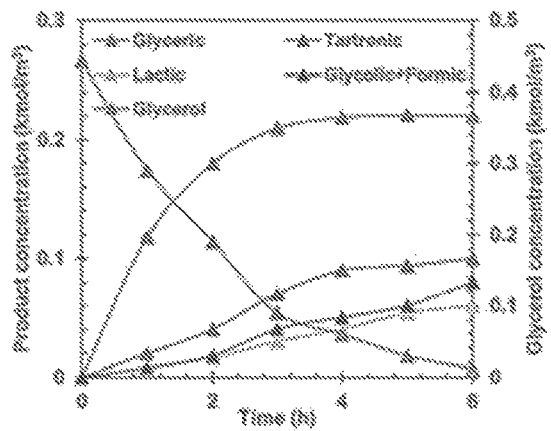
Figure 43B:
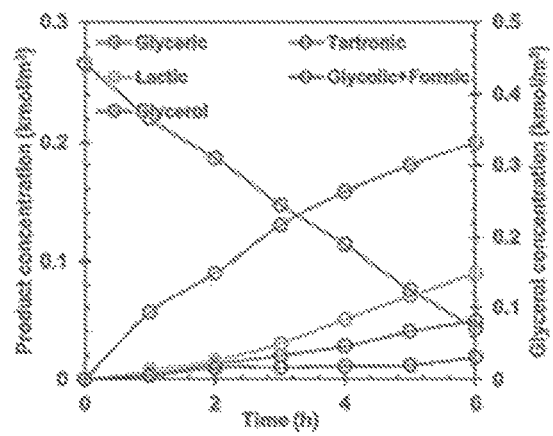
Figure 43E:
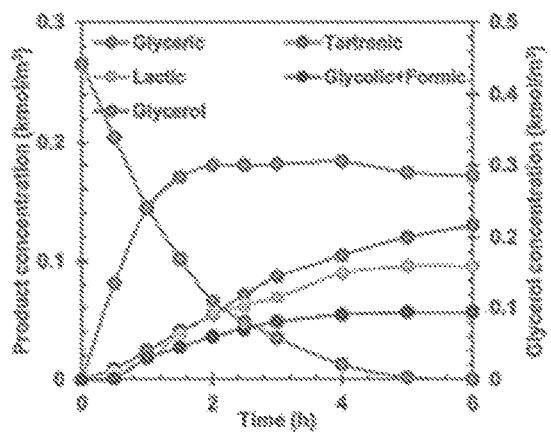
Figure 43C:
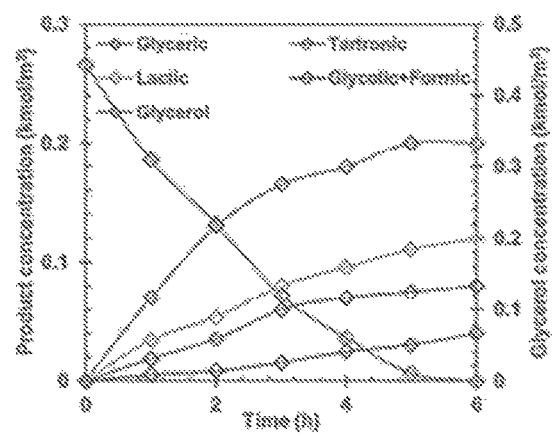
Figure 43F:
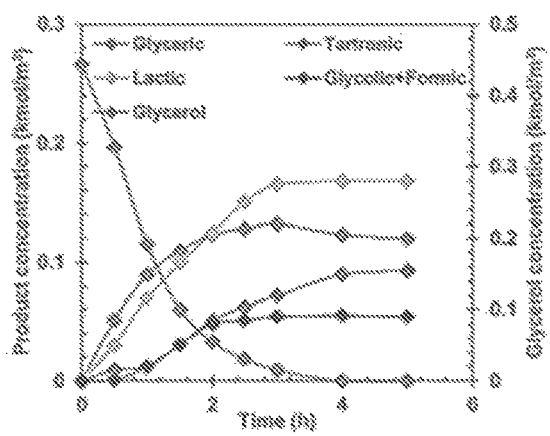

HR-TEM images of bimetallic PtFe samples with 1/0.5, 1/1, 1/2 of Pt/Fe ratios are shown in FIG. 40: PtFe(0.5), GIG. 41: PtFe(1); and FIG. 42: PtFe. Bars indicate 50 nm and 5 nm. These figures reveal the possible growing mechanism of bimetallic PtFe heteroclusters. When the content of Fe is small (PtFe(0.5), FIG. 40(*a*)), we find that twin phases of Pt and Fe were dominant within the bimetallic sample. To illustrate, detailed surface atomic arrangement of PtFe(0.5) sample are shown in FIGS. 40(*b*), (*c*). The twin phases are enclosed by [111] and [100] crystal facets of fcc PtFe structure. Although herocluster structure is not obvious at this stage, further inspection (see FIG. 40(*c*)) shows that PtFe surface planes with different orientation start to formulate. White arrows indicate the possible orientation of boundaries among twin domains. Similar surface geometry is also observed at other regions (see FIGS. 40(*d*), (*e*)) within the same catalyst sample.

Figure 41:
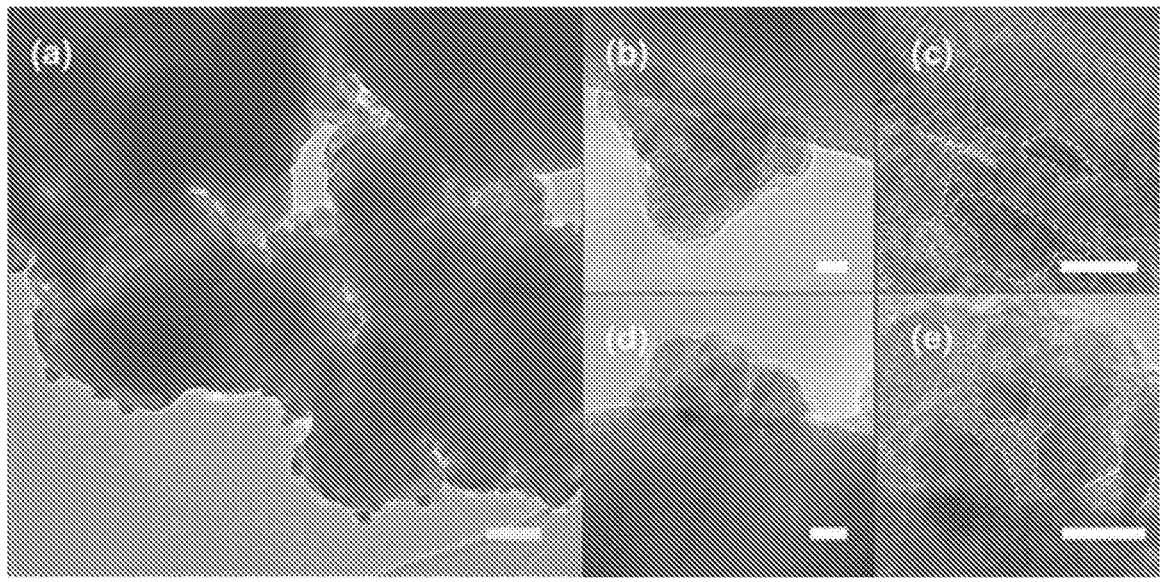
FIG. 41 depicts TEM images for PtFe(1) catalyst sample.

As more Fe content is present in this system [PtFe(1)], heterogeneity of the bimetallic clusters is significantly enhanced. Consequently, Pt [111] and [100] surface planes started to diminish. As seen in FIG. 41(*a*), PtFe herocluster structures are observed on various different sample regions. The PtFe(1) sample exhibit a completely disordered cluster-in-cluster geometry rather than fcc structures. HR-TEM of selected two regions (FIGS. 41(*b*), (*d*)) further confirm the existence of bimetallic heteroclusters on $CeO_2$ support. To our interest, clusters in this sample have clear boundaries [white lines in FIGS. 41(*c*), (*e*)]. This observation implies that when more Fe species existing in bimetallic PtFe clusters, large lattice mismatch might be the dominant factor that governs the growth of nanoparticles.

There have been two major mechanisms in the literature discussed for PtFe crystal growth, one considering $Fe^{3+}$ etching effects during Pt nanoparticle growth while another proposing the strong driving force for anisotropic growth with twin crystals. In this case, at the initial growth of bimetallic PtFe clusters, we believe that $Fe^{3+}$ etching is significant. The two metal cation species ($Fe^{3+}$ and $Pt^{2+}$) were both reduced in the presence of DMF under hydrothermal conditions. The etching effect, also called "galvanic displacement" between existing $Fe^{3+}$ cations and surface $Pt^0$ results in formation of $Fe^{2+}$ and $Pt^{2+}$. Due to the preferable adsorption of $Fe^{3+}$ on Pt [100] surface plane, the "chemical corrosion" of $Pt^0$ to $Pt^{2+}$ species occurred which affect the surface geometry of Pt nanoparticles. In a parallel pathway, $Fe^0$ can also be oxidized (displaced) by $Pt^{2+}$ to $Fe^{2+}$ in DMF medium. At this stage, Pt nanoparticles with concave structures can be formed due to the etching effect. But when this etching is not significant, in other words, $Fe^{3+}$ is largely consumed (reduced to $Fe^{2+}$ or $Fe^0$) in the reaction solution. Anisotropic growth induced by lattice mismatch [PtFe(1)] is dominant on the surface of the twined structured formed initially [PtFe(0.5)]. Both etching and lattice mismatch strain between seeded twin structures and newly formed shells contribute the final geometry of bimetallic PtFe clusters. As a result, the heterogeneity of bimetallic PtFe crystals is enhanced, which was confirmed by element line scan analysis. This alternative mechanism proposed based on HR-TEM images shown in FIG. 40 (PtFe(0.5)) and FIG. 41 (PtFe(1)) is further supported by the surface geometry presented in FIG. 42 (PtFe(2)).

PtFe(1) catalyst shows slightly better glycerol conversion and tartronic acid selectivity compared to the other two PtFe(0.5) and PtFe(2) samples as shown in Table 16.

TABLE 16

Glycerol oxidation on PtFe (0.5), PtFe(1) and PtFe(2) catalysts

| Catalyst | X (%) | Selectivity (%) | | | |
|---|---|---|---|---|---|
| | | Glyceric | Tartronic | Lactic | Others |
| PtFe (0.5) | 42.7 | 75.2 | 12.1 | 9.6 | 3.3 |
| PtFe (1) | 57.1 | 71.1 | 15.8 | 6.3 | 7.1 |
| PtFe (2) | 54.1 | 77.6 | 12.2 | 3.3 | 5.3 |

T: 70° C., reaction time: 2 hours, glycerol concentration: 0.43 kmol/m³, NaOH/glycerol molar ratio: 4.0, catalyst amount: 2.2 kg/m³, $O_2$ pressure: 0.1 MPa, other experimental details refer to Experimental Section.

Therefore, further kinetic studies were focused on monometallic Pt and bimetallic PtFe(1) catalyst samples. Particularly, concentration-time profiles at 60° C., 70° C. and 80° C. on these two catalysts were collected and are shown in FIG. 43, in which FIG. 43 depicts concentration-time profiles of glycerol conversion on $Pt/CeO_2$ (a-c, hollow) and $PtFe/CeO_2$ (d-e, solid). 60° C.: triangle; 70° C.: round; 80° C.: diamond. Experimental conditions: glycerol concentration: 0.43 kmol/m³, NaOH/glycerol molar ratio: 4.0, catalyst amount: 2.2 kg/m³, $O_2$ pressure: 0.1 Mpa.

It is shown that as reaction temperature increases, glycerol conversion rate on both Pt and PtFe(1) catalysts is enhanced. Specifically, when reaction temperature increases from 60° C. to 80° C., the initial rate of glycerol consumption is enhanced by almost three fold on Pt catalyst, while on PtFe(1) catalyst this value is about two fold. For product distribution, obviously glyceric acid is the dominant product on both catalysts within 6 hours reaction time. But the concentration of tartronic acid is about 3-6 times higher on bimetallic PtFe(1) than Pt catalyst. In addition, lactic acid concentration is enhanced significantly with reaction temperature.

Figure 44:
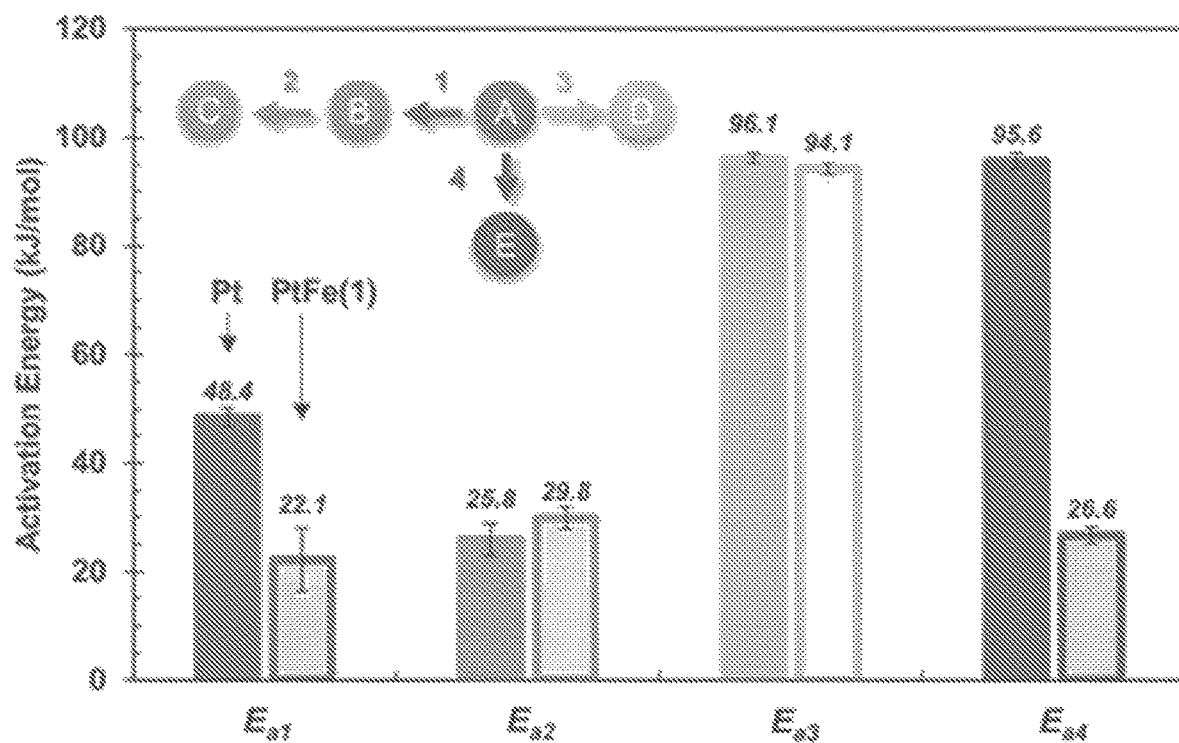
FIG. 44 depicts activation barriers for glycerol conversion in presence of Pt and PtFe(1) catalysts.

With the experimental observation above, further kinetic modeling was carried out systematically. The purpose of kinetic analysis is to obtain quantitative assessment of the role of Fe in Pt system during glycerol oxidation. Specific reactions involved in glycerol conversion including (1) oxidation of glycerol (A) to glyceric acid (B, primary oxidation, $r_1$), (2) oxidation of glyceric to tartronic acid (C, secondary oxidation, $r_2$), (3) oxidation of glycerol to lactic acid (D, $r_3$) and (4) glycerol to formic and glycolic acids (E, C—C cleavage and oxidation, $r_4$) were considered for this part of study. Activation barriers are shown in FIG. 44, and reaction pathways. FIG. 44 depicts activation barriers for glycerol conversion in presence of Pt and PtFe(1) catalysts. (A: glycerol, B: glyceric acid, C: tartronic acid, D: lactic acid, E: formic and glycolic acids; $E_{a1}$-$E_{a4}$ represent activation energies for $r_1$, $r_2$, $r_3$ and $r_4$, respectively). Kinetic parameters such as rate constants for $r_1$-$r_4$ are shown in Table 17.

TABLE 17

Rate constants on Pt and PtFe(1) catalysts

| Catalyst | Rate constant ($10^{-2}$ h$^{-1}$) | 60° C. | 70° C. | 80° C. |
|---|---|---|---|---|
| Pt | $k_1$ | 0.95 | 1.56 | 2.56 |
| | $k_2$ | 0.58 | 0.68 | 0.98 |

TABLE 17-continued

Rate constants on Pt and PtFe(1) catalysts

| Catalyst | Rate constant ($10^{-2}$ h$^{-1}$) | 60° C. | 70° C. | 80° C. |
|---|---|---|---|---|
|  | $k_3$ | 0.15 | 0.48 | 1.08 |
|  | $k_4$ | 0.04 | 0.08 | 0.28 |
| PtFe(1) | $k_1$ | 3.62 | 4.96 | 5.70 |
|  | $k_2$ | 0.92 | 1.38 | 1.68 |
|  | $k_3$ | 0.55 | 1.48 | 3.78 |
|  | $k_4$ | 0.92 | 1.18 | 1.58 |

Figure 45:
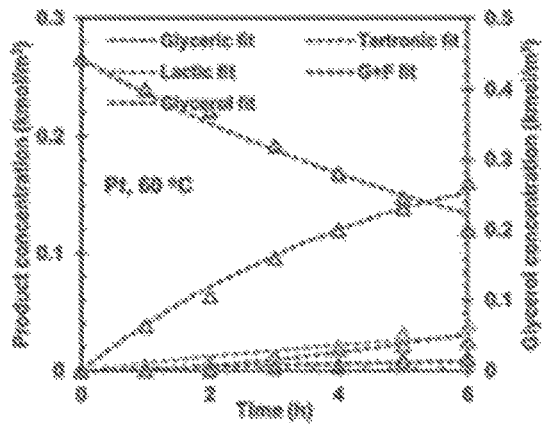
FIG. 45 depicts a fitted concentration time profiles on Pt and PtFe(1) catalysts.
Figure 45:
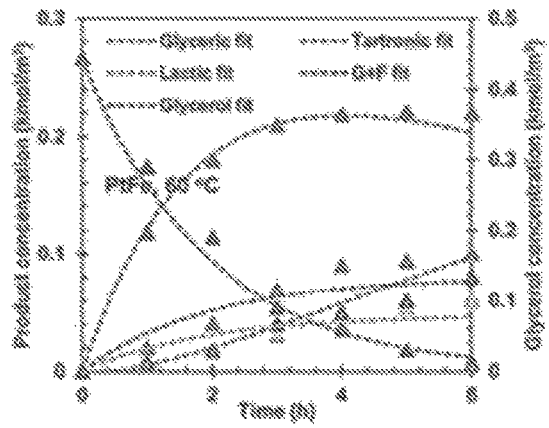
Figure 45:
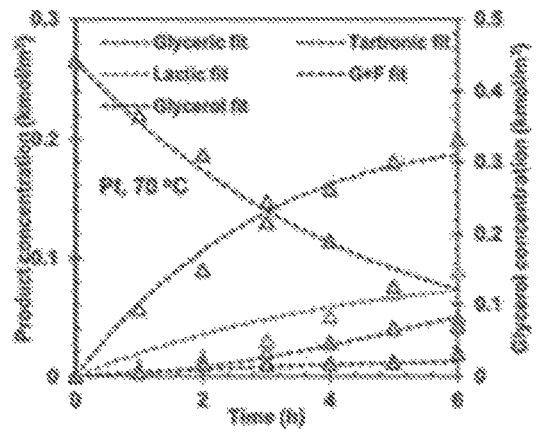
Figure 45:
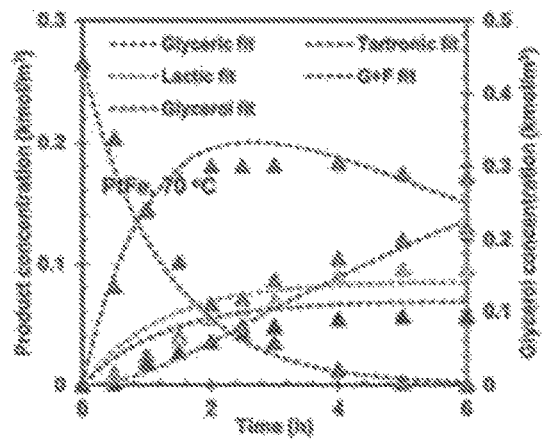
Figure 45:
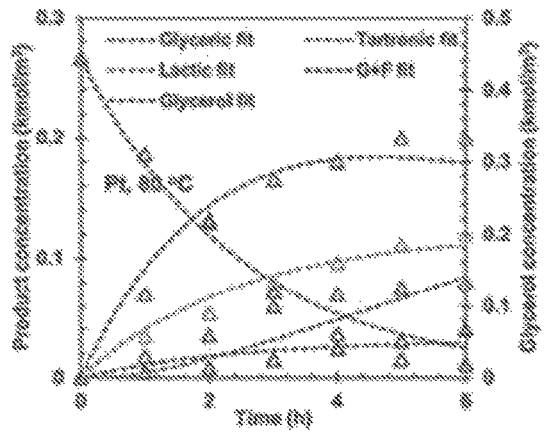
Figure 45:
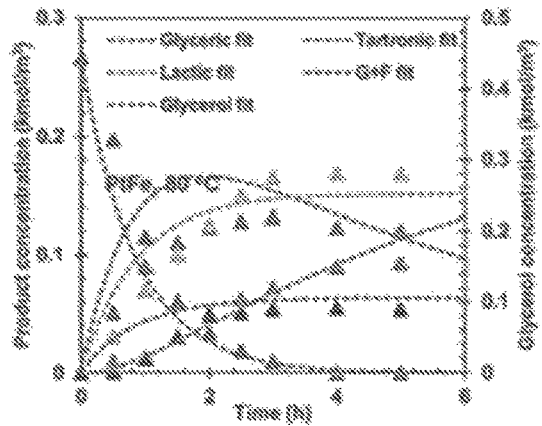

Rate constants were regressed and data was fitted as shown in FIG. 45. The kinetic analysis was used for activation barrier calculation. As shown in FIG. 44, the presence of Fe was lower than the activation barrier for $r_1$ (glycerol to glyceric acid) on Pt catalyst surface, while the energy required for $r_2$ (glyceric to tartronic acid) is almost similar on two catalysts. The activation barrier for lactic acid formation is almost unchanged but that for C—C cleavage is much lower on bimetallic PtFe(1) catalyst. Therefore it appears that bimetallic PtFe catalysts enhance the tartronic acid formation by significantly lowering the activation barriers for primary oxidation. Due to much lower activation energy for C—C cleavage reactions, formic and glycolic acid formation is also found to be significant on bimetallic PtFe catalysts.

Strong adsorption of —C═O group on noble metal surfaces (e.g. Pt, Pd) often prevent further (oxidation) reactions from happening. The high tendency for decarboxylation or oxidative decarbonylation due to the unfavorable strong interaction observed in literature is known to lead to significant side reactions such as CO formation and catalyst poisoning at low temperature. By doping Fe (promoters) to Pt systems, the binding energy between —C═O functional groups and metal atoms is lowered. This favorably decreases the surface coverage of —C═O (and —COOH) groups, or increases the possibility of catalytic turnovers on metal sites, thus facilitates rates of oxidation reactions on catalyst surface. The lower activation barrier for primary reaction step on bimetallic PtFe(1) catalyst confirms this hypothesis. The presence of Fe promotes desorption of glyceric acid on active sites thus secondary oxidation reactions are enhanced. Therefore tartronic acid selectivity is much higher on bimetallic PtFe nanocatalysts.

Figure 46:
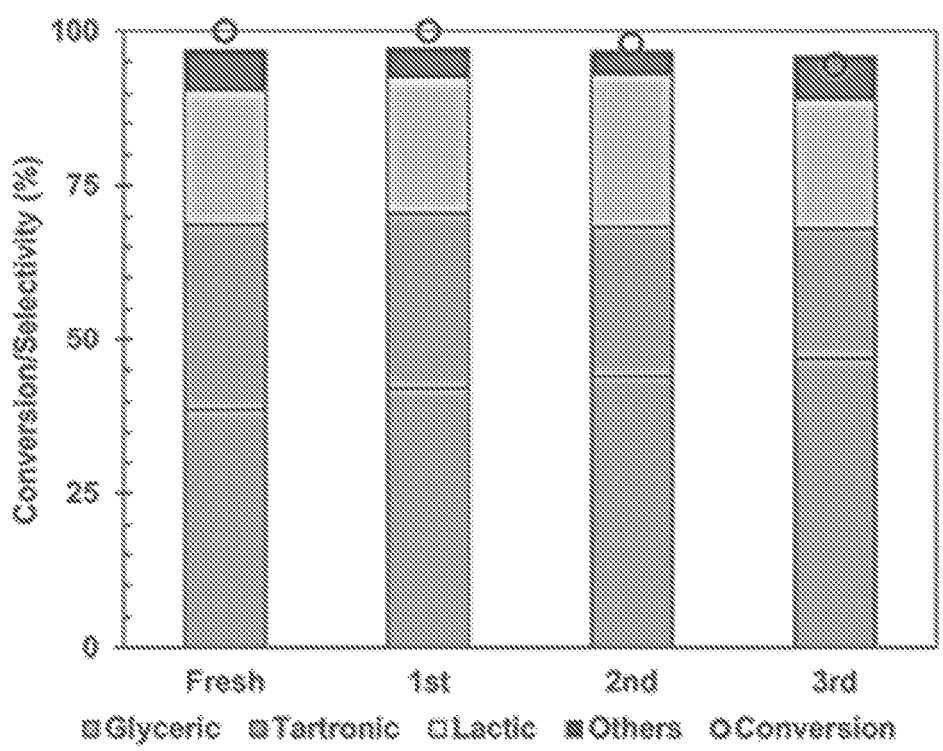
FIG. 46 depicts recycle studies of PtFe(1) catalyst at 70° C.

Stability was also studied investigated during recycle studies at 70° C. We find that there exists an observable deactivation of PtFe catalysts after three recycles. Particularly, the conversion of glycerol displays a slight decrease from 100% to 95%, with selectivity towards tartronic acid decreasing from 32% to 22%, after third recycle (FIG. 46).

In addition, we also tested PtFe(1) catalyst for oxidation of sorbitol, a $C_6$ polyol, at 70° C. Complete conversion was observed after 6 hours reaction time and the major products included glyceric (36%), tartronic (12%), gluconic (11%), glucaric (18%), oxalic (9%) and formic (11%) acids. This result shows that lattice mismatched PtFe(1) nanocatalyst can efficiently produce valuable DCAs from various biomass feedstocks.

Unique bimetallic PtFe herocluster structures were induced by the large lattice constant mismatch between the two metals (Pt: 0.392 nm, Fe: 0.287 nm; 27% mismatch). Such unique materials, generated from lattice mismatched growth, display not only strong synergistic activity but also enhanced selectivity in biomass oxidation. The special PtFe herocluster nanocatalysts exhibit a remarkable six-fold enhancement in oxidation activity and three-fold higher selectivity to DCAs compared with monometallic Pt and Fe catalysts. A value of 227.6 mol/mol$_{Pt}$.h for tartronic acid (a DCA) formation rate was achieved. The bimetallic PtFe nanoclusters exhibit remarkable performances for low temperature conversion of renewable biomass resources to value-added chemicals.

From the foregoing it will be seen that this invention is one well adapted to attain all ends and objectives hereinabove set forth, together with the other advantages which are obvious and which are inherent to the invention.

While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

We claim:

1. A process for oxidizing a substrate comprising contacting a substrate with an oxidant in the presence of an alloy catalyst to form one or more carboxylic acids, wherein the alloy catalyst is formed from the following process:
   combining a metal precursor of a first metal, a metal precursor of a second metal and a solid support in a solvent;
   co-precipitating said first metal precursor and said second metal precursor to form the alloy catalyst.

2. The process of claim 1, wherein the combining step of the alloy catalyst formation process comprises:
   forming a metal precursor solution comprising a metal precursor of a first metal and a metal precursor of a second metal;
   forming a solid support solution comprising a solid support and a solvent; and
   combining said metal precursor solution and said solid support solution to form a combined solution.

3. The process of claim 1, wherein the precipitating step of the alloy catalyst formation process comprises adding a reducing agent.

4. The process of claim 1, wherein said alloy catalyst comprises:
   a first metal selected from the group consisting of platinum, silver, gold, cobalt and palladium; and
   a second metal selected from the group consisting of molybdenum, titanium, vanadium, manganese, magnesium, iron, cobalt, nickel, copper, gold, platinum, palladium, ruthenium, iridium, and rhodium; and
   wherein said first metal and said second metal are not the same.

5. The process of claim 4, wherein said first metal is platinum and said second metal is selected from the group consisting of copper, palladium, iron, manganese, and cobalt.

6. The process of claim 5, wherein said first metal is platinum and said second metal is selected from the group consisting of copper, palladium, and manganese.

7. The process of claim 6, wherein said second metal is copper.

8. The process of claim 7, wherein the atomic ratio of platinum to copper is from 1:5 to 1:1.

9. The process of claim 8, wherein the atomic ratio of platinum to copper is from 1:2 to 1:4.

10. The process of claim 4, wherein said alloy catalyst is a bimetallic alloy catalyst selected from the group consisting of platinum/copper, platinum/palladium, platinum/cobalt, platinum/iron, cobalt/magnesium, and gold/palladium.

11. The process of claim 1, wherein said substrate is selected from the group consisting of sugars, polyols, furfural alcohols, and polyhydroxycarboxylic acids.

12. The process of claim 11, wherein said substrate is a $C_3$-$C_{12}$ sugar, polyol, furfural alcohol, or polyhydroxycarboxylic acid.

13. The process of claim 12, wherein said substrate is a $C_6$-$C_{12}$ sugar, polyol, or polyhydroxycarboxylic acid.

14. The process of claim 11, wherein said substrate is selected from the group consisting of glucose, gluconic acid, fructose, 5-hydroxymethylfurfural (HMF), furfuryl alcohol, galactose, xylose, sucrose, lactose, maltose, trehalose, glycerol, sorbitol, mannitol, lactitol, xylitol, erythritol, isomalt, maltitol, ethylene glycol, 1,3-propanediol, and 1,6-hexanediol.

15. The process of claim 1, wherein said carboxylic acid is a monocarboxylic acid selected from the group consisting of glycolic acid, glyceric acid, formic acid, lactic acid, 3-hydroxy propionic acid and furfuryl carboxylic acid.

16. The process of claim 1, wherein said carboxylic acid is a dicarboxylic acid selected from the group consisting of glucaric acid, tartronic acid, malonic acid, oxalic acid, adipic acid and furan dicarboxylic acid.

17. The process of claim 1, wherein said carboxylic acid is a polyhydroxycarboxylic acid.

18. The process of claim 17, wherein said polyhydroxycarboxylic acid is selected from the group consisting of xylonic acid and gluconic acid.

19. The process of claim 1, wherein a temperature of said process is maintained at 20 to 150° C.

20. The process of claim 1 wherein a pressure of said process is maintained at 1 to 50 bar.

21. The process of claim 1, wherein a concentration of said substrate ranges from 0.1% to 70% ((wt./wt.) %) of a reaction mixture comprising the substrate and oxidant.

22. The process of claim 1, wherein said substrate and said oxidant form a reaction mixture and said reaction mixture additionally comprises a base oxide promoter or a hydroxide.

23. The process of claim 22, wherein said reaction mixture additionally comprises a hydroxide that is selected form the group consisting of sodium hydroxide (NaOH), potassium hydroxide (KOH), cesium hydroxide (CsOH), magnesium hydroxide ($Mg(OH)_2$), calcium hydroxide ($Ca(OH)_2$), or barium hydroxide ($Ba(OH)_2$).

24. The process of claim 22, wherein said reaction mixture additionally comprises a base oxide promoter that is selected from the group consisting of calcium oxide (CaO), barium oxide (BaO), magnesium oxide (MgO), or cerium oxide ($CeO_2$).

25. The process of claim 1, wherein said oxidant is selected from the group consisting of air, molecular oxygen ($O_2$), dilute hydrogen peroxide ($H_2O_2$), alkyl hydroperoxide, tert-butyl hydroperoxide (TBHP), and tert-amyl hydroperoxide (TAHP).

* * * * *